US010149713B2

(12) United States Patent
Elliott et al.

(10) Patent No.: US 10,149,713 B2
(45) Date of Patent: Dec. 11, 2018

(54) ELECTROSURGICAL SYSTEM

(71) Applicant: Applied Medical Resources Corporation, Rancho Santa Margarita, CA (US)

(72) Inventors: Patrick Elliott, Rancho Santa Margarita, CA (US); Gary Johnson, Rancho Santa Margarita, CA (US); Duy Nguyen, Rancho Santa Margarita, CA (US); Daniel McFarland, Dana Point, CA (US); Jagdish Sabarad, Rancho Santa Margarita, CA (US); Benjamin Linville-Engler, Rancho Santa Margarita, CA (US); Jeremy Albrecht, Rancho Santa Margarita, CA (US); Dan Durant, Rancho Santa Margarita, CA (US); Gerald Kowalski, Lake Forest, CA (US); Lou Tiberia, Rancho Santa Margarita, CA (US); Michael Whitlock, Rancho Santa Margarita, CA (US); Michael Logan, Rancho Santa Margarita, CA (US); Igor Gorin, Rancho Santa Margarita, CA (US); Kevin Hudson, Rancho Santa Margarita, CA (US); Hank Jacobs, Rancho Santa Margarita, CA (US); Thomas Matthews, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 580 days.

(21) Appl. No.: 14/848,116

(22) Filed: Sep. 8, 2015

(65) Prior Publication Data
US 2016/0000495 A1  Jan. 7, 2016

Related U.S. Application Data

(63) Continuation of application No. PCT/US2015/031452, filed on May 18, 2015.
(Continued)

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1445* (2013.01); *A61B 2018/00077* (2013.01);
(Continued)

(58) Field of Classification Search
CPC ............ A61B 18/1233; A61B 18/1445; A61B 2090/034; A61B 2018/00077;
(Continued)

(56) References Cited

U.S. PATENT DOCUMENTS 371,664 A   10/1887  Brannan et al.
702,472 A   6/1902   Pignolet
(Continued)

FOREIGN PATENT DOCUMENTS

DE   40 24 636 A1   2/1992
DE   40 24 636 C2   12/1992
(Continued)

OTHER PUBLICATIONS

Bertil Vallfors and Bjorn Bergdahl, Automatically controlled bipolar electrocoagulation—"COA-COMP", Neurosurg. Rev., 1984, pp. 187-190.
(Continued)

*Primary Examiner* — Jaymi Della
(74) *Attorney, Agent, or Firm* — Patrick Y Ikehara

(57) ABSTRACT

An electrosurgical generator arranged to supply radio frequency (RF) energy to fuse tissue is provided. The generator
(Continued)

is arranged to supply RF energy through a removably coupled electrosurgical instrument to fuse tissue grasped by the instrument. The generator monitors a phase angle of the supplied RF energy and adjusts or terminates the supplied RF energy based on the monitored phase angle in comparison to predetermined thresholds and conditions to optimally fuse the tissue. The electrosurgical instrument conducts radio frequency energy to fuse tissue captured between the jaws and a blade to mechanically cut tissue between the jaws. A conductive post positioned on the jaw adjacent to the blade.

18 Claims, 49 Drawing Sheets

Related U.S. Application Data

(60) Provisional application No. 61/994,415, filed on May 16, 2014, provisional application No. 61/994,185, filed on May 16, 2014, provisional application No. 61/994,192, filed on May 16, 2014, provisional application No. 61/994,215, filed on May 16, 2014.

(51) Int. Cl.
  *A61B 18/00* (2006.01)
  *A61B 90/00* (2016.01)

(52) U.S. Cl.
  CPC .......... *A61B 2018/00607* (2013.01); *A61B 2018/00619* (2013.01); *A61B 2018/00642* (2013.01); *A61B 2018/00708* (2013.01); *A61B 2018/00738* (2013.01); *A61B 2018/00767* (2013.01); *A61B 2018/00869* (2013.01); *A61B 2018/00892* (2013.01); *A61B 2018/126* (2013.01); *A61B 2018/1455* (2013.01); *A61B 2090/034* (2016.02)

(58) Field of Classification Search
  CPC .......... A61B 2018/00607; A61B 2018/00642; A61B 2018/00708; A61B 2018/00738; A61B 2018/00767; A61B 2018/00869; A61B 2018/00892; A61B 2018/126; A61B 2018/1455
  See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,935,289 A | 4/1933 | Evans |
| 2,002,594 A | 5/1935 | Wappler et al. |
| 2,031,682 A | 2/1936 | Wappler et al. |
| 2,113,246 A | 4/1938 | Wappler |
| 2,176,479 A | 10/1939 | Willis |
| 2,305,156 A | 4/1941 | Grubel |
| 2,632,661 A | 3/1953 | Cristofv |
| 2,827,056 A | 3/1958 | Degelman |
| 3,085,566 A | 4/1963 | Tolles |
| 3,459,187 A | 8/1969 | Pallotta |
| 3,494,363 A | 2/1970 | Jackson |
| 3,588,710 A | 6/1971 | Masters |
| 3,651,811 A | 3/1972 | Hildebrandt et al. |
| 3,685,518 A | 8/1972 | Beuerle et al. |
| 3,780,416 A | 12/1973 | Rider |
| 3,826,263 A | 7/1974 | Cage |
| 3,911,766 A | 10/1975 | Fridolph |
| 3,920,021 A | 11/1975 | Hiltebrandt |
| 3,938,527 A | 2/1976 | Rioux |
| 3,963,030 A | 6/1976 | Newton |
| 3,970,088 A | 7/1976 | Morrison |
| 3,980,085 A | 9/1976 | Ikuno |
| 3,987,795 A | 10/1976 | Morrison |
| 4,030,501 A | 6/1977 | Archibald |
| 4,041,952 A | 8/1977 | Morrison, Jr. et al. |
| 4,043,342 A | 8/1977 | Morrison |
| 4,060,088 A | 11/1977 | Morrison, Jr. et al. |
| 4,074,718 A | 2/1978 | Morrison, Jr. |
| 4,089,336 A | 6/1978 | Cage |
| 4,092,986 A | 6/1978 | Schneiderman |
| 4,094,320 A | 6/1978 | Newton et al. |
| 4,114,623 A | 9/1978 | Meinke |
| 4,126,137 A | 11/1978 | Archibald |
| 4,154,240 A | 5/1979 | Ikuno |
| 4,171,700 A | 10/1979 | Farin |
| 4,181,131 A | 1/1980 | Ogui |
| 4,188,927 A | 2/1980 | Harris |
| 4,196,734 A | 4/1980 | Harris |
| 4,198,957 A | 4/1980 | Cage et al. |
| 4,198,960 A | 4/1980 | Utsugi |
| 4,200,104 A | 4/1980 | Harris |
| 4,231,372 A | 11/1980 | Newton |
| 4,237,887 A | 12/1980 | Gonser |
| 4,244,371 A | 1/1981 | Farin |
| 4,325,374 A | 4/1982 | Komiya |
| 4,331,149 A | 5/1982 | Gonser |
| 4,338,940 A | 7/1982 | Ikuno |
| 4,352,156 A | 9/1982 | Gyugyi |
| 4,370,980 A | 2/1983 | Lottick |
| 4,416,276 A | 11/1983 | Newton |
| 4,416,277 A | 11/1983 | Newton et al. |
| 4,427,014 A | 1/1984 | Bel |
| 4,429,694 A | 2/1984 | McGreevy |
| 4,463,759 A | 8/1984 | Garito et al. |
| 4,487,489 A | 12/1984 | Takamatsu |
| 4,514,619 A | 4/1985 | Kugelman |
| 4,522,206 A | 6/1985 | Whipple et al. |
| 4,552,143 A | 11/1985 | Lottick |
| 4,569,131 A | 2/1986 | Faulk et al. |
| 4,569,345 A | 2/1986 | Manes et al. |
| 4,590,934 A | 5/1986 | Malis et al. |
| 4,599,553 A | 7/1986 | Brennen et al. |
| 4,630,218 A | 12/1986 | Hurley |
| 4,632,109 A | 12/1986 | Paterson |
| 4,644,950 A | 2/1987 | Valli |
| 4,651,280 A | 3/1987 | Chang et al. |
| 4,655,216 A | 4/1987 | Tischer |
| 4,657,018 A | 4/1987 | Hakky |
| 4,658,815 A | 4/1987 | Farin et al. |
| 4,658,819 A | 4/1987 | Harris et al. |
| 4,658,820 A | 4/1987 | Klicek |
| 4,674,498 A | 6/1987 | Stasz |
| 4,685,459 A | 8/1987 | Koch et al. |
| 4,699,146 A | 10/1987 | Sieverding |
| 4,712,545 A | 12/1987 | Honkanen |
| 4,716,897 A | 1/1988 | Noguchi et al. |
| 4,727,874 A | 3/1988 | Bowers |
| 4,739,759 A | 4/1988 | Rexroth et al. |
| 4,741,334 A | 5/1988 | Irnich |
| 4,752,864 A | 6/1988 | Clappier |
| 4,754,757 A | 7/1988 | Feucht |
| 4,788,977 A | 12/1988 | Farin et al. |
| 4,802,476 A | 2/1989 | Noerenberg et al. |
| 4,818,954 A | 4/1989 | Flachenecker |
| 4,827,927 A | 5/1989 | Newton |
| 4,848,335 A | 7/1989 | Manes |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,872,456 A | 10/1989 | Hasson |
| 4,887,612 A | 12/1989 | Esser et al. |
| 4,889,722 A | 12/1989 | Sheffield et al. |
| 4,903,696 A | 2/1990 | Stasz et al. |
| 4,905,691 A | 3/1990 | Rydell |
| 4,922,903 A | 5/1990 | Welch et al. |
| 4,936,281 A | 6/1990 | Stasz |
| 4,937,254 A | 6/1990 | Sheffield et al. |
| 4,938,761 A | 7/1990 | Ensslin |

(56) References Cited

U.S. PATENT DOCUMENTS

| | | |
|---|---|---|
| 4,942,313 A | 7/1990 | Kinzel |
| 4,958,539 A | 9/1990 | Stasz et al. |
| 4,969,885 A | 11/1990 | Farin |
| 4,976,711 A | 12/1990 | Parins et al. |
| 5,007,908 A | 4/1991 | Rydell |
| 5,013,312 A | 5/1991 | Parins et al. |
| 5,015,227 A | 5/1991 | Broadwin et al. |
| 5,016,521 A | 5/1991 | Haka |
| 5,026,370 A | 6/1991 | Lottick |
| 5,026,371 A | 6/1991 | Rydell et al. |
| 5,035,696 A | 7/1991 | Rydell |
| 5,038,109 A | 8/1991 | Goble et al. |
| 5,047,026 A | 9/1991 | Rydell |
| 5,047,027 A | 9/1991 | Rydell |
| 5,052,402 A | 10/1991 | Bencini et al. |
| 5,057,107 A | 10/1991 | Parins et al. |
| 5,061,269 A | 10/1991 | Muller |
| 5,062,031 A | 10/1991 | Flachenecker et al. |
| 5,071,419 A | 12/1991 | Rydell et al. |
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |
| 5,116,332 A | 5/1992 | Lottick |
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Klicek et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hovven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen |
| 5,403,312 A | 4/1995 | Yates et al. |
| 5,403,342 A | 4/1995 | Tovey et al. |
| 5,405,344 A | 4/1995 | Willaimson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Hutema et al. |
| 5,509,916 A | 4/1996 | Taylor et al. |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler et al. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |

(56) References Cited

U.S. PATENT DOCUMENTS

| | | |
|---|---|---|
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |
| 5,665,100 A | 9/1997 | Yoon |
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,293 A | 2/1998 | Quinn et al. |
| 5,720,742 A | 2/1998 | Zacharias |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | Dimatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenbergr |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |

(56) References Cited

U.S. PATENT DOCUMENTS

| | | |
|---|---|---|
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble et al. |
| 6,039,736 A | 3/2000 | Platt, Jr. |
| 6,050,996 A | 4/2000 | Schmaltz et al. |
| 6,051,010 A | 4/2000 | Dimatteo et al. |
| 6,053,172 A | 4/2000 | Hovda et al. |
| 6,053,914 A | 4/2000 | Eggers et al. |
| 6,056,746 A | 5/2000 | Goble et al. |
| 6,063,050 A | 5/2000 | Manna et al. |
| 6,063,075 A | 5/2000 | Mohori |
| 6,063,081 A | 5/2000 | Mulier et al. |
| 6,063,086 A | 5/2000 | Benecke et al. |
| 6,066,139 A | 5/2000 | Ryan et al. |
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Huitema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wrublewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Goble et al. |
| 6,237,604 B1 | 5/2001 | Burnside et al. |
| 6,238,366 B1 | 5/2001 | Savage et al. |
| 6,238,392 B1 | 5/2001 | Long |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,550 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble et al. |
| 6,348,051 B1 | 2/2002 | Farin et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Goble et al. |
| 6,364,879 B1 | 4/2002 | Chen et al. |
| 6,371,967 B1 | 4/2002 | Long et al. |
| D457,958 S | 5/2002 | Dycus |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse et al. |
| 6,398,781 B1 | 6/2002 | Goble et al. |
| 6,402,741 B1 | 6/2002 | Keppel et al. |

(56) References Cited

U.S. PATENT DOCUMENTS

| | | |
|---|---|---|
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze et al. |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |
| 6,458,078 B1 | 10/2002 | Luedtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shaoeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B2 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckai et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli et al. |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 * | 6/2004 | Buysse ............ A61B 18/1442 606/49 |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |

(56) References Cited

U.S. PATENT DOCUMENTS

| | | |
|---|---|---|
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoy et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soll et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban et al. |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell |
| 7,041,096 B2 | 5/2006 | Malis |
| 7,041,102 B2 | 5/2006 | Truckai et al. |
| 7,044,948 B2 | 5/2006 | Keppel |
| 7,044,949 B2 | 5/2006 | Orszulak |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich |
| 7,150,748 B2 | 12/2006 | Ebbutt |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |

(56) References Cited

U.S. PATENT DOCUMENTS

| | | |
|---|---|---|
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey |
| 7,169,145 B2 | 1/2007 | Isaacson |
| 7,169,146 B2 | 1/2007 | Truckai et al. |
| 7,172,591 B2 | 2/2007 | Harano et al. |
| 7,179,254 B2 | 2/2007 | Pendkanti |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah |
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble |
| 7,214,224 B2 | 5/2007 | Goble |
| 7,216,001 B2 | 5/2007 | Hacker et al. |
| 7,220,260 B2 | 5/2007 | Fleming |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida |
| 7,229,307 B2 | 6/2007 | Ehr et al. |
| 7,232,439 B2 | 6/2007 | Ciarrocca |
| 7,232,440 B2 | 6/2007 | Dumbald et al. |
| 7,235,048 B2 | 6/2007 | Rein et al. |
| 7,235,072 B2 | 6/2007 | Sartor et al. |
| 7,235,073 B2 | 6/2007 | Levine et al. |
| 7,237,708 B1 | 7/2007 | Guy |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanake et al. |
| 7,354,435 B2 | 4/2008 | Farin et al. |
| 7,354,440 B2 | 4/2008 | Truckai et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Miller et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton |
| 7,416,437 B2 | 8/2008 | Sartor et al. |
| 7,419,487 B2 | 9/2008 | Johnson et al. |
| 7,422,139 B2 | 9/2008 | Shelton et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kuhner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs |
| 7,442,193 B2 | 10/2008 | Shields |
| 7,442,194 B2 | 10/2008 | Dumbauld |
| 7,445,621 B2 | 11/2008 | Dumbauld et al. |
| 7,458,972 B2 | 12/2008 | Keppel |
| 7,464,846 B2 | 12/2008 | Shelton et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |
| 7,491,199 B2 | 2/2009 | Goble et al. |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 2001/0037110 A1 | 11/2001 | Schmaltz |
| 2001/0039417 A1 | 11/2001 | Harano et al. |
| 2002/0052599 A1 | 5/2002 | Goble |
| 2002/0115997 A1 | 8/2002 | Truckai |
| 2002/0120262 A1 | 8/2002 | Bek |
| 2002/0120266 A1 | 8/2002 | Truckai |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham |
| 2003/0014052 A1 | 1/2003 | Buysse |
| 2003/0065327 A1 | 4/2003 | Wellman |
| 2003/0065358 A1 | 4/2003 | Frecker et al. |
| 2003/0069571 A1 | 4/2003 | Treat |
| 2003/0109871 A1 | 6/2003 | Johnson |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus |
| 2003/0199863 A1 | 10/2003 | Swanson et al. |

(56) References Cited

U.S. PATENT DOCUMENTS

| | | |
|---|---|---|
| 2003/0199870 A1 | 10/2003 | Truckai |
| 2003/0229344 A1 | 12/2003 | Dycus et al. |
| 2003/0236549 A1 | 12/2003 | Bonadio et al. |
| 2004/0006340 A1 | 1/2004 | Latterell |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis |
| 2004/0092922 A1 | 5/2004 | Kadziauskas et al. |
| 2004/0122423 A1 | 6/2004 | Dycus |
| 2004/0162557 A1 | 8/2004 | Tetzlaff et al. |
| 2004/0193148 A1 | 9/2004 | Wham |
| 2004/0215127 A1 | 10/2004 | Kadziauskas et al. |
| 2004/0225288 A1 | 11/2004 | Buysse |
| 2004/0250419 A1 | 12/2004 | Sremich |
| 2005/0004563 A1 | 1/2005 | Racz et al. |
| 2005/0004564 A1 | 1/2005 | Wham et al. |
| 2005/0021027 A1 | 1/2005 | Shields et al. |
| 2005/0033282 A1 | 2/2005 | Hooven |
| 2005/0033352 A1 | 2/2005 | Zepf |
| 2005/0080319 A1 | 4/2005 | Dinkler, II et al. |
| 2005/0090815 A1 | 4/2005 | Francischelli et al. |
| 2005/0096681 A1 | 5/2005 | Desinger et al. |
| 2005/0101951 A1 | 5/2005 | Wham |
| 2005/0107785 A1 | 5/2005 | Dycus |
| 2005/0113817 A1 | 5/2005 | Isaacson |
| 2005/0113819 A1 | 5/2005 | Wham et al. |
| 2005/0124915 A1 | 6/2005 | Eggers et al. |
| 2005/0137592 A1 | 6/2005 | Nguyen et al. |
| 2005/0149017 A1 | 7/2005 | Dycus |
| 2005/0159745 A1 | 7/2005 | Truckai |
| 2005/0165444 A1 | 7/2005 | Hart |
| 2005/0192568 A1 | 9/2005 | Truckai et al. |
| 2005/0203504 A1 | 9/2005 | Wham |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079788 A1 | 4/2006 | Anderson et al. |
| 2006/0079878 A1 | 4/2006 | Houser |
| 2006/0129146 A1 | 6/2006 | Dycus |
| 2006/0161190 A1 | 7/2006 | Gadberry et al. |
| 2006/0167450 A1 | 7/2006 | Johnson |
| 2006/0173453 A1 | 8/2006 | Gruhl |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom |
| 2006/0247498 A1 | 11/2006 | Bonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus |
| 2007/0142834 A1 | 6/2007 | Dumbauld |
| 2007/0156139 A1 | 7/2007 | Schecter |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lishinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D' Amelio et al. |
| 2008/0167651 A1 | 7/2008 | Tetzlaff et al. |
| 2008/0172048 A1 | 7/2008 | Martin |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darin et al. |
| 2009/0012520 A1 | 1/2009 | Hixson et al. |
| 2009/0024126 A1 | 1/2009 | Artale |
| 2009/0248007 A1* | 10/2009 | Falkenstein ........ A61B 18/1442 606/33 |
| 2009/0275490 A1 | 11/2009 | Milne et al. |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0138101 A1 | 5/2013 | Kerr |
| 2013/0274743 A1 | 10/2013 | Banfalvi |
| 2013/0296843 A1 | 11/2013 | Boudreqx et al. |
| 2014/0005658 A1 | 1/2014 | Rosenbegr |
| 2014/0088583 A1 | 3/2014 | Singh |
| 2014/0214019 A1 | 7/2014 | Baxter, III et al. |

FOREIGN PATENT DOCUMENTS

| | | |
|---|---|---|
| DE | 10 2005 044 918 A1 | 2/2007 |
| EP | 0 315 338 A1 | 5/1989 |
| EP | 0 538 984 A2 | 4/1993 |
| EP | 0 570 675 B1 | 11/1993 |
| EP | 0 598 202 B1 | 5/1994 |
| EP | 0 717 967 A2 | 6/1996 |
| EP | 0 737 447 A1 | 10/1996 |
| EP | 0 878 168 A1 | 11/1998 |
| EP | 1 054 637 B1 | 11/2000 |
| EP | 1 535 581 A2 | 6/2005 |
| EP | 1 545 361 B1 | 6/2005 |
| EP | 1 557 129 A1 | 7/2005 |
| EP | 1 634 539 A1 | 3/2006 |
| EP | 1 728 475 A2 | 12/2006 |
| EP | 1 810 628 A1 | 7/2007 |
| EP | 1 634 539 B1 | 2/2008 |
| EP | 1 665 995 A1 | 2/2008 |
| EP | 1 946 715 A1 | 7/2008 |
| EP | 2 106 762 A1 | 7/2009 |
| EP | 2 111 812 A2 | 10/2009 |
| EP | 2 156 802 A2 | 2/2010 |
| EP | 2 436 330 A1 | 4/2012 |
| GB | 2 157 175 A | 10/1985 |
| GB | 2 462 453 A | 8/2008 |
| JP | 60-30946 A | 2/1994 |
| JP | 83-17935 A | 12/1996 |
| JP | 11-070123 A | 3/1999 |
| JP | 11-070124 A | 3/1999 |
| JP | 11-178833 A | 7/1999 |

(56) References Cited

FOREIGN PATENT DOCUMENTS

| | | | |
|---|---|---|---|
| JP | 2000-254135 A | 9/2000 | |
| JP | 2003-135481 A | 5/2003 | |
| JP | 2003-164463 A | 6/2003 | |
| JP | 2006-109945 A | 4/2006 | |
| JP | 2006-167403 A | 6/2006 | |
| JP | 2007-144201 A | 6/2007 | |
| JP | 2007-195980 A | 8/2007 | |
| JP | 2007-195985 A | 8/2007 | |
| JP | 2008-043789 A | 2/2008 | |
| JP | 2008-259864 A | 10/2008 | |
| WO | WO 93/015662 A1 | 8/1993 | |
| WO | WO 97/010764 A1 | 3/1997 | |
| WO | WO 99/040857 A1 | 8/1999 | |
| WO | WO 01/012090 A1 | 2/2001 | |
| WO | WO 2004/030553 A1 | 4/2004 | |
| WO | WO 2004/032776 A1 | 4/2004 | |
| WO | WO 2004/032777 A1 | 4/2004 | |
| WO | WO 2004/082495 A1 | 9/2004 | |
| WO | WO 2005/004735 A1 | 1/2005 | |
| WO | WO 05/053785 A2 | 6/2005 | |
| WO | WO 2006/119245 A2 | 11/2006 | |
| WO | WO 2006/125558 A1 | 11/2006 | |
| WO | WO 2007/142601 A1 | 12/2007 | |
| WO | WO 2008/147773 A1 | 12/2008 | |
| WO | WO 2009/065140 A1 | 5/2009 | |
| WO | WO 2012/110996 A2 | 8/2012 | |
| WO | WO2012110996 * | 8/2012 | ............... A61N 5/10 |
| WO | WO 2013/030349 A1 | 3/2013 | |

OTHER PUBLICATIONS

US Patent Application No. PCT/US09/39046 filed Mar. 31, 2009, entitled Electrosurgical System.
European Patent Office, European Search Report for European Patent Application No. 12151288, dated Feb. 10, 2012, 8 pgs.
European Patent Office, Supplementary European Search Report for European Patent Application No. 08755322, dated Apr. 18, 2012, 3 pgs.
European Patent Office, Supplementary European Search Report for European Patent Application No. 08755322, dated Jun. 6, 2012, 2 pgs.
U.S. Appl. No. 12/416,751, filed Apr. 1, 2009, entitled Electrosurgical System, now U.S. Pat. No. 8,579,894 issued Nov. 12, 2013.
European Patent Office, Partial European Search Report for European Patent Application No. 15151398.3, dated Jun. 22, 2015, 9 pgs.
European Patent Office, European Search Report for European Patent Application No. EP 14199708.0, entitled "Electrosurgical System," dated Jul. 10, 2015, 14 pgs.
International Searching Authority/US, The International Search Report and the Written Opinion for International Application No. PCT/US2015/066473 titled "Bipolar Electrosurgical Sealer and Divider." dated Mar. 31, 2016, 13 pgs.
International Searching Authority/US, The International Search Report and the Written Opinion for International Application No. PCT/US2015/033546 titled "Electrosurgical Seal and Dissection Systems." dated Apr. 22, 2016, 31 pgs.
The International Bureau of WIPO, The International Preliminary Report on Patentability for International Application No. PCT/US2015/031452, entitled Electrosurgical System dated Dec. 1, 2016, 21 pgs.

International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System", dated Jul. 27, 2009.
International Preliminary Examining Authority/US, International Preliminary Report on Patentability for International Application No. PCT/US09/39046, titled "Electrosurgical System", dated Mar. 26, 2010.
European Patent Office, European Search Report for European Application No. EP 10 19 2593 dated Mar. 21, 2011, titled Electrosurgical System.
European Patent Office, European Search Report for European Application No. EP 10 19 2614 dated Apr. 18, 2011, titled Electrosurgical System.
European Patent Office, Extended European Search Report for European Application No. EP 10 19 2580 dated Jul. 21, 2011.
International Preliminary Examining Authority/US, International Preliminary Report on Patentability for International Application No. PCT/US09/39046, titled "Electrosurgical System", dated Jan. 17, 2012.
European Patent Office, The International Search Report and Written Opinion of the International Searching Authority for International Application No. PCT/US2011/054661, dated Mar. 6, 2012.
International Searching Authority/US, The International Search Report and the Written Opinion for International Application No. PCT/US09/39046 titled "Electrosurgical System", dated Jun. 2, 2012.
U.S. Appl. No. 12/611,352, filed Nov. 3, 2009, titled Tissue Fusion/Welder Apparatus and Method.
U.S. Appl. No. 12/183,970, filed Jul. 31, 2008, entitled Bipolar Electrosurgical Scissors.
U.S. Appl. No. 12/416,128, filed Mar. 31, 2009, entitled Electrosurgical System.
U.S. Appl. No. 12/416,668, filed Apr. 1, 2009, entitled Electrosurgical System.
U.S. Appl. No. 12/416,695, filed Apr. 1, 2009, entitled Electrosurgical System.
U.S. Appl. No. 12/416,765, filed Apr. 1, 2009, entitled Electrosurgical System.
The International Bureau of WIPO, The International Preliminary Report on Patentability for International Application No. PCT/US2011/054661, entitled Electrosurgical Instruments and Connections Thereto dated Apr. 2, 2013.
European Patent Office, European Search Report for European Application No. EP 13 17 4814.7 dated Sep. 30, 2013, titled Electrosurgical System.
International Searching Authority/US, The International Search Report and the Written Opinion for International Application No. PCT/US2015/031452 titled "Electrosurgical Fusion Device", dated Dec. 3, 2015.

* cited by examiner

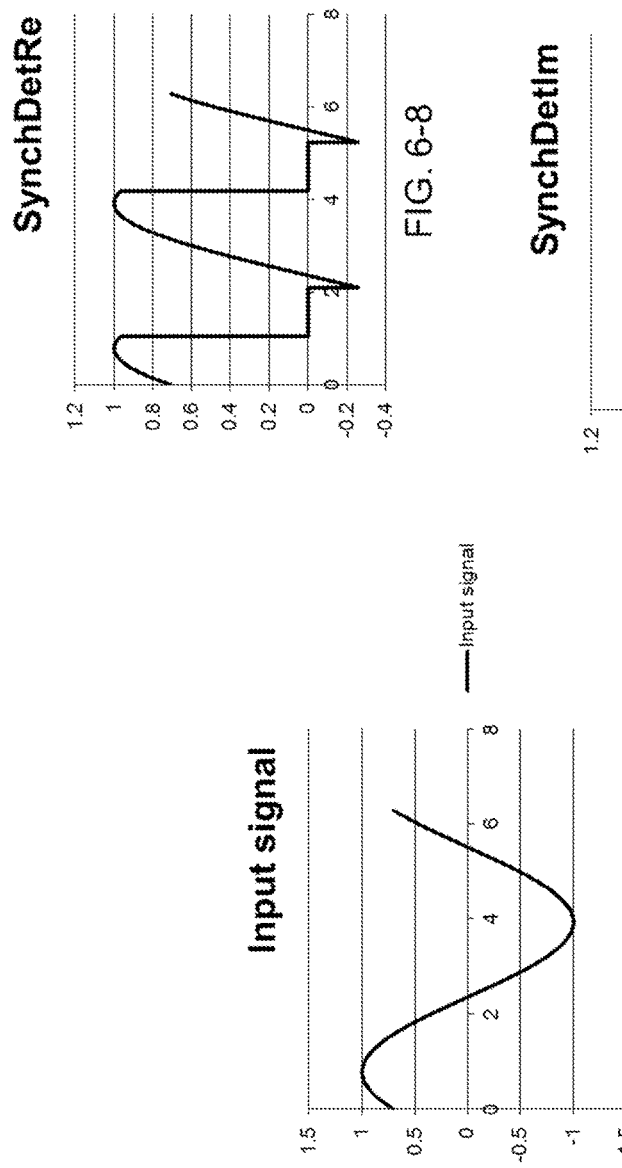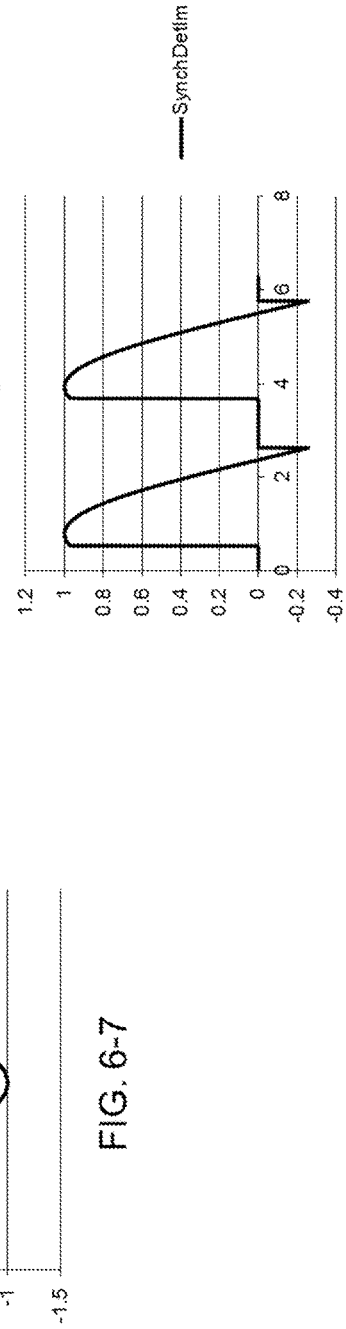
FIG. 6-8
FIG. 6-9
FIG. 6-7

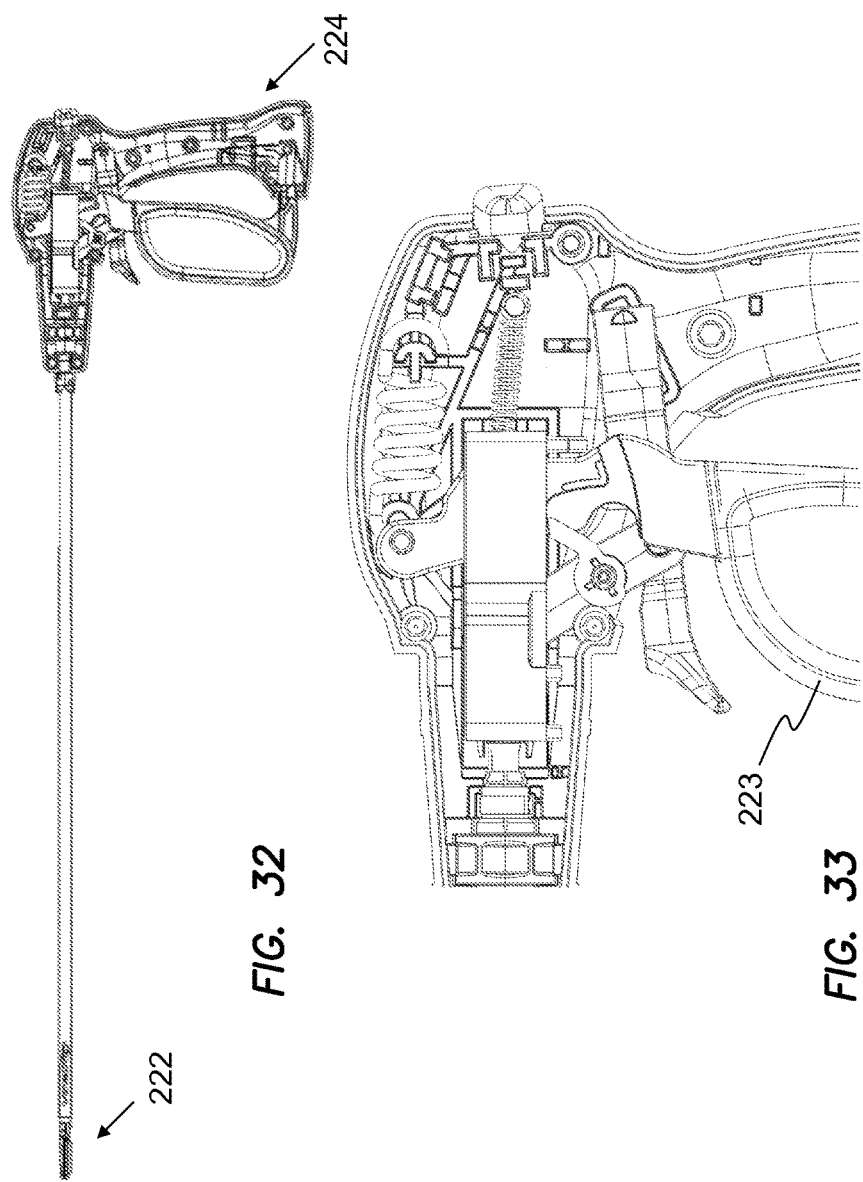

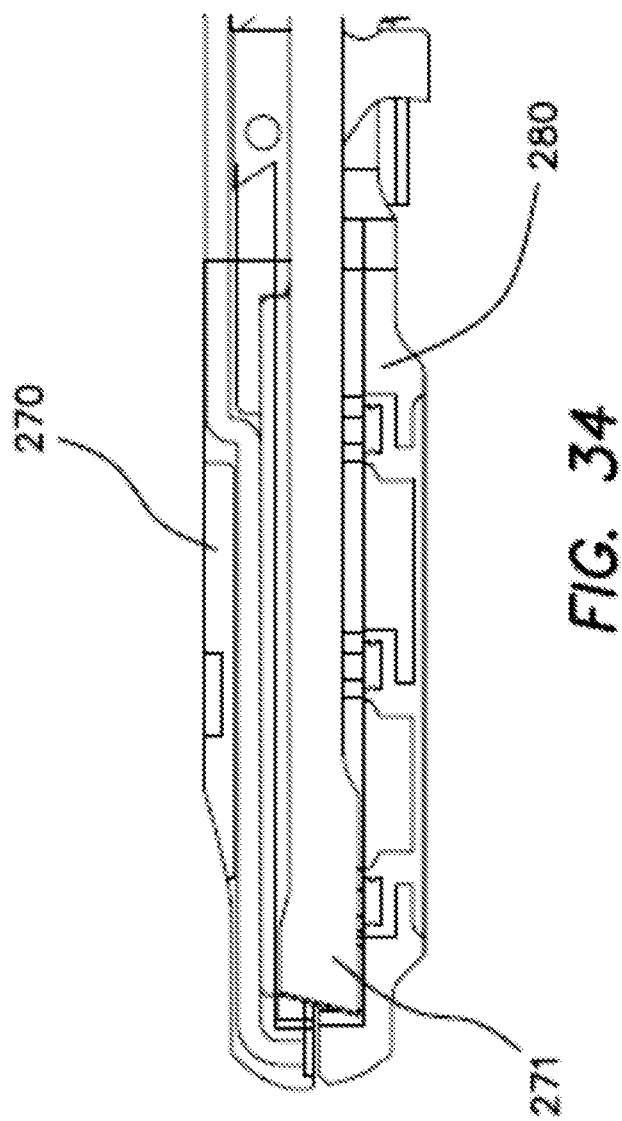

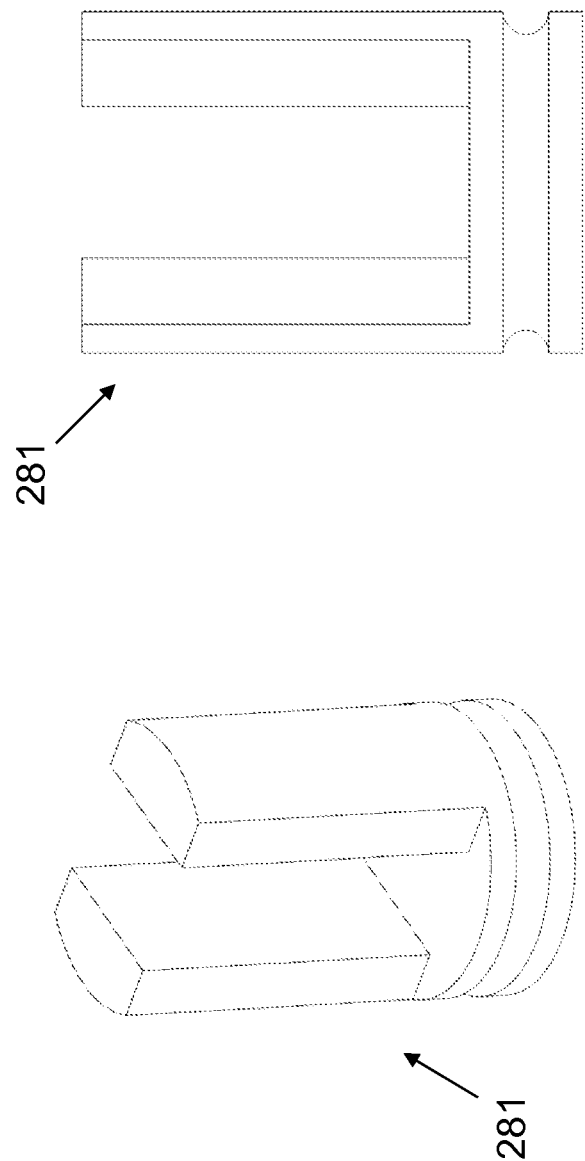

ELECTROSURGICAL SYSTEM

CROSS-REFERENCE TO RELATED APPLICATIONS

This is application is a continuation of International Application No. PCT/US2015/031452, filed May 18, 2015, which claims the benefit of U.S. Provisional Application No. 61/994,192, filed on May 16, 2014; U.S. Provisional Application No. 61/994,185, filed on May 16, 2014; U.S. Provisional Application No. 61/994,415, filed on May 16, 2014; and U.S. Provisional Application No. 61/994,215, filed May 16, 2014, the entire disclosures of which are incorporated by reference as if set forth in full herein.

BACKGROUND

The present application relates generally to electrosurgical systems and methods and more particularly relates to electrosurgical generators and advanced bipolar electrosurgical devices or instruments.

Electrosurgical devices or instruments have become available that use electrical energy to perform certain surgical tasks. Typically, electrosurgical instruments are hand tools such as graspers, scissors, tweezers, blades, needles, and other hand tools that include one or more electrodes that are configured to be supplied with electrical energy from an electrosurgical generator including a power supply. The electrical energy can be used to coagulate, fuse, or cut tissue to which it is applied.

Electrosurgical instruments typically fall within two classifications: monopolar and bipolar. In monopolar instruments, electrical energy is supplied to one or more electrodes on the instrument with high current density while a separate return electrode is electrically coupled to a patient and is often designed to minimize current density. Monopolar electrosurgical instruments can be useful in certain procedures, but can include a risk of certain types of patient injuries such as electrical burns often at least partially attributable to functioning of the return electrode. In bipolar electrosurgical instruments, one or more electrodes is electrically coupled to a source of electrical energy of a first polarity and one or more other electrodes is electrically coupled to a source of electrical energy of a second polarity opposite the first polarity. Thus, bipolar electrosurgical instruments, which operate without separate return electrodes, can deliver electrical signals to a focused tissue area with reduced risks.

Even with the relatively focused surgical effects of bipolar electrosurgical instruments, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired coagulation or cutting effect upon the application of electrical energy varies based on the tissue type and can also vary based on pressure applied to the tissue by an electrosurgical instrument. However, even for a highly experienced surgeon, it can be difficult for a surgeon to assess how quickly a mass of combined tissue types grasped in an electrosurgical instrument will be fused a desirable amount.

Attempts have been made to reduce the risk of tissue damage during electrosurgical procedures. For example, previous electrosurgical systems have included generators that monitor an ohmic resistance or tissue temperature during the electrosurgical procedure, and terminated electrical energy once a predetermined point was reached. However, these systems have had shortcomings in that they can provide inconsistent results at determining tissue coagulation, fusion, or cutting endpoints for varied tissue types or combined tissue masses. These systems can also fail to provide consistent electrosurgical results among use of different instruments having different instrument and electrode geometries. Typically, even where the change is a relatively minor upgrade to instrument geometry during a product's lifespan, the electrosurgical generator must be recalibrated for each instrument type to be used, a costly, time consuming procedure which can undesirably remove an electrosurgical generator from service.

SUMMARY

In certain embodiments, an electrosurgical system for performing electrosurgical procedures on body tissue of a patient comprises an electrosurgical generator and a bipolar electrosurgical device or instrument. The generator controls the delivery of electrosurgical energy to fuse tissue in contact with the bipolar electrosurgical device. The generator in various embodiments identifies a phase zero crossing, adjusts the RF energy output or voltage and measures and monitors a phase angle and/or a change of phase angle rate relative to a predetermined threshold with the predetermined threshold identified at the identified phase zero crossing.

In accordance with various embodiments, an electrosurgical fusion device comprises first jaw coupled to a second jaw with the first jaw having a first electrode and the second jaw having a second electrode facing the first electrode. The first and second electrodes are arranged to conduct radio frequency (RF) energy between the first and second electrodes and the first and second electrodes are made of the same conductive material. The electrosurgical fusion device also includes an elongate shaft having a proximal end and a distal end and a longitudinal axis extending from the proximal end to the distal end, the first and second jaws being pivotably coupled to the distal end of the elongate shaft. The elongate shaft in one embodiment has an outer diameter of less than 5 mm to fit through a 5 mm cannula.

In accordance with various embodiments, the electrosurgical fusion device comprises a conductive post incorporated into the second jaw and extending from the second jaw towards the first jaw. The conductive post is stationary and is made of the same conductive material as the first and second electrodes. In various embodiments, the conductive post includes a plurality of conductive posts having varying heights.

In accordance with various embodiments, the electrosurgical fusion device comprises a first jaw having a conductive pad with a second jaw coupled to the first jaw. The second jaw having an inner surface facing the conductive pad with the first and second jaws arranged to capture tissue between the conductive pad and the inner surface of the second jaw. The conductive pad and the second jaw are arranged to connect to an electrosurgical energy source and arranged to conduct RF energy through tissue held between the jaws. The electrosurgical fusion device also comprises a blade movable along a longitudinal axis from a proximal position to a distal position and back to the proximal position with the blade disposed within an outer periphery of the second jaw.

In accordance with various embodiments, the electrosurgical fusion device comprises a conductive post disposed on the second jaw and adjacent to the blade. The conductive post is arranged to not connect to the electrosurgical energy source and is arranged to conduct RF energy between the conductive pad or the second jaw through the tissue held between the jaws.

Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

FIGS. 4-1 to 4-2 are schematic block diagrams of an embodiment of electrosurgical system.

FIG. 6-1 is a schematic block diagram of portions of an electrosurgical system in accordance with various embodiments of the present invention.

FIG. 6-2 is a signal diagram illustrating operations of an electrosurgical system in accordance with various embodiments of the present invention.

FIG. 6-3 is a schematic block diagram of portions of an electrosurgical system in accordance with various embodiments of the present invention.

FIGS. 6-4 to 6-12 are signal diagrams illustrating operations of an electrosurgical system in accordance with various embodiments of the present invention.

FIGS. 7 to 9 are schematic block diagrams of portions of an electrosurgical system in accordance with various embodiments of the present invention.

FIG. 10 is a flow chart illustrating operations of an electrosurgical system in accordance with various embodiments of the present invention.

FIGS. 12-20 are graphical representations of exemplary data or results provided by an electrosurgical system in accordance with various embodiments of the present invention.

FIG. 32 is a side cross-sectional view of an electrosurgical device in accordance with various embodiments of the present invention.

FIG. 33 is a side cross-sectional view of a portion of an actuator of an electrosurgical device in accordance with various embodiments of the present invention.

FIG. 34 is a side cross-sectional view of a distal end of an electrosurgical device in accordance with various embodiments of the present invention.

FIG. 36 is a perspective view of a post in accordance with various embodiments of the present invention.

FIG. 37 is a side view of a post in accordance with various embodiments of the present invention.

DETAILED DESCRIPTION

Figure 1:
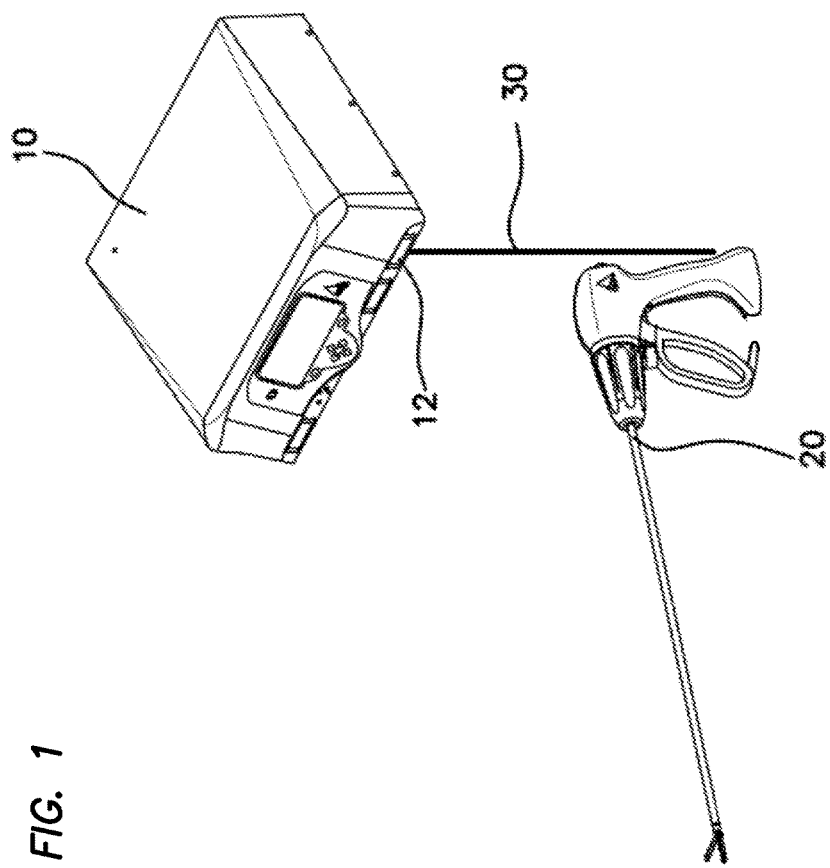
FIG. 1 is a perspective view of an electrosurgical system in accordance with various embodiments of the present invention.

In accordance with various embodiments, an electrosurgical system is provided that includes an electrosurgical generator and an electrosurgical instrument that are configured to optimally fuse tissue. The electrosurgical instrument in accordance with various embodiments is provided to be used in laparoscopic surgery with the ability to move, grasp and compress tissue and to deliver RF energy to fuse the tissue. In accordance with various embodiments, the electrosurgical instrument is a bipolar electrosurgical instrument insertable through a 5 mm trocar and cuts tissue through actuation of a mechanical cutting blade. The RF energy is supplied by the electrosurgical generator configured to provide the appropriate RF energy to fuse the tissue. The generator in accordance with various embodiments determines the appropriate RF energy and the appropriate manner to deliver the RF energy for the particular connected electrosurgical instrument, the particular tissue in contact with the instrument and/or a particular surgical procedure. In accordance with various embodiments, information or data to assist in the determination of the appropriate RF energy and manner to deliver the RF energy is supplied or obtained externally from the generator. The external source in various embodiments is one or more memory modules that may be included with the electrosurgical instrument or via connections therebetween (wired or wireless) or via a separate tool, accessory and/or adapter and/or connections therebetween and/or via a separate port or connection to the generator. The generator retrieves and/or receives the data and utilizes the data to command or operate the generator to determine and supply the appropriate RF energy in the appropriate manner.

Generally, in accordance with various embodiments, a bipolar electrosurgical fusion instrument or tool is provided that is arranged to fuse tissue captured between jaws. The jaws extend from an elongate shaft coupled to an actuator. The actuator is user accessible by which a user can manipulate the jaws to open and close the jaws and change their orientation or position. A user through the actuator can also initiate fusion of issue in contact with the jaws. The jaws in various embodiments includes an electrode on each jaw that are capable of being connected to an electrosurgical energy source, such as an electrosurgical generator, to conduct radio frequency (RF) energy therebetween and the tissue captured between the jaws. A movable blade is also provided to cut tissue captured between the jaws. In accordance with various embodiments, at least one jaw includes at least one conductive post that is positioned between the blade and an electrode of that jaw. The conductive post is made of the same conductive material as the electrodes of the jaws, but unlike the electrodes is not connected or capable of being connected to an electrosurgical generator to conduct RF energy therebetween. The conductive post however in accordance with various embodiments may participate in conducting electrosurgical energy between the jaws and the tissue therebetween.

Figure 2:
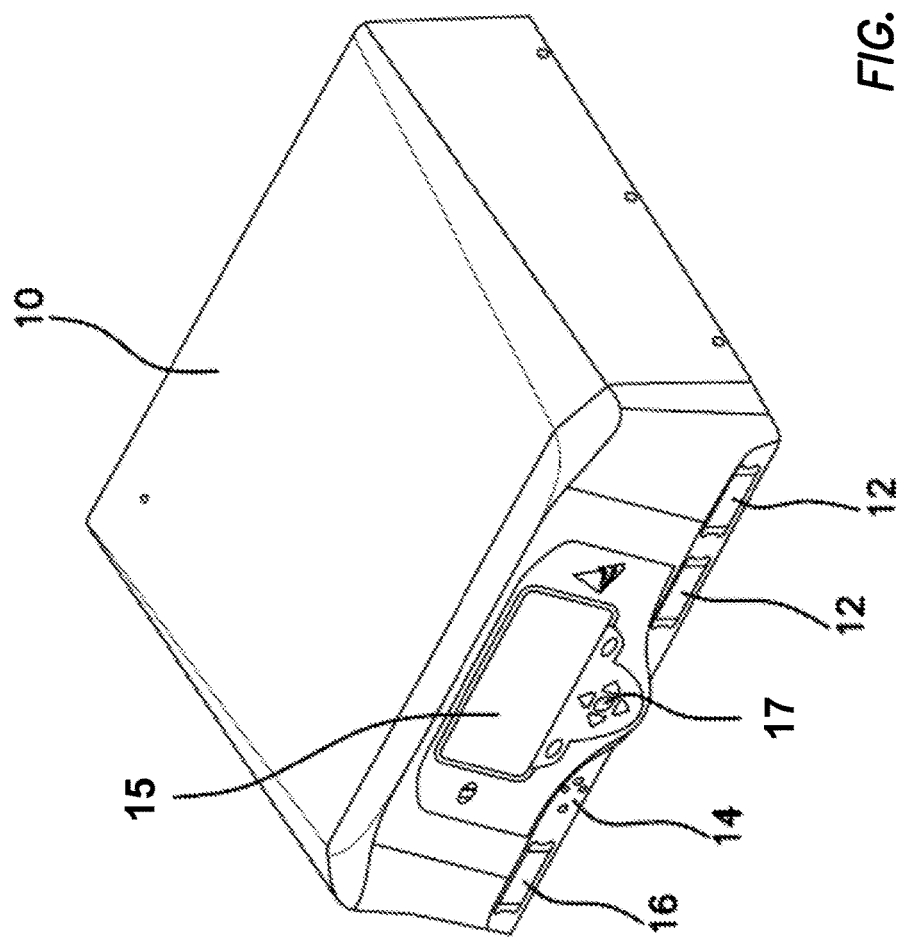
FIG. 2 is a perspective view of an electrosurgical generator in accordance with various embodiments of the present invention.

Referring to FIGS. 1-2, an exemplary embodiment of electrosurgical system is illustrated including an electrosurgical generator 10 and a removably connectable electrosurgical instrument 20. The electrosurgical instrument 20 can be electrically coupled to the generator via a cabled connection 30 to a tool or device port 12 on the generator. The electrosurgical instrument 20 may include audio, tactile and/or visual indicators to apprise a user of a particular predetermined status of the instrument such as a start and/or end of a fusion or cut operation. In other embodiments, the electrosurgical instrument 20 can be reusable and/or connectable to another electrosurgical generator for another surgical procedure. In some embodiments, a manual controller such as a hand or foot switch can be connectable to the generator and/or instrument to allow predetermined selective control of the instrument such as to commence a fusion or cut operation.

In accordance with various embodiments, the electrosurgical generator 10 is configured to generate radiofrequency (RF) electrosurgical energy and to receive data or information from the electrosurgical instrument 20 electrically coupled to the generator. The generator 10 in one embodiment outputs RF energy (375 VA, 150V, 5 A at 350 kHz) and in one embodiment is configured to calculate a phase angle or difference between RF output voltage and RF output current during activation or supply of RF energy. The generator regulates voltage, current and/or power and monitors RF energy output (e.g., voltage, current, power and/or phase). In one embodiment, the generator 10 stops RF energy output under predefine conditions such as when a device switch is de-asserted (e.g., fuse button released), a time value is met, and/or active phase angle and/or change of phase is greater than or equal to a phase and/or change of phase stop value.

The electrosurgical generator 10 comprises two advanced bipolar tool ports 12, a standard bipolar tool port 16, and an electrical power port 14. In other embodiments, electrosurgical units can comprise different numbers of ports. For example, in some embodiments, an electrosurgical generator can comprise more or fewer than two advanced bipolar tool ports, more or fewer than the standard bipolar tool port, and more or fewer than the power port. In one embodiment, the electrosurgical generator comprises only two advanced bipolar tool ports.

In accordance with various embodiments, each advanced bipolar tool port 12 is configured to be coupled to electrosurgical instrument having an attached or integrated memory module. The standard bipolar tool port 16 is configured to receive a non-specialized bipolar electrosurgical tool that differs from the advanced bipolar electrosurgical instrument connectable to the advanced bipolar tool port 12. The electrical power port 14 is configured to receive or be connected to a direct current (DC) accessory device that differs from the non-specialized bipolar electrosurgical tool and the advanced electrosurgical instrument. The electrical power port 14 is configured to supply direct current voltage. For example, in some embodiments, the power port 14 can provide approximately 12 Volts DC. The power port 14 can be configured to power a surgical accessory, such as a respirator, pump, light, or another surgical accessory. Thus, in addition to replacing electrosurgical generator for standard or non-specialized bipolar tools, the electrosurgical generator can also replace a surgical accessory power supply. In some embodiments, replacing presently-existing generators and power supplies with the electrosurgical generator can reduce the amount of storage space required on storage racks cards or shelves in the number of mains power cords required in a surgical workspace.

In one embodiment, connection of a non-specialized bipolar tool into the standard bipolar port will not cause the generator to actively check the tool. However, the generator recognizes a connection so that the information of the non-specialized bipolar tool can be displayed. In accordance with various embodiments, the generator recognizes device connection status for each of the advanced tool ports 12 and authenticates connected devices before accepting RF energy activation requests (e.g., activation of an instrument switch such as a fuse button). The generator in one embodiment reads authenticated data from the connected device and reads electrical control values (such as but not limited to voltage level settings, current level settings, power level settings, active phase angle level settings, RF energy output activation timing limits, instrument short limits, instrument open limits, instrument model/identification, RF energy output line configurations, switch state command configurations and/or combinations thereof) from the authenticated and connected device.

In accordance with various embodiments, the electrosurgical generator 10 can comprise a display 15. The display can be configured to indicate the status of the electrosurgical system including, among other information, the status of the one or more electrosurgical instruments and/or accessories, connectors or connections thereto. In some embodiments, the display can comprise a multi-line display capable of presenting text and graphical information such as for example an LCD panel display, which, in some embodiments can be illuminated via backlight or sidelight. In some embodiments, the display can comprise a multi-color display that can be configured to display information about a particular instrument electrically coupled to the electrosurgical generator and a color that corresponds to a particular surgical procedure (such as, for example cutting operations displayed in yellow text and graphics, fusion or welding operations displayed in purple, and coagulation displayed in blue, bloodless dissection operations can be displayed in yellow and blue).

In some embodiments, the display can be configured to simultaneously indicate status data for a plurality of instruments electrically coupled to the electrosurgical generator and/or be portioned to display status information for each instrument connected to a corresponding tool port. A visual indicator such as a status bar graph can be used to illustrate a proportion of total available electrical energy to be applied to the bipolar electrosurgical instrument when actuated. In various embodiments, an electrosurgical instrument operable to cut, coagulate, or fuse tissue could have three color-coded displays or bar graphs. In some embodiments, a user can toggle the display between presenting status of multiple electrically connected instruments and status of a single electrically connected instrument. In accordance with various embodiments, once an instrument and/or accessory is connected and/or detected a window opens in the user interface display showing the type of instrument connected and status.

The electrosurgical generator in accordance with various embodiments can comprise a user interface such as, for example a plurality of buttons 17. The buttons can allow user interaction with the electrosurgical generator such as, for example, requesting an increase or decrease in the electrical energy supplied to one or more instruments coupled to the electrosurgical generator. In other embodiments, the display 15 can be a touch screen display thus integrating data display and user interface functionalities. In accordance with various embodiments, through the user interface, the surgeon can set a voltage setting by the selection of one to three levels. For example, at level 1, voltage is set to 110V; at level 2, voltage is set to 100V; and at level 3, voltage is set to 90V. Current is set to 5 Amps and power is set to 300 VA for all three levels. In other embodiments, the voltage is preset or defaults to a specific level such as level 2. In other embodiments, like the current and power settings, the voltage setting is not user adjustable to simplify operation of the generator and as such a predetermined default voltage setting is utilized, e.g., voltage is set to 100V.

In one embodiment, the electrosurgical tool or instrument 20 can further comprise of one or more memory modules. In some embodiments, the memory comprises operational data concerning the instrument and/or other instruments. For example, in some embodiments, the operational data may include information regarding electrode configuration/reconfiguration, the instrument uses, operational time, voltage, power, phase and/or current settings, and/or particular operational states, conditions, scripts, processes or procedures. In one embodiment, the generator initiate reads and/or writes to the memory module.

In one embodiment, each advanced bipolar electrosurgical instrument comes with a memory module and/or an integrated circuit that provides instrument authentication, configuration, expiration, and logging. Connection of such instruments into the receptacles or ports initiates an instrument verification and identification process. Instrument authentication in one embodiment is provided via a challenge-response scheme and/or a stored secret key also shared by the generator. Other parameters have hash keys for integrity checks. Usages are logged to the generator and/or to the instrument integrated circuit and/or memory. Errors in one embodiment can result in unlogged usage. In one embodiment, the log record is set in binary and interpreted with offline instruments or via the generator.

In one embodiment, the generator uses time measurement components to monitor a instrument's expiration. Such components utilize polling oscillators or timers or real-time calendar clocks that are configured at boot time. Timer interrupts are handled by the generator and can be used by scripts for timeout events. Logging also utilizes timers or counters to timestamp logged events.

In accordance with various embodiments, the generator provides the capability to read the phase difference between the voltage and current of the RF energy sent to the connected electrosurgical instrument while RF energy is active. While tissue is being fused, phase readings are used to detect different states during the fuse process.

In one embodiment, the generator logs usage details in an internal log that is down loadable. The generator has memory for storage of code and machine performance. The generator has reprogrammable memory that contains instructions for specific instrument performance. The memory for example retains a serial number and instrument use parameters. The generator stores information on the type of instruments connected. Such information includes but is not limited to an instrument identifier, e.g., a serial number of a connected instrument, along with a time stamp, number of uses or duration of use of the connected instrument, power setting of each and changes made to the default setting. The memory in one embodiment holds data for about two months, about 10,000 instrument uses or up to 150 logged activations and is configured to overwrite itself as needed.

The generator in accordance with various embodiments does not monitor or control current, power or impedance. The generator regulates voltage and can adjust voltage. Electrosurgical power delivered is a function of applied voltage, current and tissue impedance. The generator through the regulation of voltage can affect the electrosurgical power being delivered. However, by increasing or decreasing voltage, delivered electrosurgical power does not necessarily increase or decrease. Power reactions are caused by the power interacting with the tissue or the state of the tissue without any control by a generator other than by the generator supplying power.

The generator once it starts to deliver electrosurgical power does so continuously, e.g., every 150 ms, until a fault occurs or a specific phase parameter is reached. In one example, the jaws of the electrosurgical instrument can be opened and thus compression relieved at any time before, during and after the application of electrosurgical power. The generator in one embodiment also does not pause or wait a particular duration or a predetermined time delay to commence termination of the electrosurgical energy.

Figure 3:
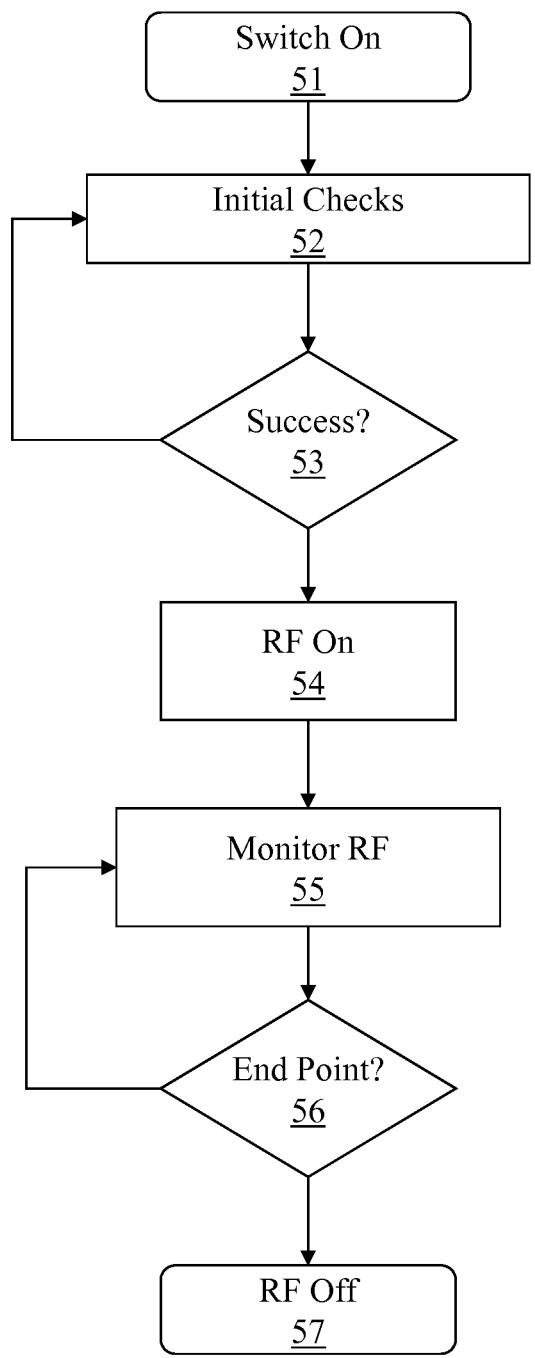
FIG. 3 is a flow chart illustrating operations of an electrosurgical system in accordance with various embodiments of the present invention.

In one embodiment, an electrosurgical process such as a tissue fusion process starts with depressing a switch on the instrument or tool (51), which starts an initial measurement sequence as illustrated in FIG. 3. With engagement of a switch on the tool, the generator takes initial measurements on the tissue (opens, shorts, etc.) (52) and based on the initial measurements initiates or does not initiate the supply of RF energy (53). In accordance with various embodiments, the generator measures tool and/or tissue impedance and/or resistance, and/or if a phase angle is within an acceptable range. In one embodiment, the generator performs a measurement of tissue between the electrodes of an electrosurgical instrument connected to the generator utilizing RF energy with a low energy range (e.g., a voltage about 1-10 Volts) that does not cause a physiological effect (i.e., a passive measurement). In various embodiments, the generator uses the initial impedance measurement to determine if the instrument is shorted, faulty, open and the like. Based on a positive result of the initial check, the generator switches-in a supply of RF energy from the generator to the electrosurgical instrument and ultimately to the tissue (54). After RF power is turned on and is being supplied continuously by the generator, the generator monitors the phase angle or difference and/or change of phase angle between current and voltage of the supplied RF energy (55).

At or upon a predefined point, condition or threshold (56), the supply of RF energy is terminated (57). In this case, an acoustical and/or visual signal is provided indicating that the tissue is fused (or that an error has occurred (e.g., shorting of the electrodes) and/or an unexpected condition has occurred (e.g., permissible although unexpected switch release)). In accordance with various embodiments, the predefined point, condition or threshold and/or initialization checks are determined based on an instrument algorithm or script provided for a connected electrosurgical instrument, procedure or preference. In accordance with various embodiments, the product of measured tissue permittivity and conductivity or an initial phase shift is utilized to determine the end point for a connected instrument.

Figures 1, 4:
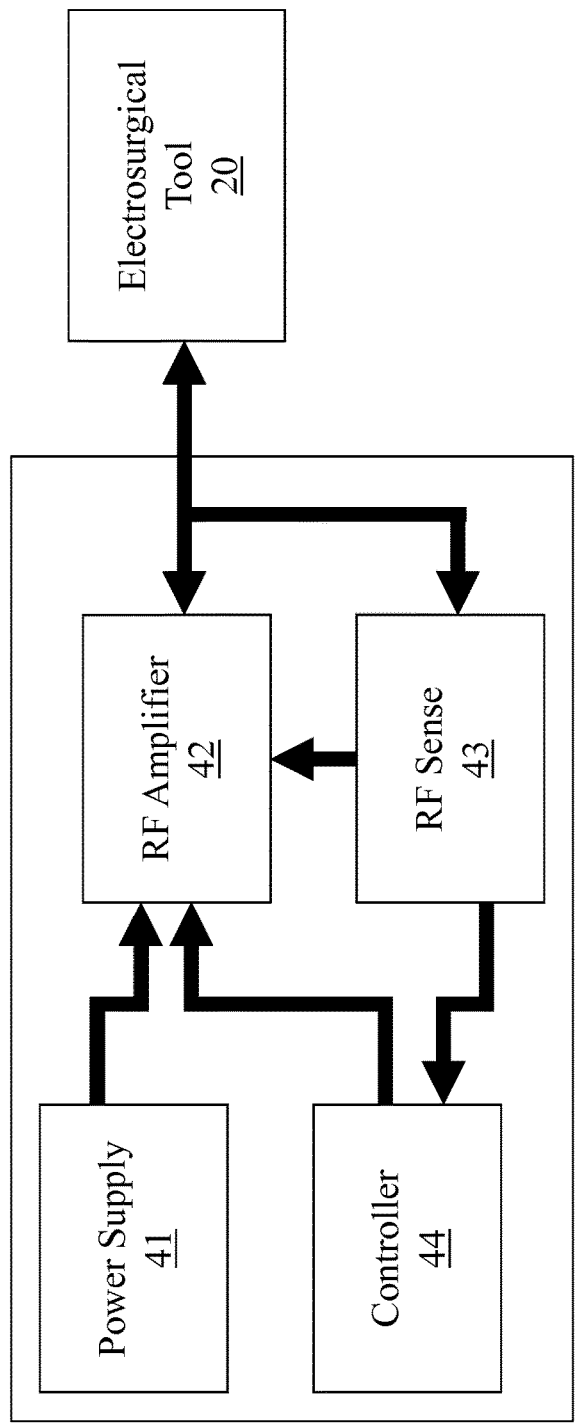
Figures 2, 4:
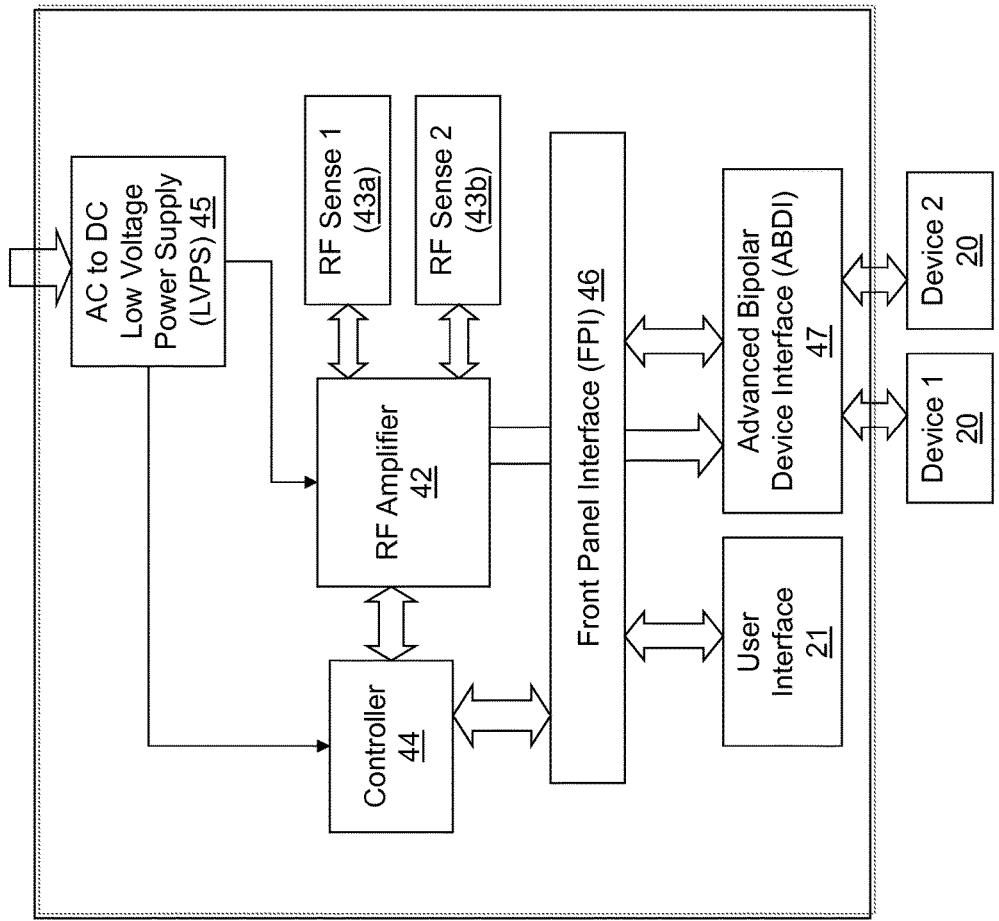

Referring now to FIG. 4-1, in one embodiment, the electrosurgical generator 10 is connected to AC main input and a power supply 41 converts the AC voltage from the AC main input to DC voltages for powering various circuitry of the generator. The power supply also supplies DC voltage to an RF amplifier 42 that generates RF energy. In one embodiment, the RF amplifier 42 converts 100 VDC from the power supply to a sinusoidal waveform with a frequency of 350 kHz which is delivered through a connected electrosurgical instrument. RF sense circuitry 43 measures/calculates voltage, current, power and phase at the output of the generator in which RF energy is supplied to a connected electrosurgical instrument 20. The measured/calculated information is supplied to a controller 44.

In one embodiment, the RF sense analyzes the measured AC voltage and current from the RF amplifier and generates DC signals for control signals including voltage, current, power, and phase that are sent to the controller for further processing. In one embodiment, RF sense circuitry 43 measures the output voltage and current and calculates the root means square (RMS) of the voltage and current, apparent power of the RF output energy and the phase angle between the voltage and current of the RF energy being supplied through a connected electrosurgical instrument. In particular, the voltage and current of the output RF energy are processed by analog circuitry of the RF sense to generate real and imaginary components of both voltage and current. These signals are processed by an FPGA to give different measurements relating to voltage and current, including the RMS measurements of the AC signals, phase shift between voltage and current, and power. Accordingly, in one embodiment, the output voltage and current are measured in analog, converted to digital, processed by an FPGA to calculate RMS voltage and current, apparent power and phase angle between voltage and current, and then are converted back to analog for the controller.

Referring now also to FIG. 4-2, for each device port 45*a*, 45*b* there are a pair of signals for voltage and a pair of signals for current that originate from the RF amplifier 42. In one embodiment, the generator has two redundant RF sense circuits 43*a*, 43*b* that measures voltage and current for each device at different locations on the RF amplifier. The first RF Sense circuit senses current 145*a*, 145*b* by sense resistor 141, 142, delivered through a connected electrosurgical instrument on either device port 1 or device port 2, and the voltage 148*a*, 148*b* measured across return to output on either device port 1 or device port 2. The second RF Sense circuit senses current 147*a*, 147*b* by sense resistor 143, 144, returned from a connected electrosurgical instrument on either device port 1 or device port 2, and the voltage 146*a*, 146*b* measured across output to return on either device port 1 or device port 2. The voltage input signals are high voltage sinusoidal waveforms at 350 kHz that are attenuated and AC coupled by a voltage divider and an inverting filter to remove DC bias on the signals. An inverting filter is used as the voltage and current inputs are 180 degrees out of phase as they are measured at opposite polarities. For each voltage input signal, two separate inverted and non-inverted voltage sense signals are generated. In one embodiment, a differential voltage measurement is made between the current input signals to generate two separate pairs of inverted and non-inverted current sense signals. The current input signals represent voltage across a shunt resistor on the RF Amplifier in which this voltage is proportional to the current flowing through the shunt resistor. The current input signals are low voltage sinusoidal waveforms at 350 kHz that are amplified using a non-inverting filter to remove DC bias on the signals. The RF Sense generates a signal that is analogous to multiplying each voltage and current signal by predetermined reference signals. As such, the RF Sense provides the non-inverted voltage and current sense signals when the waveform is positive, the inverted voltage and current sense signals when the waveform is negative, and a ground signal when the waveform is zero.

The RF sense in accordance with various embodiments receives four reference synchronization signals supplied by the controller via the RF amplifier. The synchronization signals are 350 kHz pulse signals with the same duty cycle but with differing phase shifts and in one embodiment are 90 degrees phase shifted from each other. Two of the synchronization signals are used to generate the in-phase waveforms to generate the real component of the input waveforms and the two other synchronization signals are used to generate the quadrature waveforms to generate the imaginary components of the input waveforms. These signals are processed further to generate control signals to a plurality of switches. The outputs of the switches are tied together to generate a single output. In one embodiment, the control signals to the switches determine which input signal passes through to the single output. In accordance with various embodiments, a first combination allows non-inverted voltage and current sense signals to pass through which represents or is analogous to multiplying these sense signals by a positive pulse. A second combination allows the inverted voltage and current sense signals to pass through which represents or is analogous to multiplying these sense signals by a negative pulse. A third combination allows the ground signal to pass through generating a zero voltage output which represents or is analogous to multiplying the sense signals by zero. Each output is supplied to a low pass filter that generates a DC voltage corresponding to the real or imaginary component of the sensed signals. These signals supplied to ADCs which sends a digital signal to the FPGA.

In one embodiment, Controller 44 controls the RF amplifier 42 to affect the output RF energy. For example, Controller utilizes the information provided by the RF sense 43 to determine if RF energy should be outputted and when to terminate the output of RF energy. In one embodiment, the controller compares a predetermined phase threshold based on a particular tissue in contact with the connected electrosurgical device 20 to determine when to terminate the output of RF energy. In various embodiments, the controller performs a fusion process described in greater detail below and in some embodiments the controller receives the instructions and settings or script data to perform the fusion process from data transmitted from the electrosurgical instrument.

In accordance with various embodiments as shown in FIG. 4-2, the generator has six major sub-systems or modules of circuitry that include System Power or Power Supply 45, Controller 44, Front Panel Interface 46, Advanced Bipolar Device Interface 47, RF Amplifier 42 and RF Sense 43. In accordance with various embodiments, one or more of the circuitry may be combined or incorporated with other circuitry. The Power supply 45 is configured to provide DC voltages to all the other circuitry or sub-systems along with control signals to control the power supply outputs. The power supply receives AC power input that is 90-264 VAC, 47-63 Hz and in one embodiment the power supply has a switch, integrated or separate, that is configured to connect or disconnect the AC power input from the generator. The controller through the Front Panel Interface (FPI) and Advanced Bipolar Device Interface (ABDI) supports the user interface 21 and instrument connections for electrosurgical devices 1 and 2 connected to the electrosurgical generator.

The RF Amplifier 42 generates high power RF energy to be passed through a connected electrosurgical instrument and in one example, an electrosurgical instrument for fusing of tissue. The RF Amplifier in accordance with various embodiments is configured to convert a 100 VDC power source to a high power sinusoidal waveform with a frequency of 350 kHz which is delivered through the ABDI 47 and eventually the connected electrosurgical device. The RF Sense 43 interprets the measured AC voltage and current from the RF amplifier 42 and generates DC control signals, including voltage, current, power, and phase, that is interpreted by Controller 44.

The generator has a plurality of specialized connection receptacles, in the illustrated embodiment device port 1 and device port 2, that are used only for connecting to advanced bipolar devices, such as the electrosurgical fusion instrument described in greater detail below. The specialized receptacles each include an array spring-loaded probes or pogo pins. The generator in various embodiments includes a circuit to detect the presence of an advanced bipolar device prior to energizing any active output terminals at the receptacles.

The Front Panel Interface (FPI) 46 is configured to drive a display, device signals from the controllers and LED backlights for front panel buttons. The FPI is also configured to provide power isolation through regulators and provide functionality for the front panel switches/buttons. In one embodiment, the ABDI 47 is used as a pass-through connection which provides a connection to the devices through the FPI. The FPI also provides connection between Controller 44 and a connected electrosurgical device through the ABDI. The device interface in one embodiment is electrically isolated from the rest of the FPI. The interface in various embodiments includes lines that read and write to an FRAM on an advanced bipolar device, read a trigger switch and/or read a signal that indicates a device is connected. In one embodiment, a device memory circuit is provided that utilizes the controller's SPI interface to read and write the FRAM of the advanced bipolar device. In one embodiment, the FRAM is replaced with a microcontroller and the interface includes an interrupt line so all information passed through a digital interface between the electrosurgical device and the generator. FPI provides isolation for SPI signals to and from advanced bipolar device through ABDI. In one embodiment, the SPI interface is shared between two advanced bipolar devices with port pins being used as chip selects.

In accordance with various embodiments, the generator includes a SPI communication bus that allows the controller to have bi-directional communication with the CPLDs and the RF Sense FPGAs. In various embodiments, the FPI provides SPI interface between the controller and connected devices through an ABDI connector to communicate with the FRAM on the advanced bipolar devices. FPI also provides electrical isolation for low voltage signals from between controller and the ABDI. The device interface on the ABDI is configured to transmit RF energy to the connected device along with SPI communication. In one embodiment, the ABDI connects a signal from a device that indicates it is connected.

The FPI-ABDI interface provides power to the devices that connect to the generator, SPI communication between controller and the devices, device switch signals from the devices to the controller, and device connected signals from the devices to the controller. ABDI provides the RF energy to each connected advanced bipolar device through a separate pogo pin array. The FPI provides signal, low voltage power and high voltage RF power from the FPI and RF Amplifier to the connected device through the ABDI connector via the pogo pin array.

Figure 5:
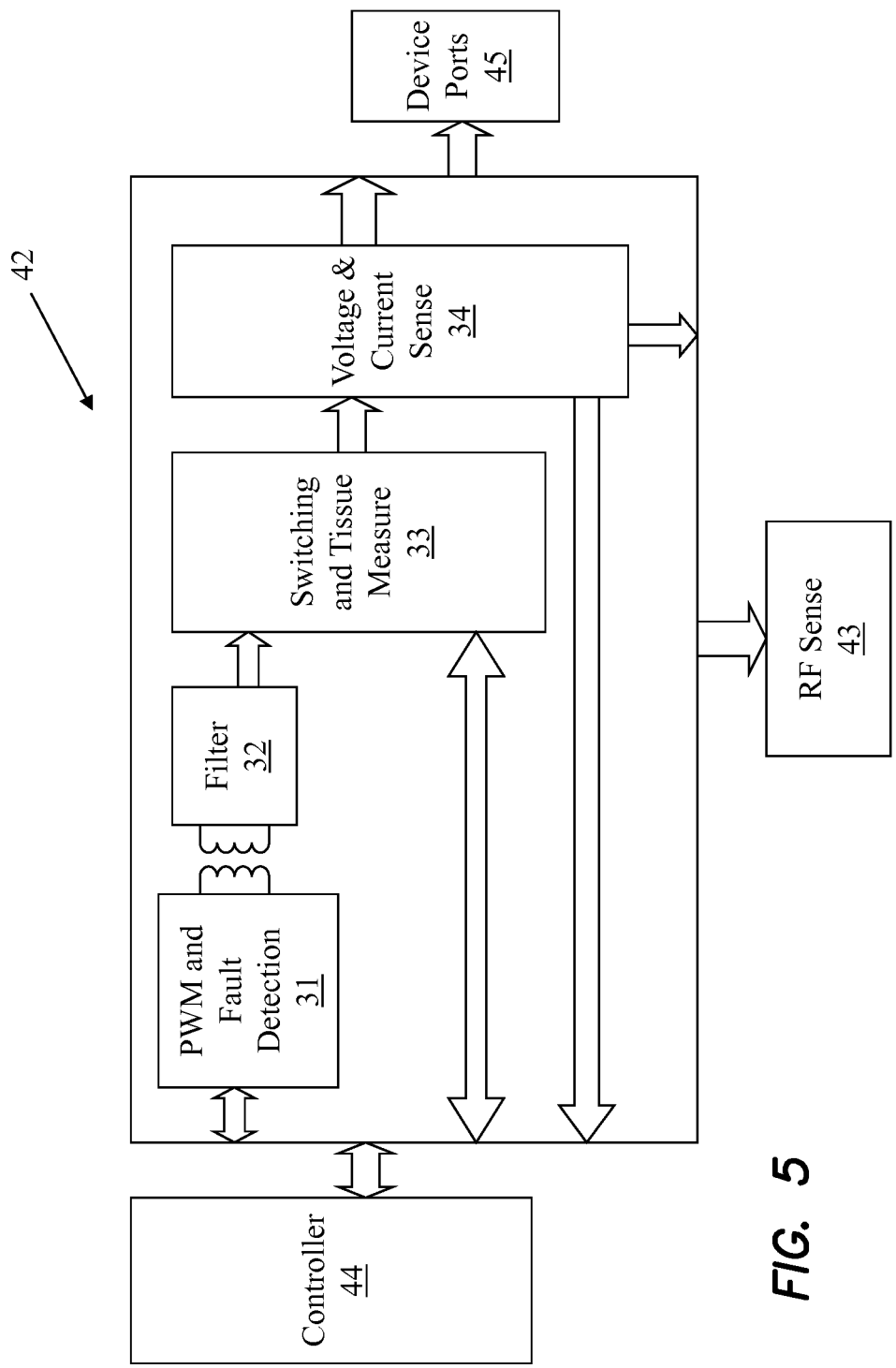
FIGS. 5 to 6 are schematic block diagrams of portions of an electrosurgical system in accordance with various embodiments of the present invention.
Figures 1, 5:
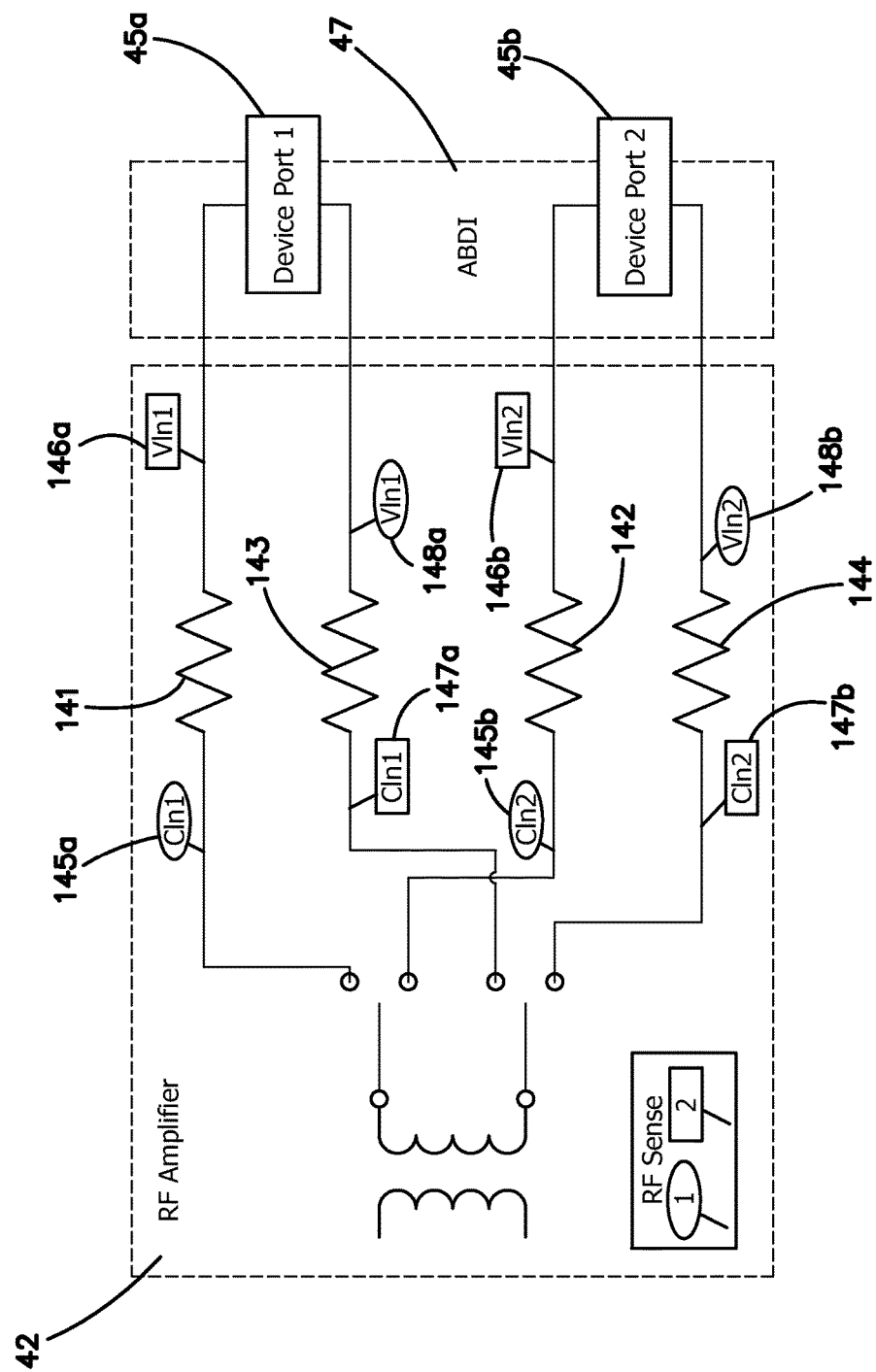
Figures 2, 5:
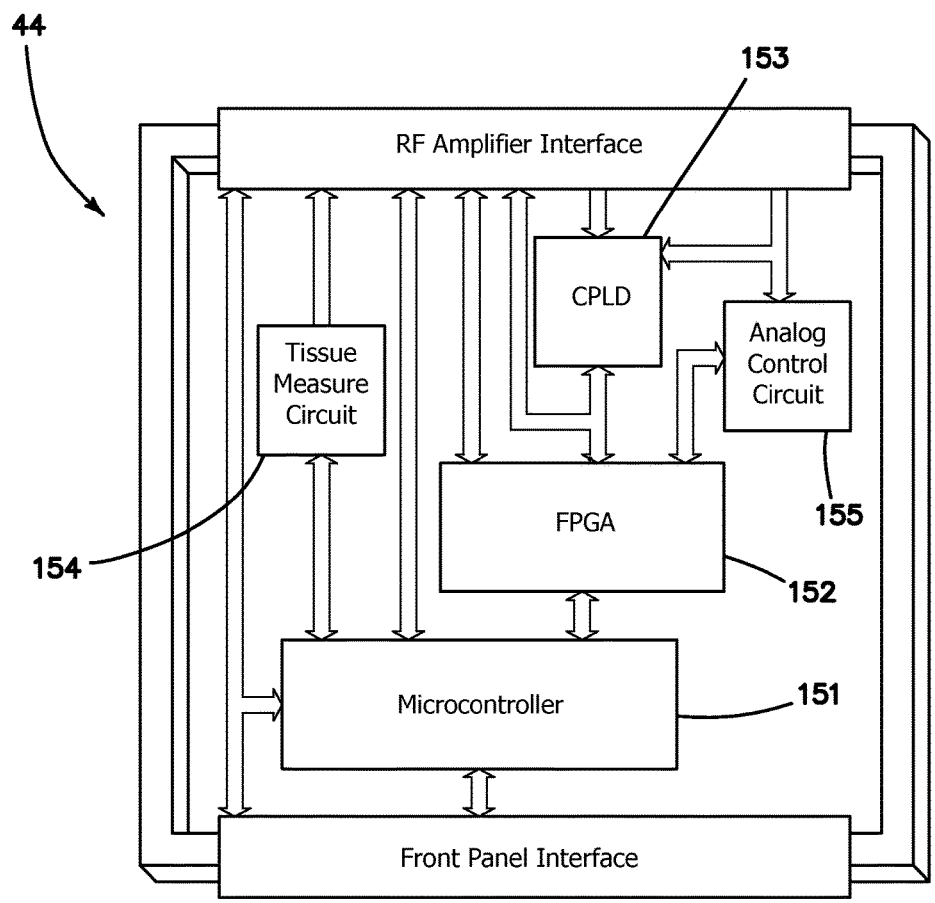
Figures 3, 5:
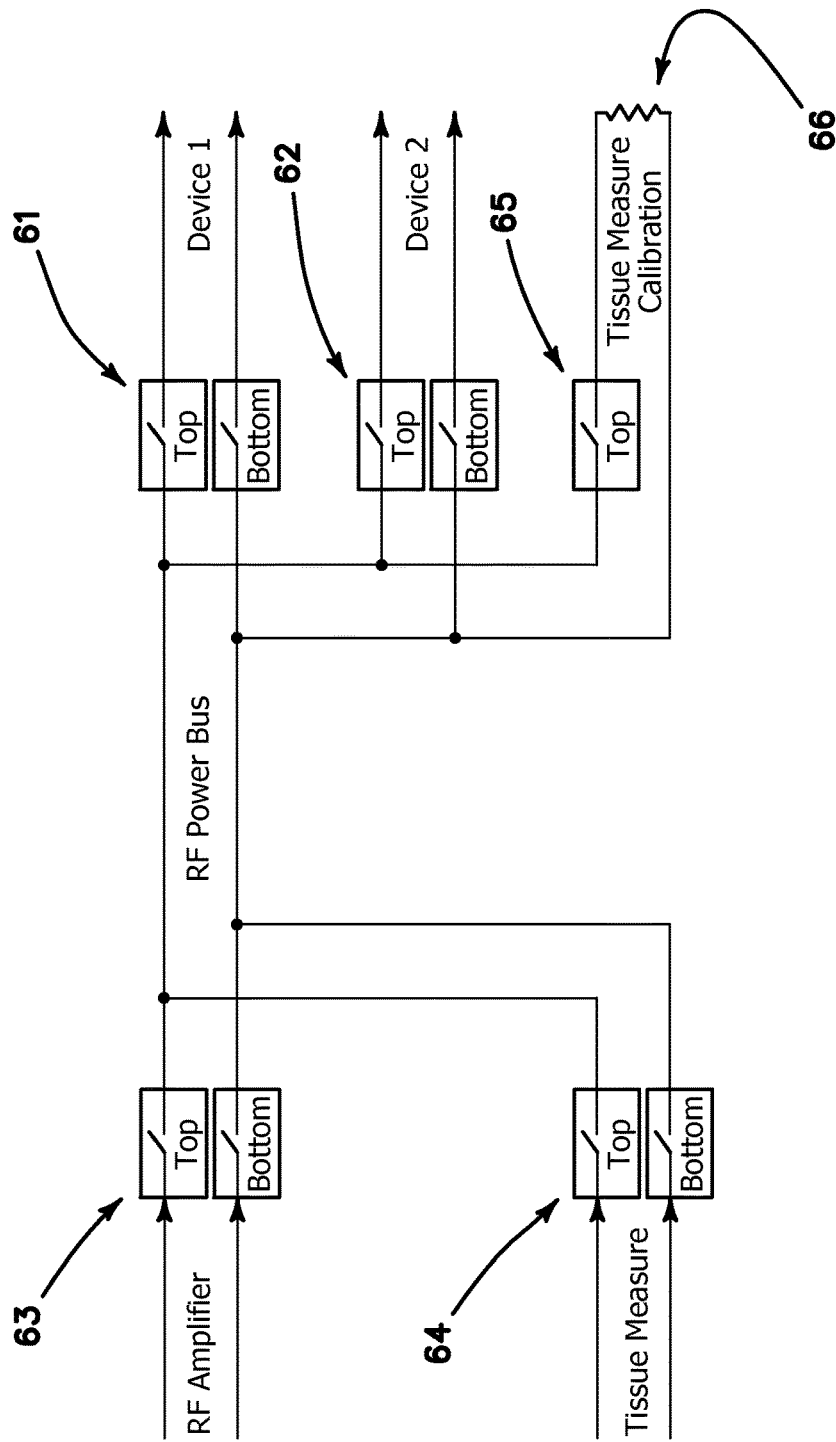
Figures 4, 5:
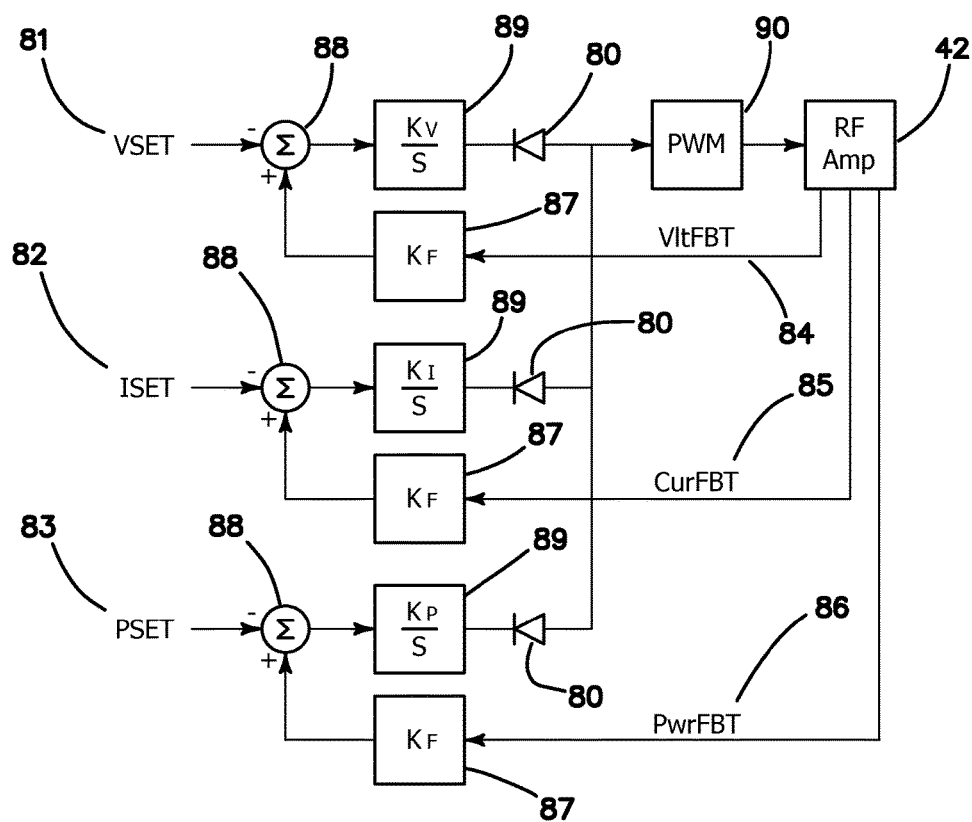

Referring now also to FIG. 5, the RF amplifier comprises a transistor H-bridge circuitry in which pairs of transistors are switched on and off in accordance with a pulse width modulation signal from a pulse width modulation and fault detection circuitry 31 to generate a sinusoidal signal from DC voltage supplied to the RF amplifier. The RF energy is supplied to the electrosurgical instrument via device ports 45. The sinusoidal signal is filtered by filter circuitry 32 and communicated to the connected and active electrosurgical instrument by switching and tissue measure circuitry 33. Voltage, current, power, phase and other measured/calculated information is determined by a voltage and current sense circuitry 34 in conjunction with the RF sense 43. In one embodiment, the generator includes a relay matrix which selectively switches or steers the RF energy from the RF amplifier to one of the device ports. In one embodiment, the switching and tissue measure circuitry 33 includes a low voltage network analyzer circuit used to measure instrument and/or tissue impedance before RF power is turned on. If successful, e.g., no short or open is detected for an electrosurgical device, RF energy is switched and thus the RF amplifier 42 supplied RF energy to one of the device ports 45.

The RF amplifier 42 in one embodiment receives voltage and current set points, which are input by the user through a user interface, to set the output level of the RF amplifier. The user sets points are translated into operating levels by digital to analog converters of the RF amplifier. The set points in one embodiment include a maximum voltage output, maximum current output, and a maximum power output. In accordance with various embodiments, the RF amplifier provides the RF energy based on one or more of these set points, such as providing the output voltage of the RF amplifier so that one or more of the set points are not exceeded.

The RF Amplifier in accordance with various embodiments manages the DC to RF conversion process as well as certain system electrical measurements. Switching and tissue measure circuitry routes RF transformers or measurement components to the output electrodes. In accordance with various embodiments, volt-ampere (VA) is the unit used for the apparent power provided by the generator and is equal to the product of root-mean-square (RMS) voltage and RMS current. In direct current (DC) circuits, this product is equal to the real power (active power) in watts. Volt-amperes are useful in the context of alternating current (AC) circuits (sinusoidal voltages and currents of the same frequency). Volt-amperes and watt have a dimension of power (time rate of energy), but are still different.

The controller FPGA has direct control of the RF output relays. The output relay configuration determines which drive signal (RF or tissue measure) is routed to which device port, either device port 1 or 2 as shown in FIGS. 5-1 and 5-4. During calibration they can also connect to a predetermined load, e.g., a resistor having a set value, across the tissue measure analyzer to calibrate it before connecting the device load (load of the connected electrosurgical instrument in contact with tissue). The RF output relays are located by or incorporated into the RF Amplifier 42.

In accordance with various embodiments, the controller generates a pair of Device 1 Relay control signals for Device 1 relay pair 61 to connect the RF energy bus to the device 1 port. In a similar manner, the controller generates a pair of Device 2 Relay control signals for Device 2 relay pair 62 to connect the RF energy bus to the device 2 port. The RF Amplifier relay pair 63 controls whether the RF amplifier output is connected to the RF energy bus and the Tissue Measure relay pair 64 controls whether the Tissue Measure analyzer is connected to the RF energy bus. The RF amplifier and Tissue Measure analyzer are sources to the RF energy bus, and the device ports are destinations for the selected energy. The Tissue Measure Calibration relay 65 connects the predetermined calibration load across the RF energy bus.

As such, in accordance with various embodiments are used to direct the flow of RF energy or the output of the tissue measurement circuit to one of the device ports. Four pairs of relays signals control four pairs of relays that change the flow of energy through the system. A first relay pair allows for the high power RF signals to flow to the ABDI 47 and eventually through the connected device. A second relay pair allows for the tissue measure circuit to send and measure signals from the devices via the ABDI. A third and fourth relay pair allow for the signal, whether being the high power RF signals or the tissue measure signals to flow to either Device 1 or Device 2 via the ABDI. The signals that control the relays are controlled by the Controller 44.

The calibration signal controls a fifth relay that allows the tissue measure circuit on the controller to measure a predetermined load 66. The input signals to the relay circuits, which are HIGH when the relays are open, are inverted by inverters. The output to the inverters is connected to MOSFETs, which controls the relay. When a relay must be closed, the input to the relay circuit goes LOW, which causes the output of the inverter, and thus the input to the MOSFET, to go HIGH. When the input of the MOSFET is HIGH, this allows 5V to flow through the coil, closing the relay and allowing signals to pass through. The relays are open and closed in a certain order or sequence, which is determined by the controller.

In accordance with various embodiments, a Device 1 Active signal is asserted when the relays are configured for RF or Tissue Measure energy on device port 1, a Device 2 Active signal is asserted when the relays are configured for RF or Tissue Measure energy on device port 2, and Device 1 and Device 2 RF On signals are active only when the RF amplifier is ON and the relays are in the RF Energy on Device 1 or RF Energy on Device 2 configurations, respectively.

The controller FPGA controls the RF amplifier based on settings provided by the microcontroller. In one embodiment, the settings from the microcontroller are set by a script file retrieved from memory attached to a connected electrosurgical instrument. The microcontroller in one embodiment sets the desired voltage, current and power levels and enables an RF amplifier output.

In one embodiment, a low power buffered voltage-out DAC provides the set values for Voltage, Current and Power to the control loop and error amplifier. The control loop or system is illustrated in FIG. 5-5. The voltage, current, and power feedback voltages 84, 85 and 86 go through a filter which is shown as a gain stage 87. This filtered feedback is summed 88 with respective set point parameters and each error is then integrated through a circuit 89 that was tuned for each parameter. All of the error outputs junction together with diodes 80 so that the lowest output controls the PWM circuit 90.

Each of the low-passed voltage, current and power feedback signal and the inverted set voltage, current and power signals (VSET 81, ISET 82, and PSET 83) pass through a resistor and combine together to make a signal with amplitude of (FVltFBT−Vset)/2, (FCurFBT−Iset)/2, and (FPwrFBT−Pset)/2 which are considered as an error signal in each control loop. The next stage is a proportional-integral controller (PI) that produces a DC signal (VError, IError, PError) as the result of error signal changes at its input. VError, IError, PError are used at a summing junction to define which one of voltage, current or power are in the control of the main control loop to force certain PWM duty cycle for RF amplifier 42.

Figure 6:
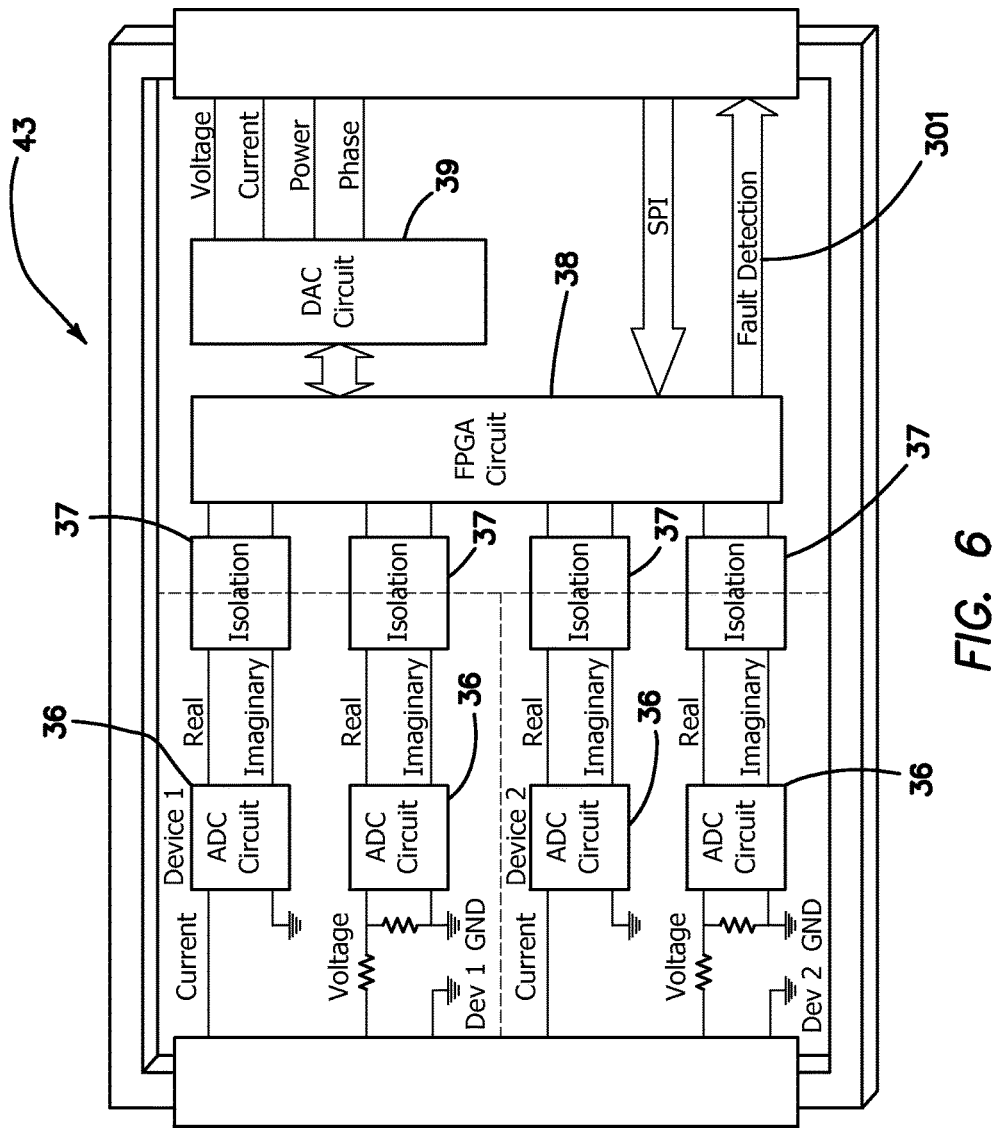
Figures 1, 6:
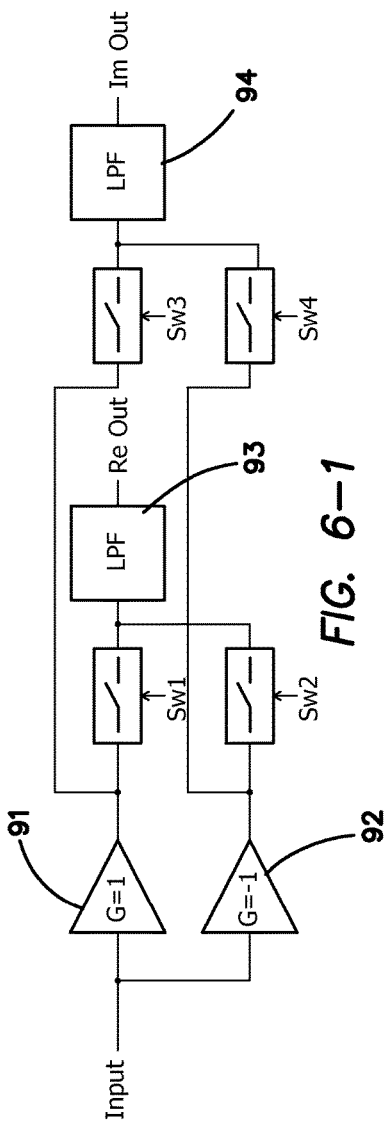
Figures 3, 6:
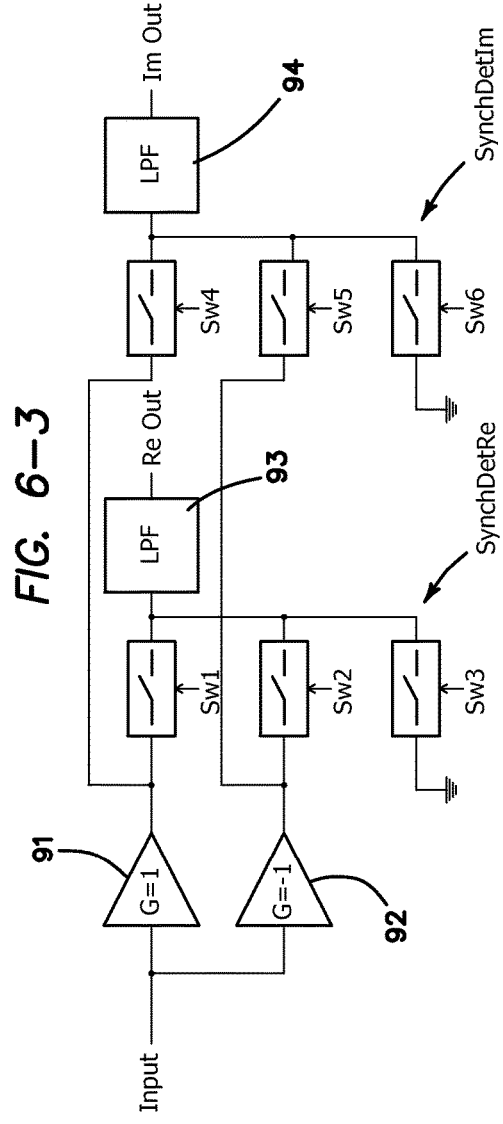
Figures 2, 6:
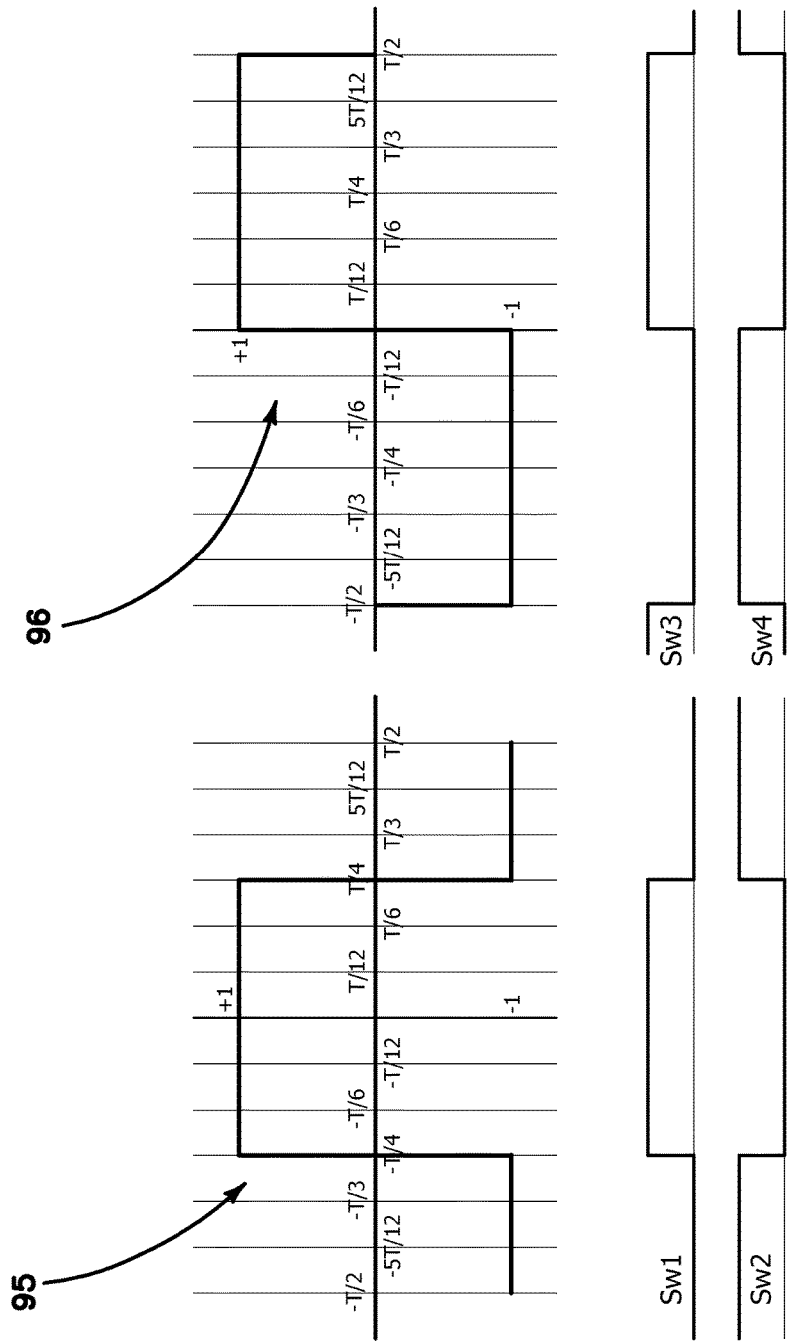
Figures 4, 6:
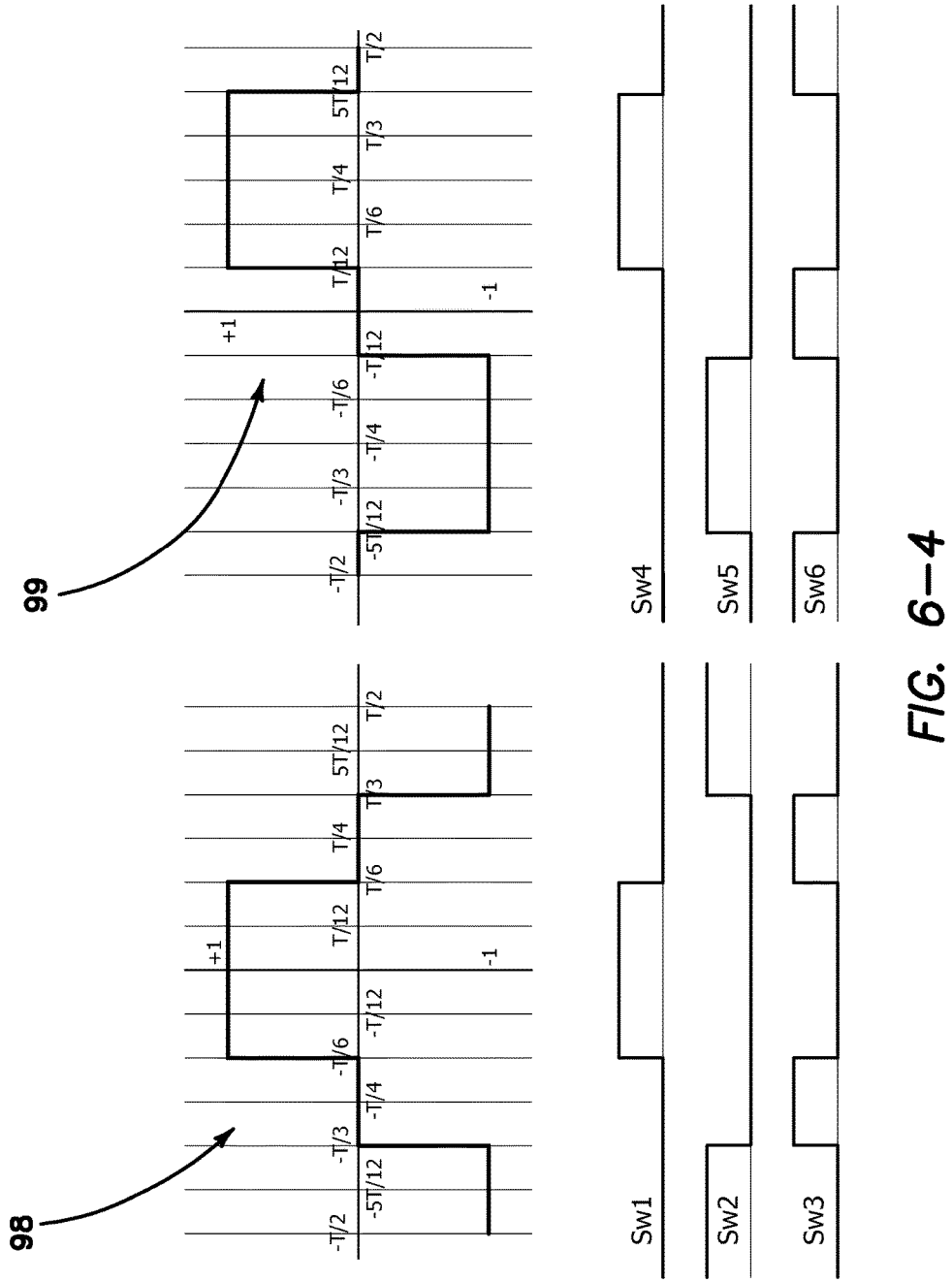
Figures 5, 6:
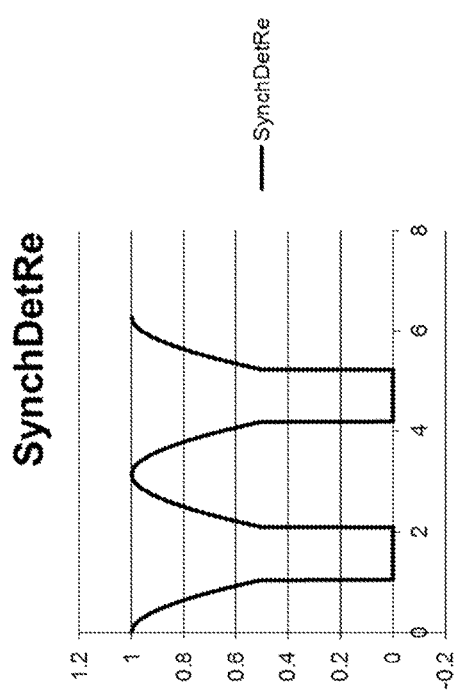
Figure 6:
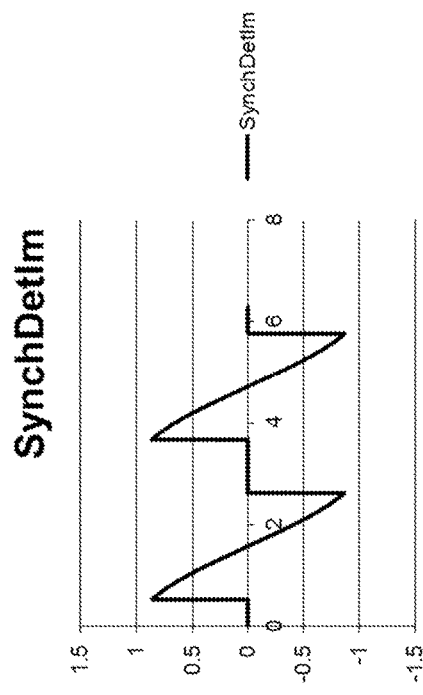

Referring also now to FIG. 6, RF sense 43 comprises a synchronous detector that samples the RF energy being supplied to the electrosurgical instrument. The RF sense removes unwanted harmonics of the RF energy by multiplying the supplied RF energy to a reference signal or signals. From the signal product, the RMS voltage, RMS current, apparent power and phase information can be calculated. The RF sense includes ADC circuitry 36, isolation components 37, an FPGA 38 and a DAC 39. Real and imaginary components of raw current and voltage data are determined via the Analog to Digital circuits and these components that provided to an FPGA 38 via isolation barriers or components 37 for processing of the components. In the illustrated embodiment, two device channels are provided for two advanced bipolar electrosurgical tool ports and the associated instruments. Fault detection data 35 is supplied via the FPGA 38 and digital forms of measured or calculated voltage, current, power and phase are provided by the DAC circuitry 39. In one embodiment, the FPGA is responsible for signal conditioning of feedback signals from the synchronous detector and is also responsible for detecting faults.

The ADCs 36 simultaneously sample the output of the synchronous detector, which represent the real and imaginary values for the voltage and current of the output signal on each device port. After they sample, the FPGA stores these values in an ADC control module. An ADC error correction module pulls this data from the ADC control module via a multiplexer to correct sample errors by applying offset and gain corrections.

The output of the ADC error correction module is a representation of the real and imaginary components of voltage and current from both an active and inactive device port. The output of the ADC correction module also outputs a sign bit for each signal from the active device port for phase calculation. A separate module takes the real and imaginary values for the voltage and current from the active device port and computes the RMS voltage, RMS current, and apparent power magnitudes and the phase between voltage and current. Once these values are computed, the DAC error correction module applies offset and gain corrections to the scaled and signed representation of each signal. DAC error correction for voltage, current, power, and phase is done sequentially. The data is sent to the DAC controller module. The DAC controller module sends out data to the DACs.

The FPGA 38 monitors the real and imaginary values for voltage and current and generates fault codes if their values deviate beyond a specific threshold on the inactive device port. Additionally, if the phase relationship between the synchronization signals is lost, the FPGA will generate a fault code. The synchronization monitor module has four inputs that are always 180 degrees out of phase from each other. This module monitors for valid time relationships between the signals and flags an error if there is a violation.

In accordance with various embodiments, the RF sense FPGA is configured to correct for errors in RF feedback signals and calculate the magnitude and phase of these signals. A synchronous detector of the RF Sense uses synchronization signals generated by the controller FPGA to generate in-phase (real) and quadrature (imaginary) components of the voltage and current feedback signals from the RF Amplifier. The RF sense FPGA monitors the phase relationship between synchronization signals generated by the controller and asserts a fault when the phase relationship is out of order.

In accordance with various embodiments, a plurality of synchronization signals are used as clock inputs for RF Sense. The synchronization signals have the same duty cycle and frequency. The only difference between the signals is their phase relationship. For example, in one embodiment, a first synchronization signal is used as a reference and the second synchronization signal is identical to first synchronization signal but is delayed by 180 degrees. A third synchronization signal is delayed from first synchronization signal by 90 degrees and a fourth synchronization signal is delayed from first synchronization signal by 270 degrees. The clock edges provided by these four signals provide the exact timing required by the RF Sense for proper sampling of the RF output signal.

In accordance with various embodiments, the electrosurgical generator measures RF output voltage and current. Due to the electrosurgical nature of the generator, however, it is required that the measurements be done using isolated circuitry. Voltage measurement can be simple because the signal to noise ratio is relatively high. Current measurement using a current transformer however is problematic since there is a significant level of PWM output stage switching noise present in the circuit and isolation of typical current transformer cannot suppress this noise enough for the desired or required accuracy. Sampling the output voltage and current directly by using secondary side referenced (floating) Analog to Digital Conversion (ADC) and a shunt resistor can also create a different problem.

PWM switching noise is not harmonically related to the fundamental PWM carrier frequency and has a wide bandwidth. This noise can be overcome by significantly oversampling the signal in order to achieve a desired or necessary accuracy. However, with a 350 kHz PWM carrier frequency, 64 times over Nyquist sampling frequency and 12-bit resolution, the required speed of the digital stream is $5.376 \times 10^8$ bits/s, per ADC channel. ADCs and digital isolators with this performance are difficult to source and relatively expensive.

In accordance with various embodiments, by using an accurate analog preprocessor the frequency requirements for the digital stream can be lowered. The analog preprocessor utilizes the fact that change of the RF output voltage and current in time is relatively slow and in general, the useful bandwidths of those signals are narrow.

In one embodiment, the analog preprocessor comprises a synchronous detector which allows transfer of the RF signal spectrum from the area concentrated around the carrier frequency down to zero. The narrowed bandwidth significantly simplifies the complexity for the ADCs and digital isolators. As such, ADC sampling frequency can be low and digital isolator throughputs are reduced. Digital isolator coupling capacitance is also reduced due to reduced or minimal number of parallel channels. In general, processing speed requirements are reduced which leads to lower cost components.

Referring to FIGS. 6-1 to 6-4, in accordance with various embodiments, a synchronous detector comprises an analog multiplier, which defines overall accuracy of the circuit. However, due to the presence of off-band PWM noise and/or a 350 kHz carrier frequency existing analog multipliers will not satisfy an accuracy requirement of 0.5% or better.

A local oscillator (LO), which is required for spectrum transform, can be non-sinusoidal. If the number of gain levels present in such a waveform is limited, an analog multiplier can be implemented using analog switches instead of a multiplier.

In one embodiment, as shown in FIGS. 6-1 to 6-2, the LO waveform 95, 96 utilized is a square wave where gain 91, 92 can be either +1 or −1. Low pass filters (LPF) 93, 94 at the outputs of switches are used for averaging and to suppress conversion components with high frequencies. The input signal 97 of the synchronous detector can be defined as the fundamental frequency:

$$\omega = \frac{2\pi}{T}$$

where T is defined as the fundamental period, A is the fundamental amplitude and p is the fundamental phase. The $3^{rd}$ harmonic frequency can be defined as:

$$3\omega = \frac{6\pi}{T}$$

where kA is defined as the amplitude of the $3^{rd}$ harmonic frequency, k is the ratio of the $3^{rd}$ harmonic amplitude over fundamental, and q is the phase of the $3^{rd}$ harmonic frequency. Real (Re) and Imaginary (Im) output voltages of the synchronous detector are as follows:

$$\text{Re} = \frac{A}{T}\left\{-\int_{-\frac{T}{2}}^{-\frac{T}{4}}\left(\cos\left(\frac{2\pi t}{T}+p\right)+k\cos\left(\frac{6\pi t}{T}+q\right)\right)dt + \right.$$

-continued $$\int_{-\frac{T}{4}}^{\frac{T}{4}}\left(\cos\left(\frac{2\pi t}{T}+p\right)+k\cos\left(\frac{6\pi t}{T}+q\right)\right)dt -$$

$$\int_{\frac{T}{4}}^{\frac{T}{2}}\left(\cos\left(\frac{2\pi t}{T}+p\right)+k\cos\left(\frac{6\pi t}{T}+q\right)\right)dt =$$

$$\frac{A}{6\pi}(-3\sin p + 3\cos p - k\sin q - k\cos q) + \frac{A}{6\pi}(6\cos p - k\cos q) +$$

$$\frac{A}{6\pi}(3\sin p + 3\cos p + k\sin q - k\cos q) = \frac{A}{2\pi}(4\cos p - k\cos q)$$

$$\text{Im} = \frac{A}{T}\left\{-\int_{-\frac{T}{2}}^{0}\left(\cos\left(\frac{2\pi t}{T}+p\right)+k\cos\left(\frac{6\pi t}{T}+q\right)\right)dt +\right.$$

$$\left.\int_{0}^{\frac{T}{2}}\left(\cos\left(\frac{2\pi t}{T}+p\right)+k\cos\left(\frac{6\pi t}{T}+q\right)\right)dt\right\} =$$

$$\frac{A}{3\pi}(-3\sin p - k\cos q) + \frac{A}{3\pi}(-3\sin p - k\cos q) = -\frac{A}{3\pi}(6\sin p + 2k\sin q)$$

In the case that only the fundamental frequency is present in the input signal spectrum (k=0), complex amplitude can be calculated as follows:

$$\text{Mod} = \frac{2A}{\pi}$$

$$\text{Arg} = \text{Atan}\frac{-\sin p}{\cos p}$$

If the amplitude of the $3^{rd}$ harmonic is not equal to the zero, the complex amplitude can have a different result.

Referring now to FIGS. 6-3 to 6-4, in accordance with various embodiments, a complex LO 3-level waveform 98, 99 generated by a 3-level waveform local oscillator can be used. By using the LO 3-level waveform, real and imaginary output voltages become independent on the presence of the $3^{rd}$ harmonic, but can be distorted if higher order harmonics are present. Real (Re) and Imaginary (Im) output voltages of the synchronous detector are as follows:

$$\text{Re} = \frac{A}{T}\left\{-\int_{-\frac{T}{2}}^{-\frac{T}{3}}\left(\cos\left(\frac{2\pi t}{T}+p\right)+k\cos\left(\frac{6\pi t}{T}+q\right)\right)dt +\right.$$

$$\int_{-\frac{T}{6}}^{\frac{T}{6}}\left(\cos\left(\frac{2\pi t}{T}+p\right)+k\cos\left(\frac{6\pi t}{T}+q\right)\right)dt -$$

$$\left.\int_{\frac{T}{3}}^{\frac{T}{2}}\left(\cos\left(\frac{2\pi t}{T}+p\right)+k\cos\left(\frac{6\pi t}{T}+q\right)\right)dt\right\} =$$

$$\frac{A}{12\pi}(-3\sin p + 3\sqrt{3}\cos p - 4k\sin q) + \frac{A\sqrt{3}}{2\pi}\cos p +$$

$$\frac{A}{6\pi}\left(3\sin p + 3\cos\left(p+\frac{\pi}{6}\right) + 2k\sin q\right)$$

Because $$\cos\left(p+\frac{\pi}{6}\right) = \frac{1}{2}(\sqrt{3}\cos p - \sin p)$$

then $$\frac{A}{6\pi}\left(3\sin p + 3\cos\left(p+\frac{\pi}{6}\right) + 2k\sin q\right) =$$

$$\frac{A}{12\pi}(6\sin p + \sqrt{3}\cos p - \sin p + 2k\sin q)$$

and $$\text{Re} = \frac{A\sqrt{3}}{\pi}\cos p$$

$$\text{Im} = \frac{A}{T}\left\{-\int_{-\frac{5T}{12}}^{-\frac{T}{12}}\left(\cos\left(\frac{2\pi t}{T}+p\right)+k\cos\left(\frac{6\pi t}{T}+q\right)\right)dt +\right.$$

$$\left.\int_{\frac{T}{12}}^{\frac{5T}{12}}\left(\cos\left(\frac{2\pi t}{T}+p\right)+k\cos\left(\frac{6\pi t}{T}+q\right)\right)dt\right\} =$$

$$-\frac{A\sqrt{3}}{2\pi}\sin p - \frac{A\sqrt{3}}{2\pi}\sin p = -\frac{A\sqrt{3}}{3\pi}\sin p$$

In this case, the complex amplitude is as follows:

$$\text{Mod} = \frac{A\sqrt{3}}{\pi}$$

$$\text{Arg} = \text{Atan}\frac{-\sin p}{\cos p}$$

Figures 6, 7, 8, 9, 10, 11, 12:
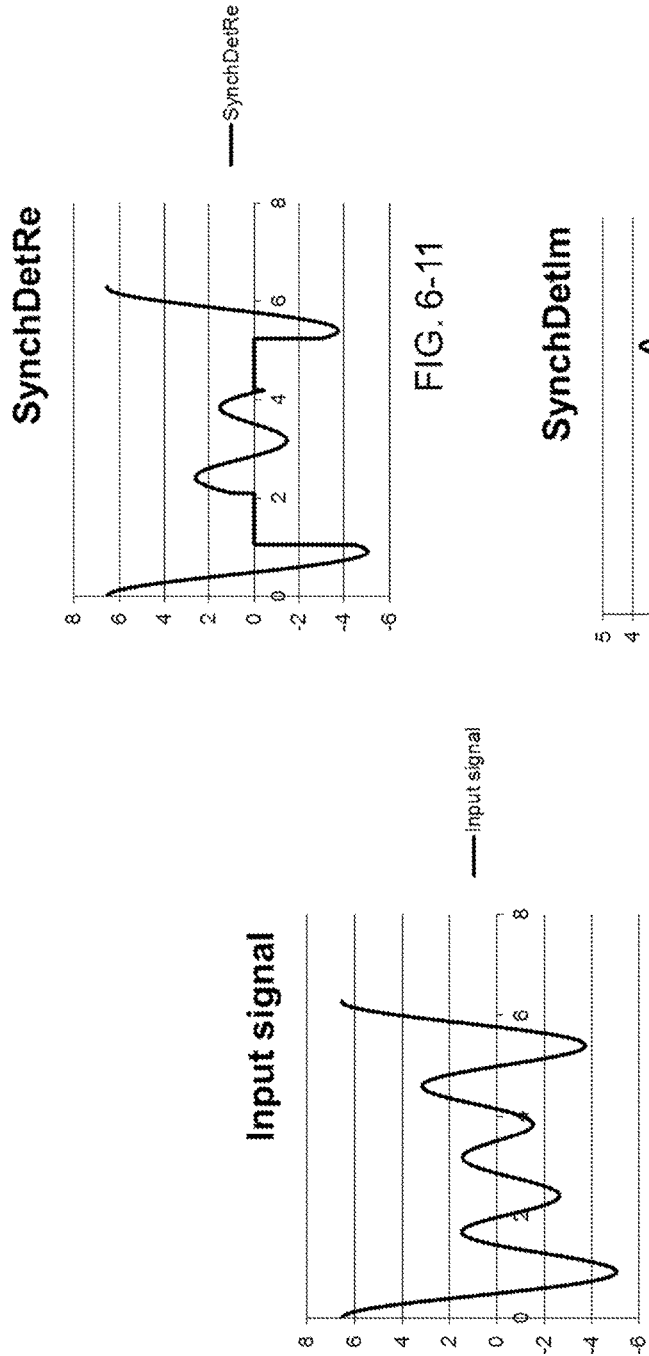
Figure 7:
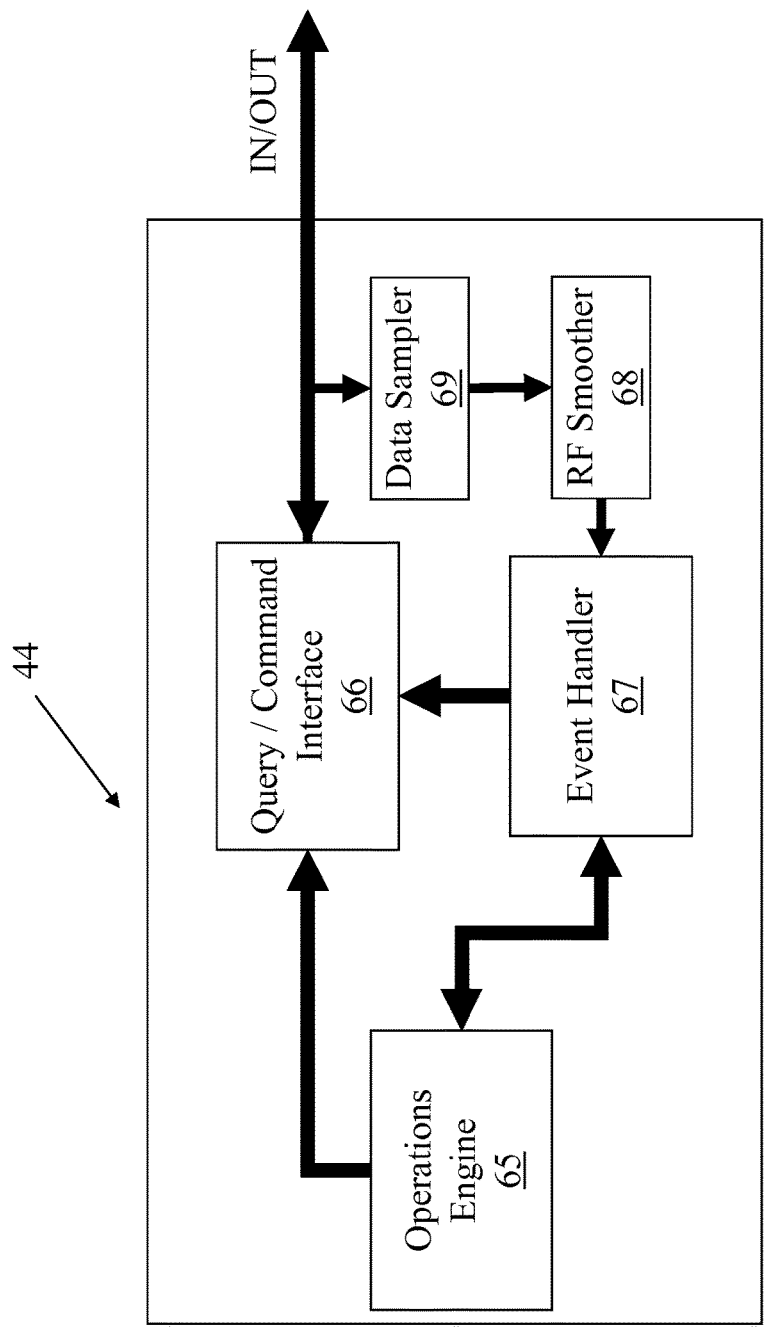
Figure 8:
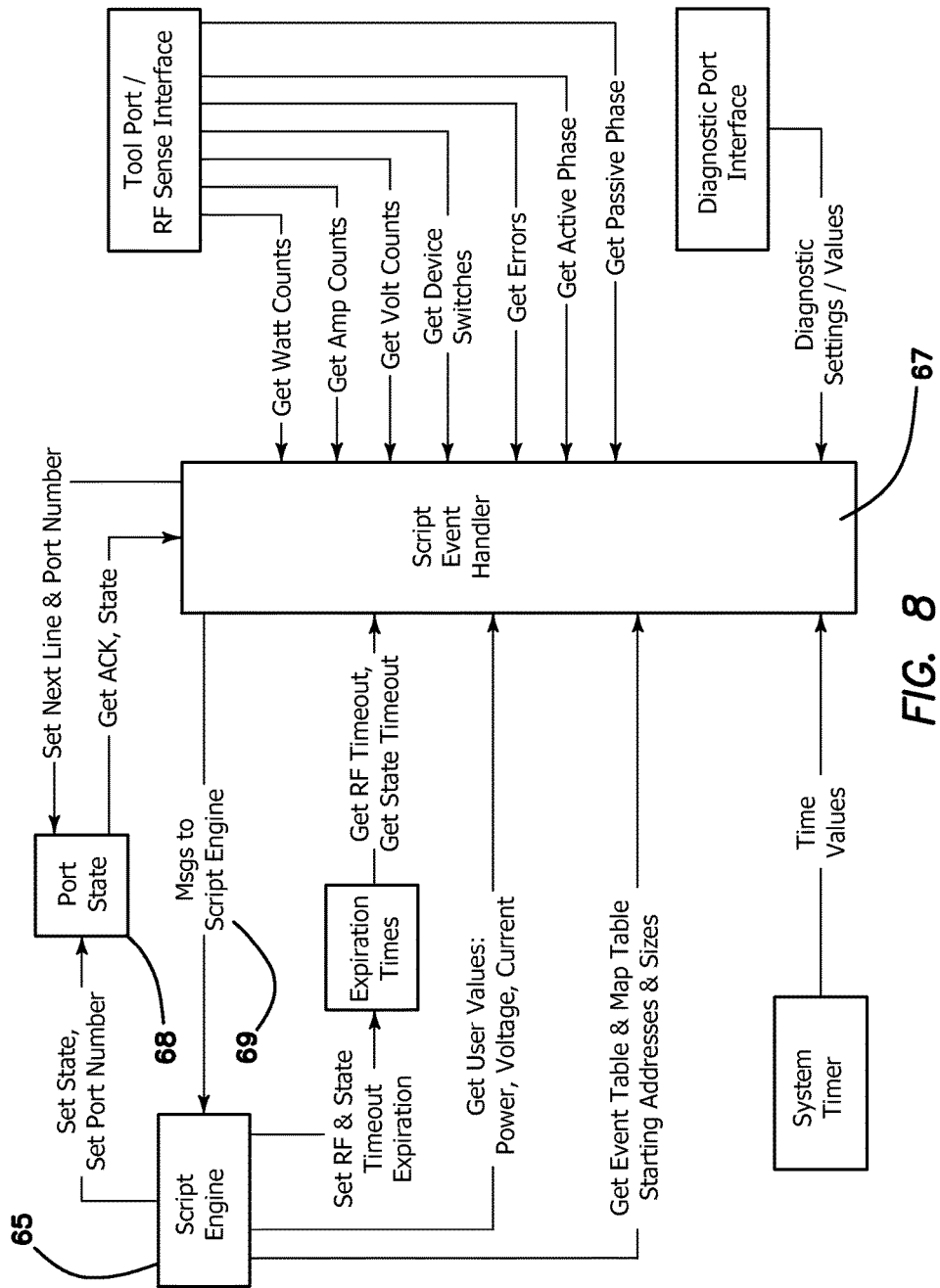
Figure 9:
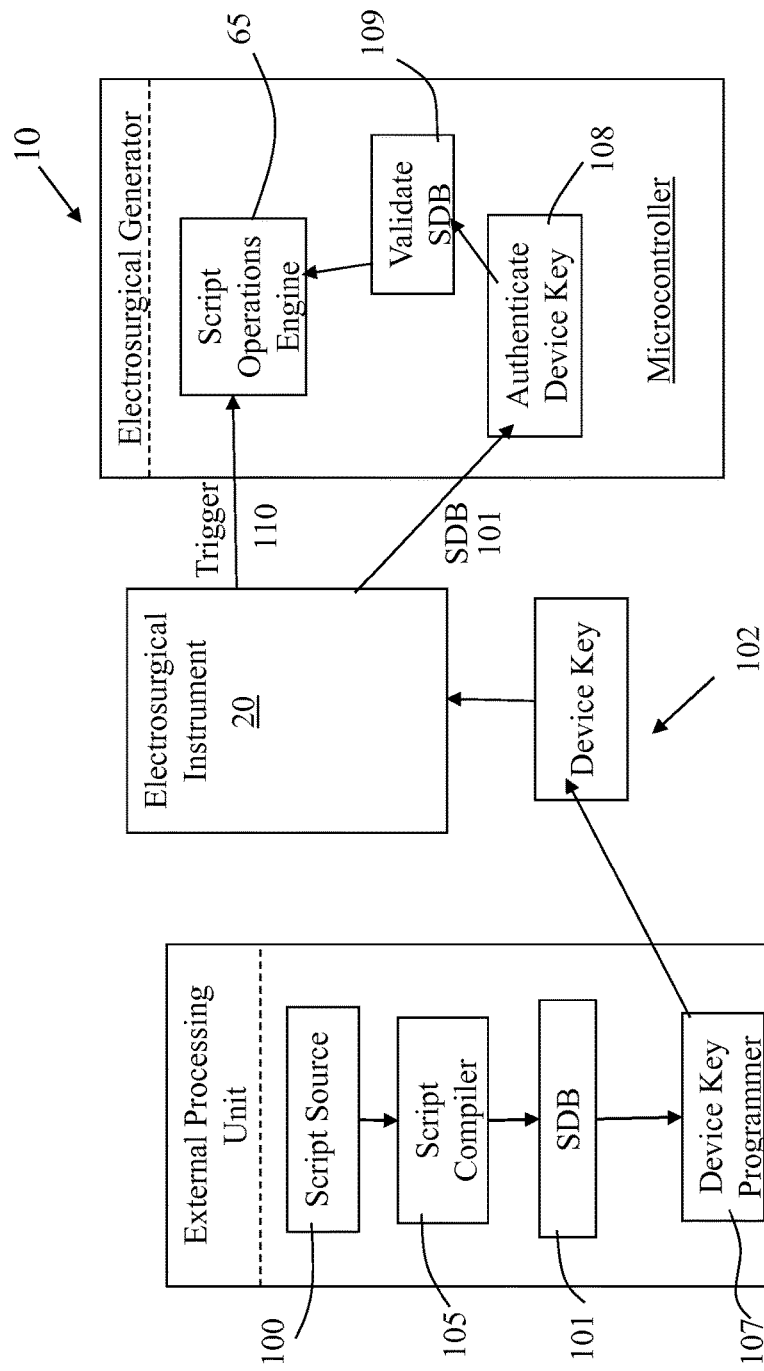
Figure 10:
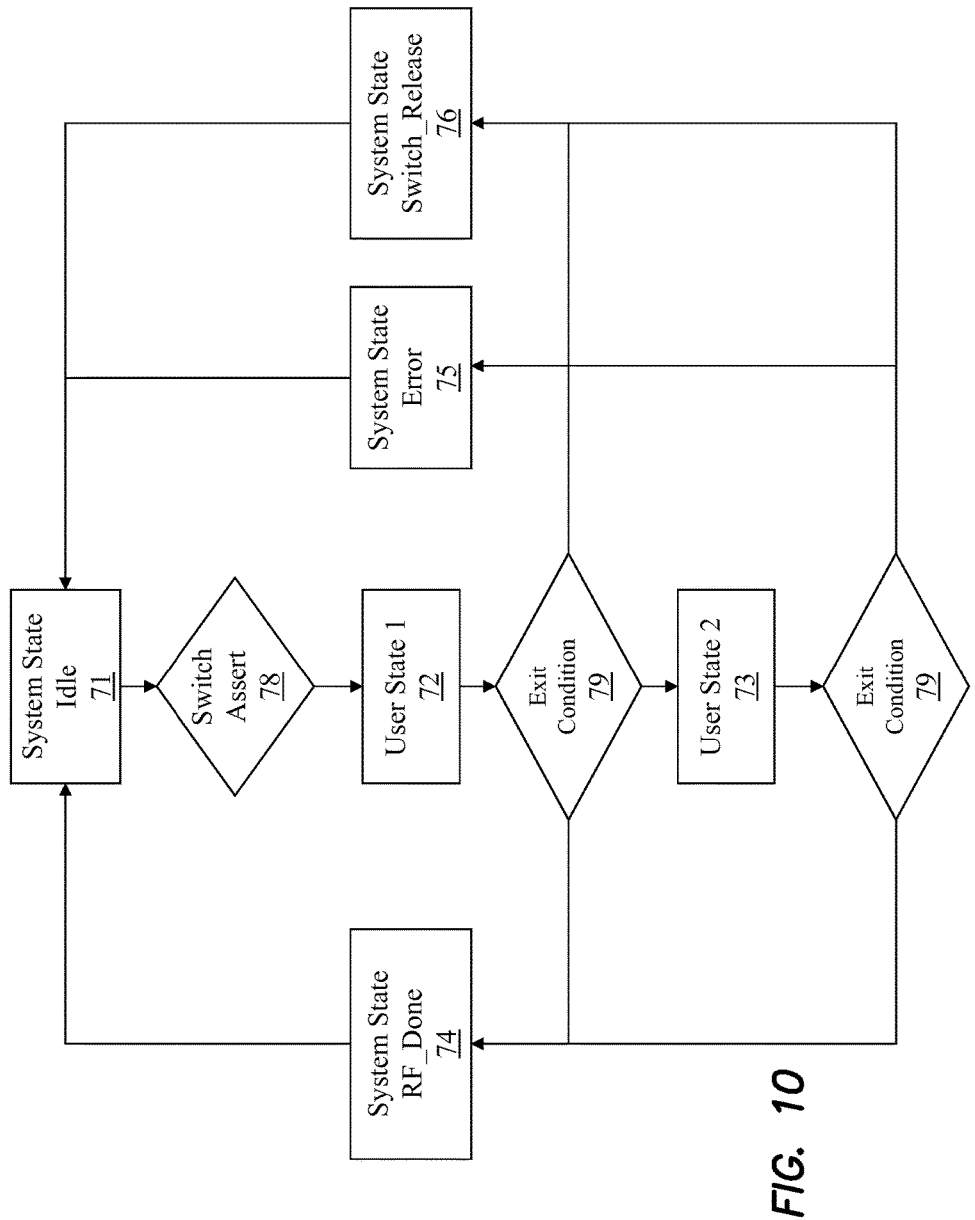

Therefore, the dependence on the presence of $3^{rd}$ harmonic of any level is eliminated. In accordance with various embodiments, the symmetrical nature of a RF amplifier creates signals with naturally low levels of even harmonics. Low pass filters in one embodiment also suppresses high frequency PWM carrier components and is capable of suppression of 5th harmonics to sufficiently low levels. Further examples of the synchronous detector's operation are provided by exemplary signal waveforms at the respective outputs (SynchDetRe and SynchDetIm) prior to filtering by the low pass filter 93 for an exemplary input signal (Uin=cos ωt) are also shown in FIGS. 6-5 to 6-6. FIG. 6-7 provides an exemplary signal waveform illustrating an input signal phase shifted (e.g., Uin=cos(ωt+π/4)) and likewise exemplary signal waveforms at the respective outputs (SynchDetRe and SynchDetIm) prior to filtering by the low pass filter 93 for such an input signal are shown in FIGS. 6-8 to 6-9. FIG. 6-10 provides an exemplary input signal that is significantly corrupted but has no harmonics higher than $4^{th}$ harmonics and likewise exemplary signal waveforms at the respective outputs (SynchDetRe and SynchDetIm) prior to filtering by the low pass filter 93 for such an input signal are shown in FIGS. 6-11 to 6-12. As such, as illustrated, the synchronous detector in accordance with various embodiments can accurately recover the fundamental amplitude and phase of such input signals and thus accurately provide Real (Re) and Imaginary (Im) output voltages for the detection and measurements or calculations of phase and/or rate of changes of phase.

Figure 19:
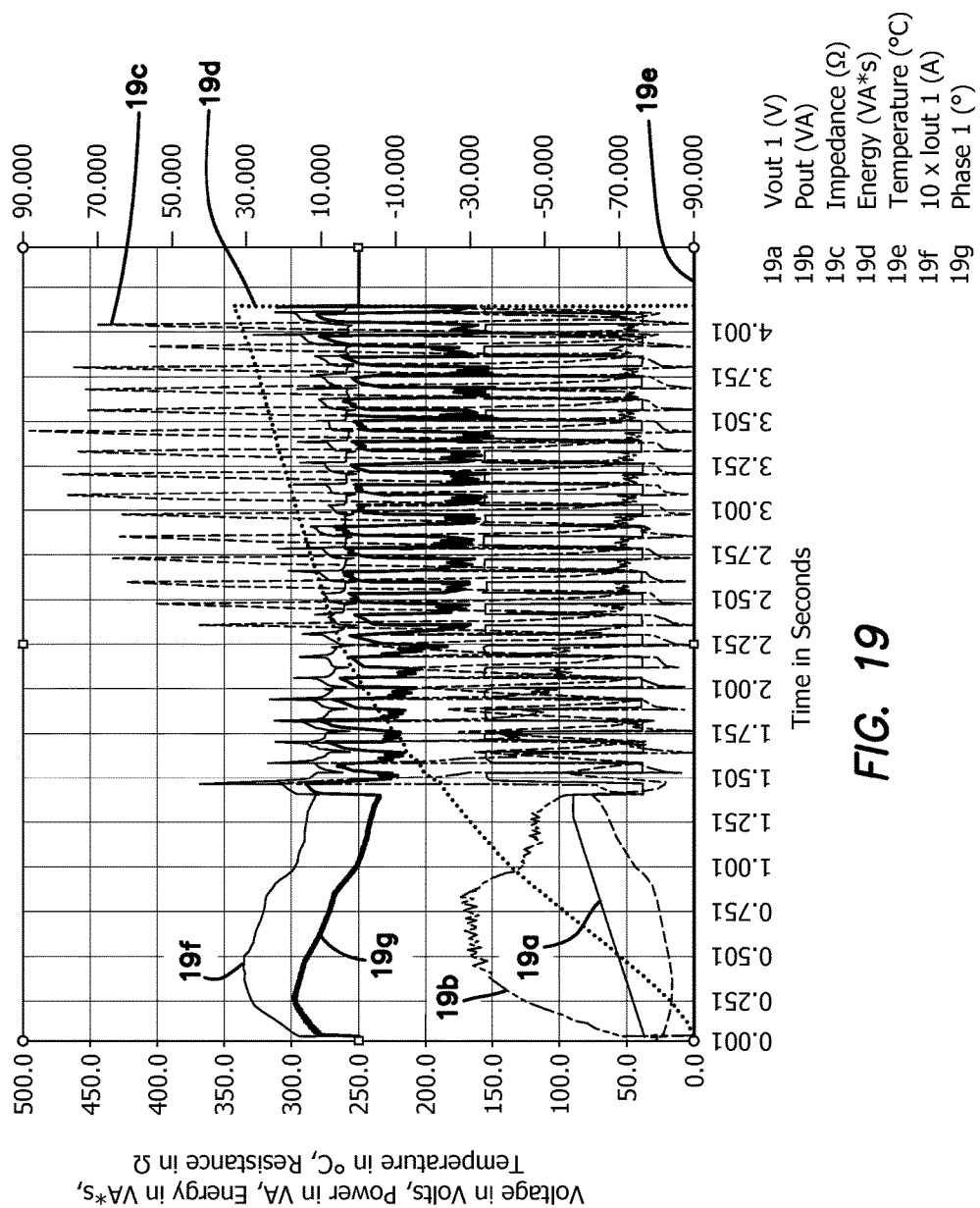
Figure 20:
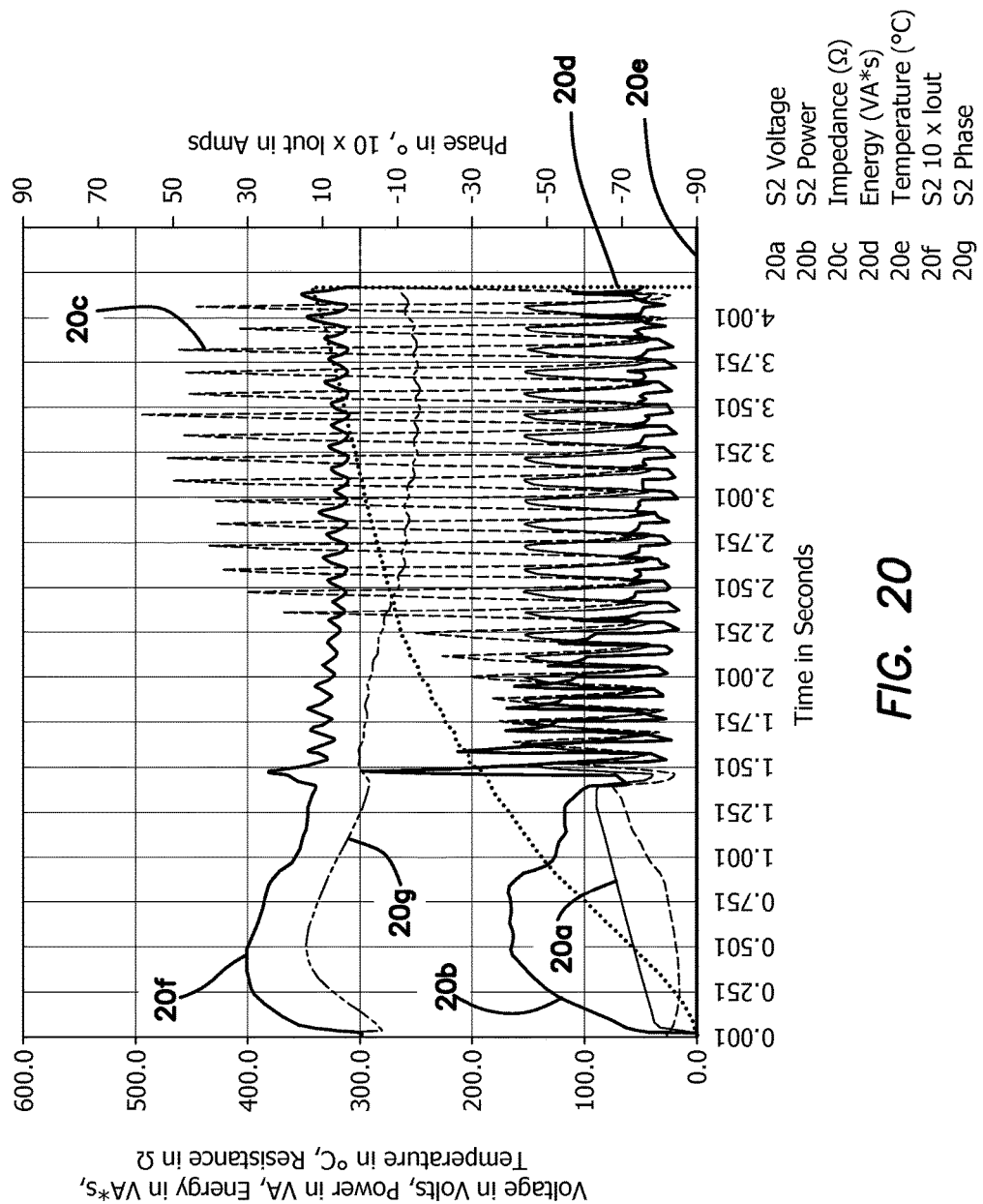
Figure 21:
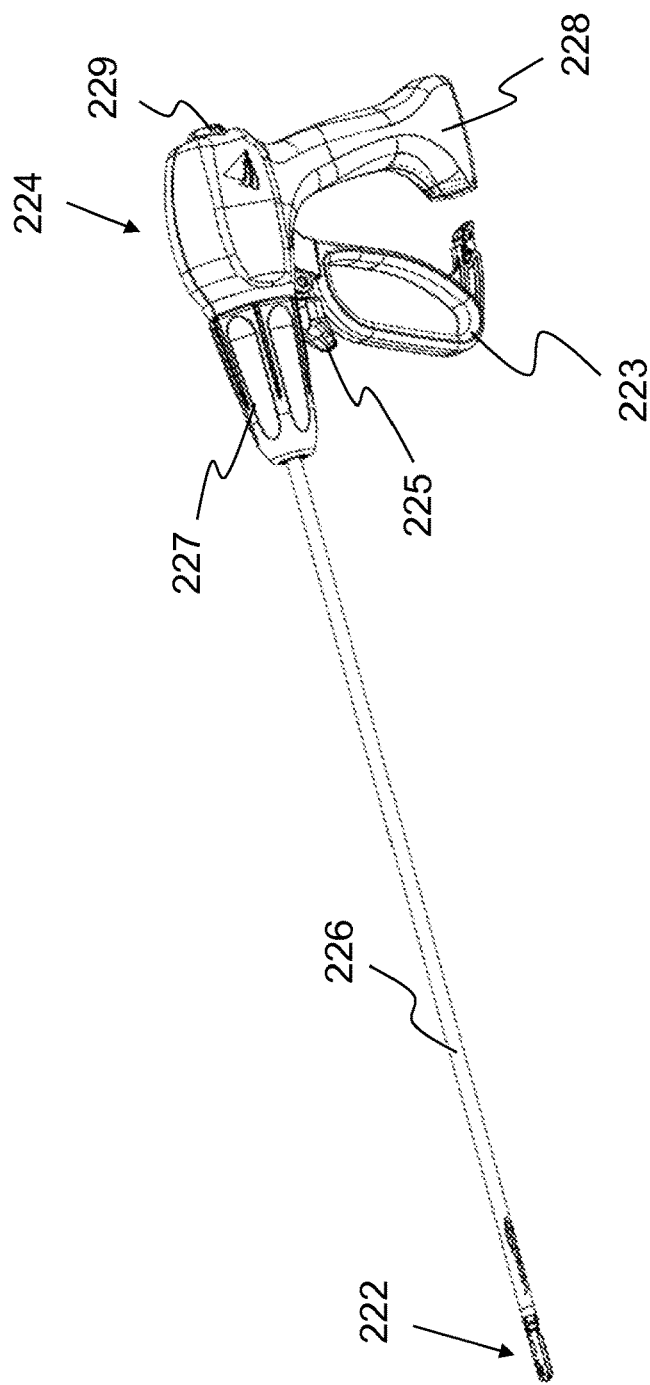
FIG. 21 is a perspective view of an electrosurgical fusion device in accordance with various embodiments of the present invention.
Figure 22:
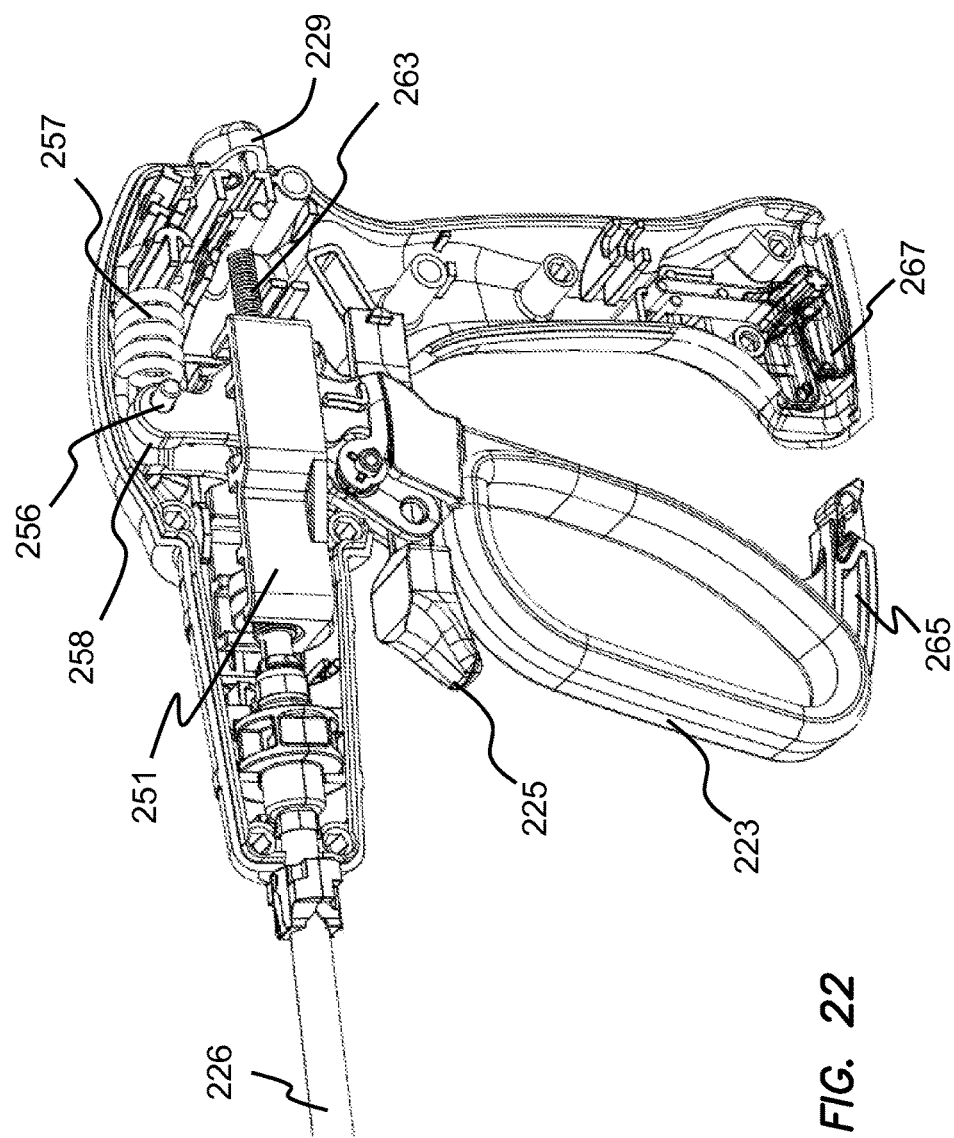
FIG. 22 is a perspective view of a portion of an electrosurgical fusion device in accordance with various embodiments of the present invention.
Figure 23:
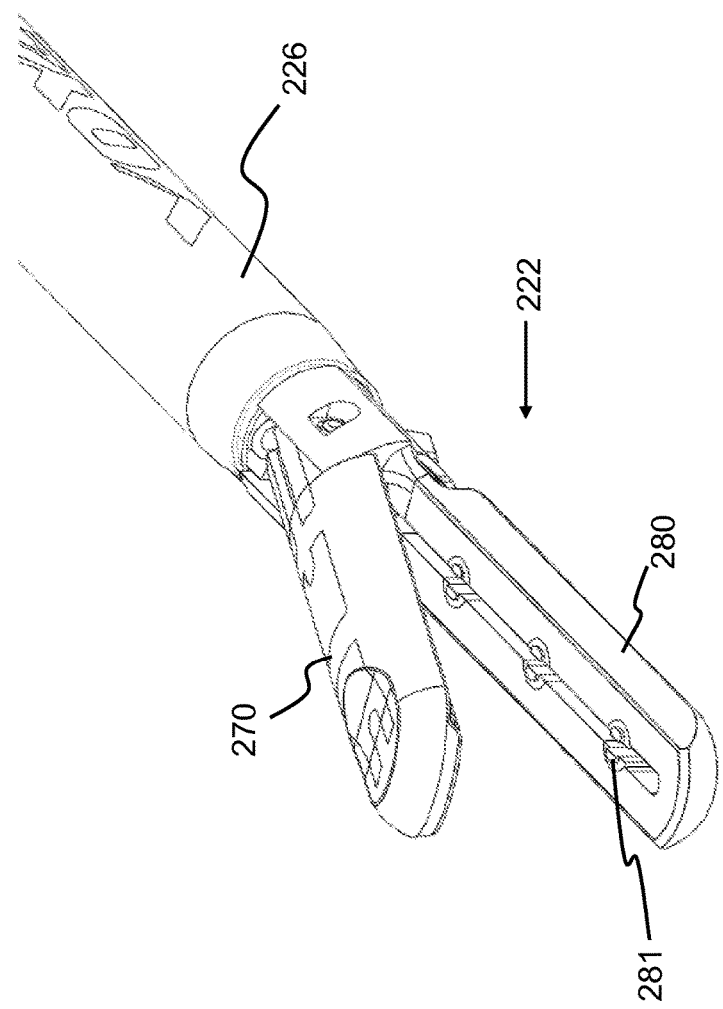
FIG. 23 is a perspective view of a distal end of the electrosurgical device in accordance with various embodiments of the present invention.
Figure 24:
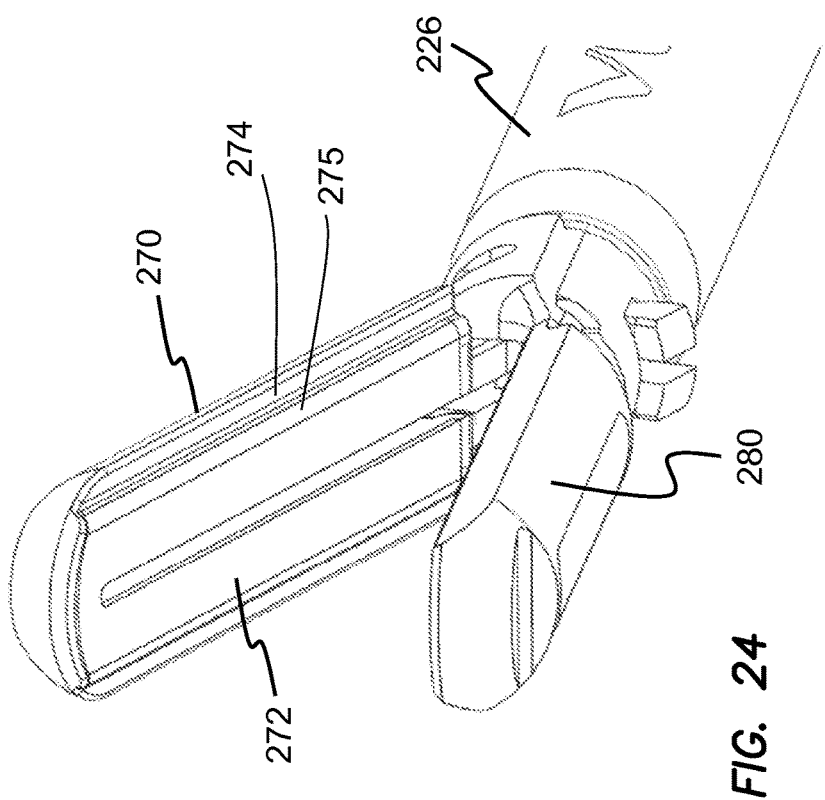
FIG. 24 is a perspective view of a distal end of an electrosurgical device in accordance with various embodiments of the present invention.
Figure 25:
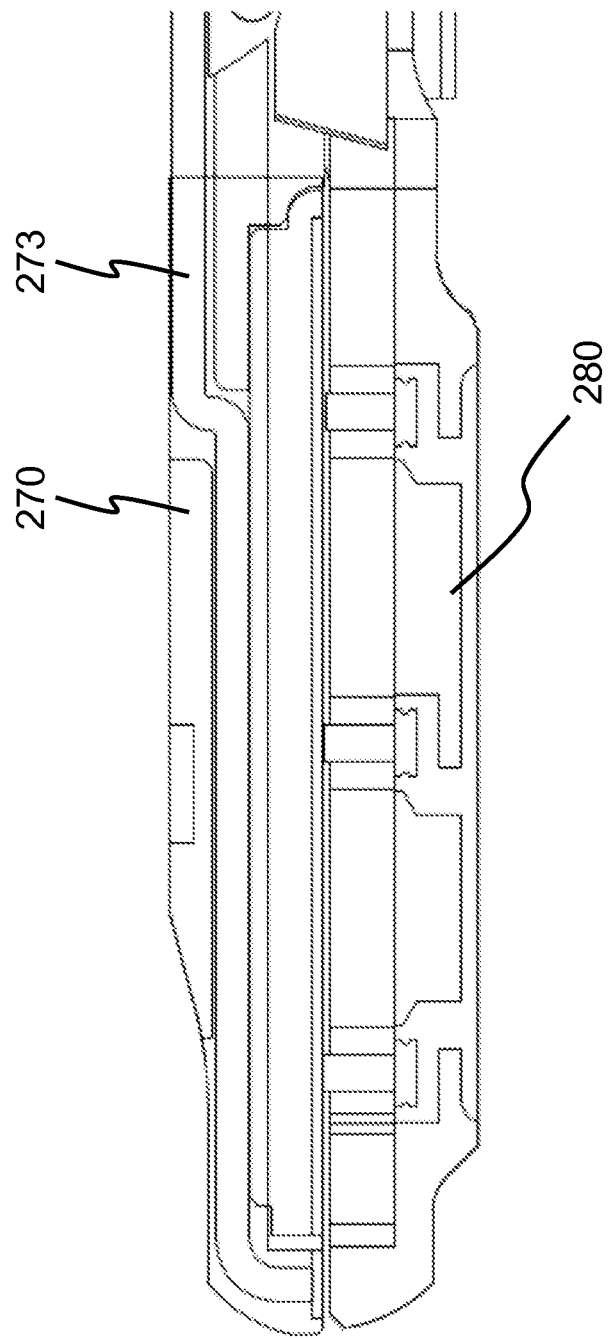
FIG. 25 is a side cross-sectional view of a distal end of an electrosurgical device in accordance with various embodiments of the present invention.
Figure 26:
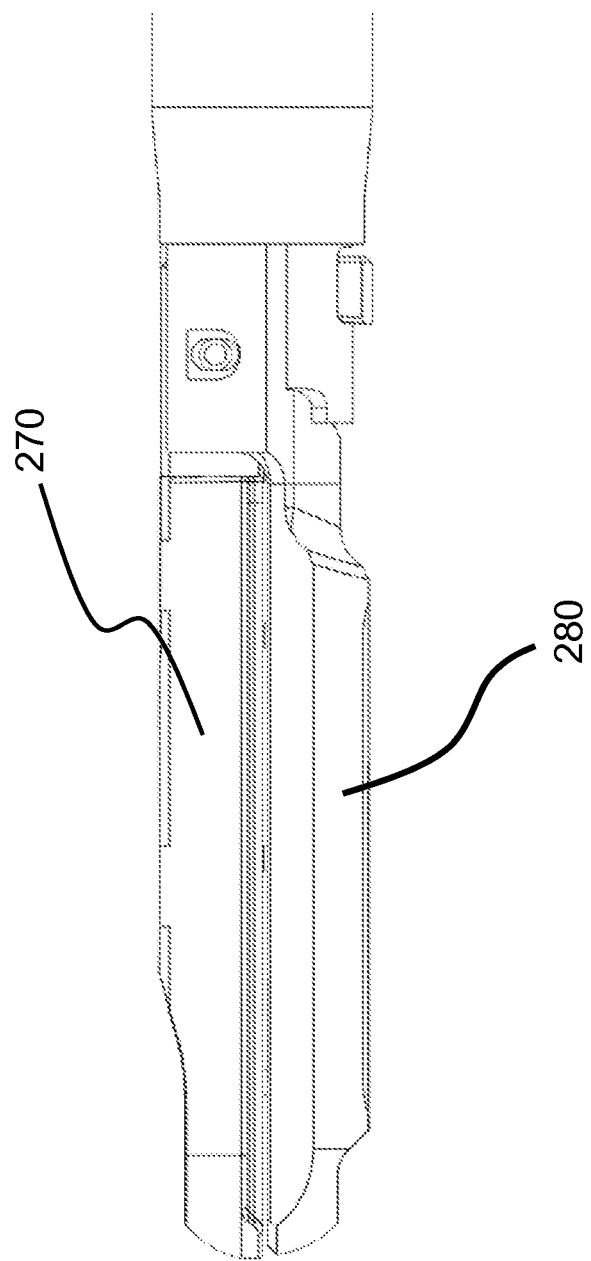
FIG. 26 is a side view of a distal end of an electrosurgical device in accordance with various embodiments of the present invention.

Referring now to FIGS. 7 and 8, the controller 44 includes RF smoother or smoothing modules or circuitry 68 to remove noise and/or extrapolate a smooth modulated DC signal representative of the RF energy being outputted (e.g., voltage, current, power and/or phase). An exemplary RF energy before and after the RF smoother are shown in FIGS. 19-20. In one embodiment, a data sampler 69 collects raw, evenly spaced data values from the analog to digital (ADC) phase, voltage, current, and power channels as the measurements are taken, then the RF smoother 68 applies a smoothing algorithm to filter the raw values into the resulting smoothed values. Further analysis is performed to determine various points of interest or events, such as the phase minimum and zero crossing points. Those points of interest are passed to the event handler 67 to trigger state changes. The generator in one embodiment waits for specific points of interest or events to be reached before changing states.

In one embodiment, the RF smoother 68 detects the local minimum point in the smoothed phase data provided by the RF Smoother and this point of interest is passed to the event handler 67 that notifies the script operations engine 65. In one embodiment, the RF smoother detects the zero crossing indicated for example by an ADC reading equal to about half of the maximum ADC counts and this point of interest is passed to the event handler that notifies the operations engine 65. Input and output commands, interrupts and event detections are provided by a query/command interface 66.

In accordance with various embodiments, the operations engine 65 enables the generator to be configurable to accommodate different operational scenarios including but not limited to different and numerous electrosurgical instruments, surgical procedures and preferences. The operations engine receives and interprets data from an external source to specifically configure operation of the generator based on the received data.

The operations engine receives configuration data from a device database script file 101 that is read from a memory device on a device plug or key 102. The script defines the state logic used by the generator. Based on the state determined and measurements made by the generator, the script can define or set output levels as well as shutoff criteria. The script in one embodiment includes trigger events or indicators that include indications of short condition for example when a measured phase is greater than 70 degrees or an open condition for example when a measured phase is less than −50 degrees.

In one embodiment, the operations engine provides system states and user states. System states are predefined states that control or manage specific predefined operations or operation conditions of the generator, such as successfully applying RF energy or indicating an error. System states in one embodiment are a pre-defined set of configurations that the system can be in (e.g., idle vs. energized) and whose functions are hard-coded into the electrosurgical generator. For example, a RF Done state is a system state that indicates that an RF energy cycle has been completed without errors. User states provide a framework through which customized or specialized operations and values can be established by direction from an external source for a particular instrument, procedure and/or preference.

In one embodiment, the script sets forth the system states and their exit conditions, e.g., expiration times or directions to another state and where the user states begin. For each user state, operation parameters for the specific state can be defined such as power, voltage, and current settings or are carried over from a previous state. In one embodiment, the user states may provide device, operator or procedural specific states and in one embodiment, the user states may be provided for testing or diagnostics specific states.

An exemplary two user state process is shown as an example in FIG. 10. The process begins in a system state Idle (71). If the switch is pressed (asserted) (78), the generator transitions to the User State 1 (72). Based on the exit condition, the generator transitions to the next state, User State 2 (73) or one of the system states (e.g. RF_Done (74) or Error (75)). If there is no user state after User State 2, then the process transitions back to a system state other than the system state Idle which will then transition the generator back to the system state Idle.

The exit criteria or condition (79) for each state defines the logic path for the script based on measurements made by the generator and thus the generator transitions from user state to user state. However, if the exit condition does not match the expected logic path, the seal or operation cycle is considered to have not been successfully completed, and the system state Error (75) is achieved. If the exit condition does match the expected logic path or indicates completion of an operation cycle, the operation cycle is considered to have been completed successfully, and the system state RF_done (74) is achieved. In one embodiment, if the switch is released before the completion of the fuse cycle, the system state Switch_Release (76) is achieved. In accordance with various embodiments, additional system states can be predefined to handle other general system errors or unexpected deviations from the expected logic path such as a timeout state indicating a maximum time to complete a fuse or operation cycle has been exceeded. Additionally, although only two user states are shown, the generator is expandable and configurable to include additional user states to provide an expanded logic path for a particular or a range of electrosurgical instruments, procedures and/or preferences.

Through the scripts, individual parameters or conditions pertaining to the electrosurgical or fusion process may be set. For example, acceptable impedance levels for an electrosurgical instrument prior to RF energy activation, maximum voltage, current and power settings (and in one embodiment, for each corresponding user adjustable level settings (e.g., level 1-3)), switch assert and de-assert dwell times for activation and deactivation, and stuck button error times at initial connection and following the completion of an operation cycle.

In one embodiment, the operations engine provides at least 30 states, 5 system states and 25 user states that provide the operational control parameters and output characteristics. These characteristics define the voltage, current and power output ranges that can be the full scale of the generator's output ranges or any level below. Each state in one embodiment has the ability to provide operation conditions such as to enable or disable RF output, modify the RF output regulation levels, as well as recognize and act upon different events or control indicators based on for example time, voltage, current, power, or phase ($\phi$) or combinations of these values and transition to another user state, error state, or completion state. The data, in one embodiment, that the operations engine receives from the event handler or the RF smoother has been smoothed according to a double exponential smoothing algorithm or exponential moving average algorithm. Voltage, current, power and phase smoothing parameters can be set individually in the device script.

In one embodiment, every 1 ms, the data sampler reads and stores the ADC channel measurements, e.g., voltage, current, power and phase angle. After the ADC measurements are processed, the data sampler calls the RF smoother. The RF smoother smooths or filters the ADC measurements and then notifies the event handler. If the event handler (checking for example every 15 ms) finds that a specific event or indicator has occurred, the event handler notifies the operations engine 65. After the operations engine has processed the event, it sets up the event handler for the next series of event evaluations.

The event handler in one embodiment is configured to evaluate a set of script events as defined by the device script. A script event is a grouping of postfix (Reverse Polish Notation (RPN)) tokens which describe a Boolean equation. The operations engine 65 provides the event handler with a port corresponding to a device script database and with a script state 68. The event handler evaluates that state and each event in that state in which each event is described by a Boolean equation. The event handler calculates the value of the Boolean equation. If any event evaluation in the state is found to be true, the event handler notifies the script operations engine, indicating that an event in the particular state was encountered, and providing the next location in the device script database where the script is to continue execution. If no event is found, then the event handler does not notify the script operations engine. In one embodiment, the event handler is configured to evaluate up to 10 events per a given sample time in which events are evaluated sequentially.

The event handler obtains timer values from a system timer 70 and switch events (press, release) 72 from a connected device and simulated switch events from the diagnostic port 71. The event handler also checks for time based events, such as a global timeout or state timeout and other recoverable errors such as over-voltage or over-current conditions. In one embodiment, this check is done by reading and comparing various ADC values to limits set by the device script.

The operations engine in one embodiment receives and installs the device script database file into a predefined device script database storage location in memory. During script development, the script compiler compiles the script source file into the device script database, containing among other things event data stored in RPN notation and state instructions. Prior to installation, the operations engine checks the device script database, i.e., the compiled script, for errors. In one embodiment, operations engine checks each token in the RPN data for values "out of range", that a Boolean value is returned and that there is only one RPN token remaining on the stack when the token count is at the end of the RPN data.

Referring now to FIG. 9, in accordance with various embodiments, a device is plugged into the tool port of the generator. The operations engine authenticates the device, which indicates that the integrity of the device memory and script has not been compromised. If the device passes authentication, the operations engine verifies the script database, which indicates that the script database was built correctly. If the script database is verified as valid, the operations engine begins script execution. (The start section of the IDLE state is set as the row number in the script table to begin running at.)

In operation, the operations engine reads commands from the script database. When the operations engine must wait for an event, the operations engine instructs the event handler with which events to identify and waits. When an event is identified by the event handler, i.e., event evaluation is true, the event handler notifies the operations engine and the event handler is disabled from further event evaluation for the tool port until the operations engine commands the event handler again. In one embodiment, the event handler is interrupted from a timer at least once per 20 ms or from ADC data being to evaluate events. The operations engine resumes execution when it is notified by the event handler that an event has been triggered.

The fusion process could be terminated (a) at a fixed and absolute resistance (for example 2 k Ohms), which would neglect both the size and type of tissue, (b) at a specific multiple of the time where the ohmic resistance is minimal, (c) at a specific multiple of the time where the ohmic resistance is the same as the initial one, or (d) at a specific multiple of the time where the ohmic resistance is a certain factor of the minimal one. However, considering burst pressure of fused arteries and thermal spread, the termination of the fusion process is determined to be in the flattened part of the impedance curve. As can be seen in FIGS. 12-20, however, this region is also an inexact range for impedance measurements. Similarly, each succession of (a) to (d) becomes better in determining the end-point of the fusion time (resulting in the highest desired bursting pressure with the least desired thermal spread). Utilizing the ohmic resistance only as termination criterion can lead to incomplete results. This can be more pronounced when fusing differently sized tissues (even of same nature).

In one aspect, the determination of the end-point of the fusion process is given by monitoring the phase shift of voltage and current during the fusion process. Unlike impedance, the phase shift changes much more pronounced at times where fusion of tissue completes, and hence offers a more sensitive control value than the impedance. However, for various types of tissue, reaching a high end of the phase range can lead to excessively long fusing times. Accordingly, as will be described in greater detail below, the application of RF energy via an electrosurgical generator in conjunction with the measuring or monitoring of phase shift are provided to fuse vessels and tissue in accordance with various embodiments of electrosurgical system.

As such, the instrument generating the seal, fusion or connection of the tissue provides atraumatic contact to the connecting tissue and provides enough burst pressure, tensile strength, or breaking strength within the tissue.

In one embodiment, the generator initially determines the initial instrument impedance and/or capacitance (e.g., during plug-in of the instrument connector to the electrosurgical generator), where tolerances/changes in the instrument characteristics are then accounted for in the tissue measurement and endpoint determination process. This can allow for tissue measurement values which are independent of the ohmic and capacitive values and/or tolerances of a specific electrosurgical instrument.

Figure 11A:
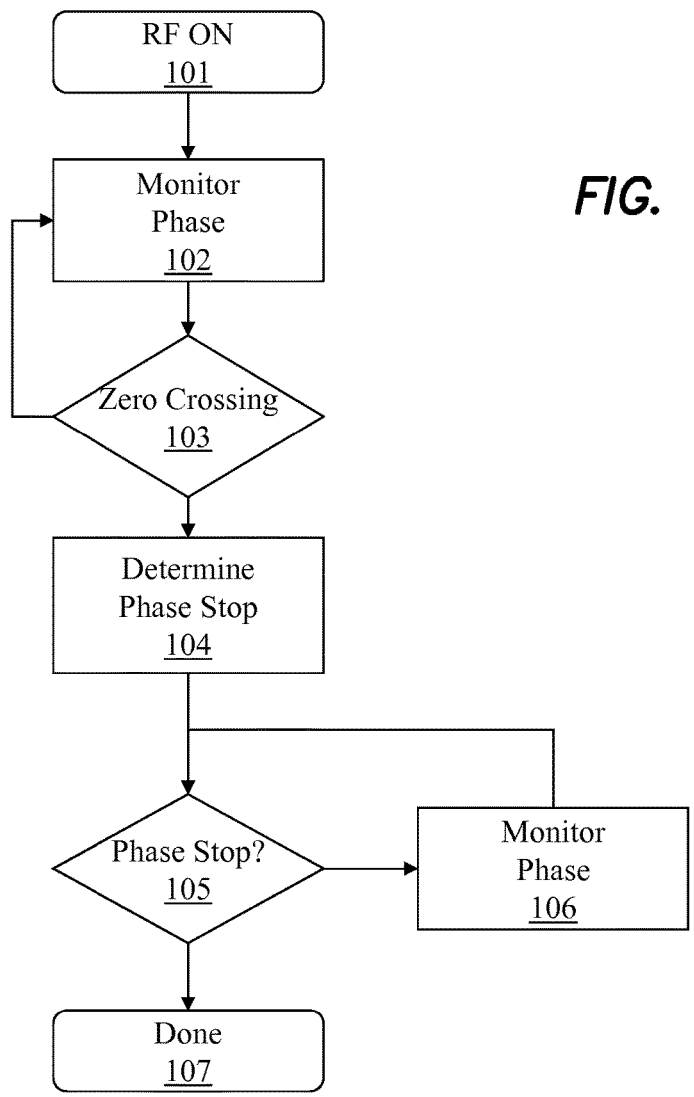
FIGS. 11A-11B are flow charts illustrating operations of an electrosurgical system in accordance with various embodiments of the present invention.
Figure 11B:
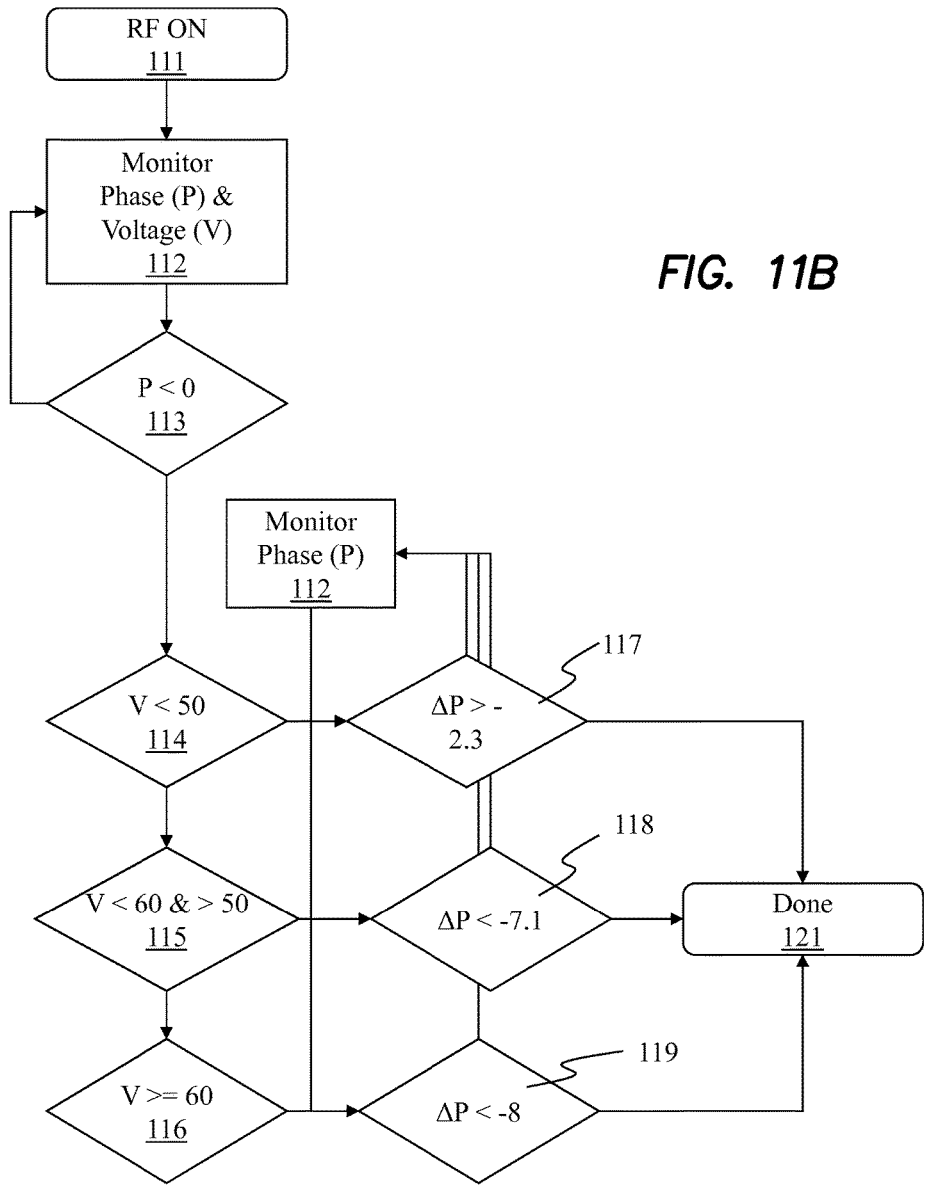
Figure 12:
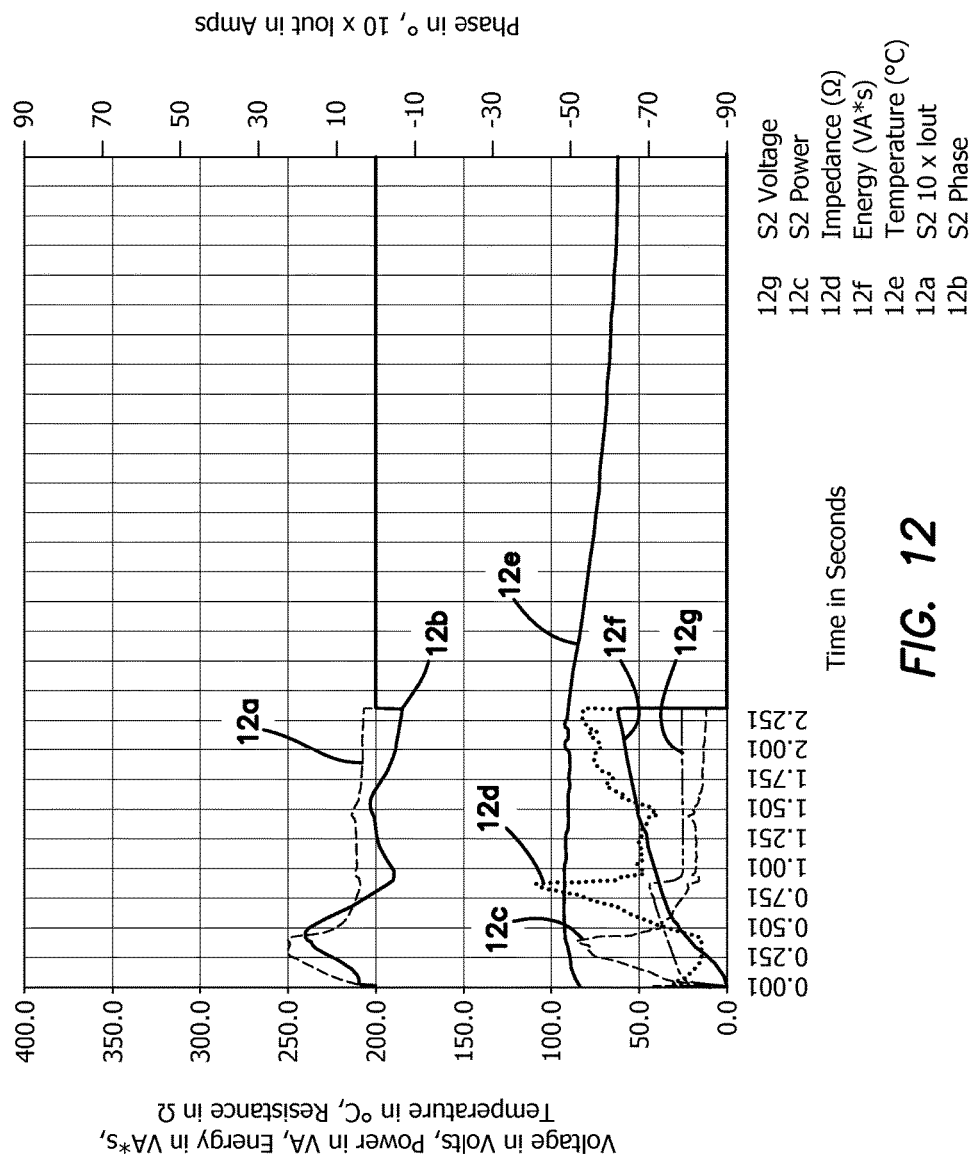

Exemplary RF energy control process for the electrosurgical generator and associated electrosurgical instrument for fusing tissue in accordance with various embodiments are shown in FIGS. 11A-11B. In one embodiment, RF energy is supplied by the generator through the connected electrosurgical instrument or tool (101). The generator monitors at least the phase and/or change of phase of the supplied RF energy (102). If a phase zero crossing or polarity change from positive to negative or negative to positive is encountered (103), a phase stop is determined (104). The phase stop in one embodiment includes a predefined phase angle and/or change of phase angle based on a determined tissue property such as size, permittivity, conductivity and/or applied voltage, current and/or power. The generator continues to monitor at least the phase and/or change of phase of the supplied RF energy (106). If the phase stop (105) is reached or exceeded, the process is done or termination procedures are initiated and/or RF energy supplied by the generator is stopped (107).

In one embodiment, prior to the start of the process, impedance is measured to determine a short or open condition through a low voltage measurement signal delivered to a connected electrosurgical instrument. In one embodiment, a passive impedance measurement is used to determine if the tissue grasped is within the operating range of the electrosurgical instrument (e.g., 2-200Ω). If the initial impedance check is passed, RF energy is supplied to the electrosurgical instrument. In one embodiment, voltage of the RF energy is applied (111) in a ramping fashion starting from 25% to at most 80% of a global setting or, in one embodiment, an user selected level (e.g., 27.5-88V for level 1, 25.0-80V for level 2 and 22.5V-72V for level 3).

Voltage and phase of the applied RF energy are continuously measured (112). When the phase measurement equals zero or transitions from positive to negative (113), voltage at that point is held constant at that voltage or at a predetermined voltage. In one embodiment, the zero or polarity crossing is used to determine the size of the tissue and select the appropriate path for completing the fusion cycle. In one embodiment, the voltage level of the ramp at the zero-crossing is used to determine the size of the tissue and then the appropriate path. It has been noted that the time taken to reach the phase zero-crossing can be associated with or correlate to the amount of water or moisture being removed from the tissue at that point and the tissue size.

In accordance with various embodiments, if the voltage level is less than 50% of the selected level at the phase zero-crossing (e.g., level 1: voltage<55V; level 2: voltage<50V; level 3: voltage<45V), tissue size is determined to be small (114). If the voltage level is less than 60% and greater than 50% of the selected level at the zero-crossing (e.g., level 1: 55 V<voltage<66 V; level 2: 50 V<voltage<60V; level 3: 45V<voltage<54V), tissue size is determined to be medium (115). If the voltage level is greater than or equal to 60% of the selected level at the zero-crossing (e.g., level 1: voltage≥66 V; level 2: voltage≥60V; level 3: voltage≥54V), tissue size is determined to be large (116). Based on the tissue size determination being medium or large, the voltage of the applied RF energy is held constant at the level at the zero-crossing. In accordance with various embodiments, based on the tissue size determination being small, the voltage of the applied RF energy is set to a predefined voltage and in one embodiment is set to 22 V. The predefined voltage in one embodiment is less than the voltage level based on the tissue size determination being medium or large.

Figure 13:
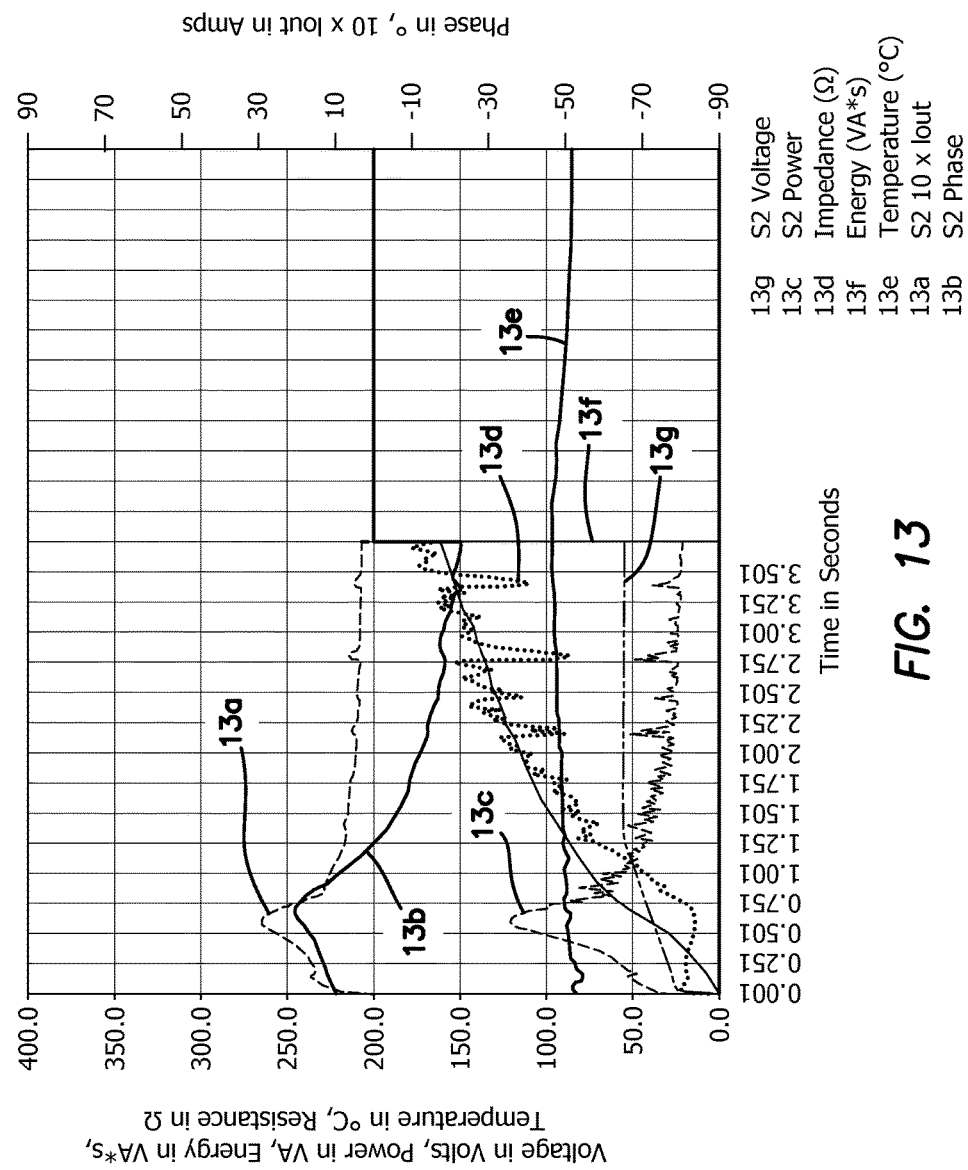
Figure 14:
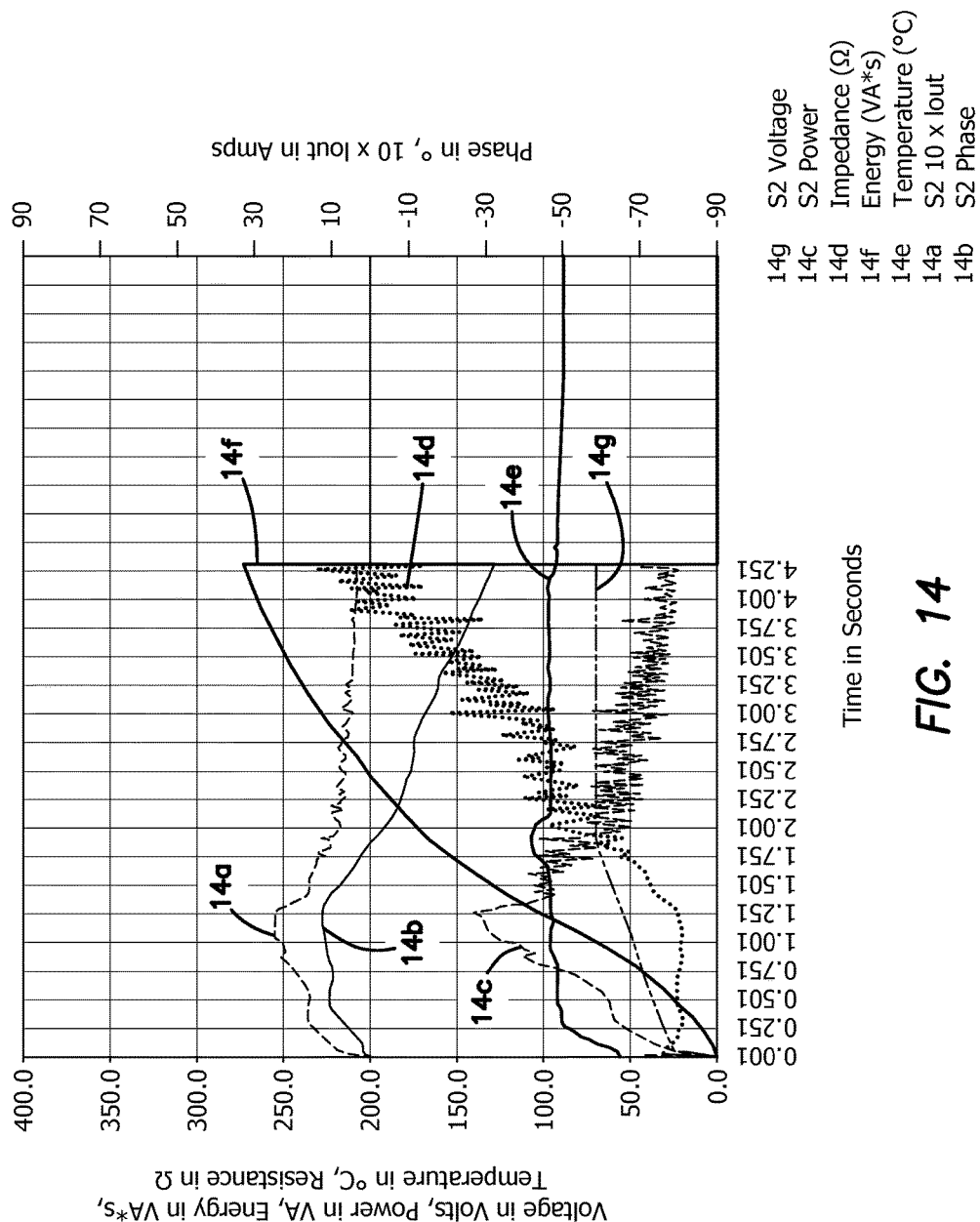

If the monitored phase and/or change of phase equals or is less than the selected predetermined phase and/or change of phase, electrosurgical energy is stopped (121). In one embodiment, if the calculated phase does not reach this phase stop within a set time, e.g., three, three and quarter or 4 seconds, electrosurgical energy is stopped. In one embodiment, if tissue size is determined to be small, the phase stop and/or change of phase stop is set to phase <−7.0° and/or change of phase <−2.3°/s (117). An exemplary graphical representation of RF energy successfully fusing tissue with a tissue size determined to be small is shown in FIG. 12. Also, as illustrated, phase 12b is shown relative to other tissue readings or indicators such as current 12a, power 12c, impedance 12d, temperature 12e, energy 12f and voltage 12g. If tissue size is determined to be medium, the phase stop and/or change of phase stop is set to phase <−23.0° and/or change of phase <−7.1°/s (118). An exemplary graphical representation of RF energy successfully fusing tissue with a tissue size determined to be small is shown in FIG. 13. Also, as illustrated, phase 13b is shown relative to other tissue readings or indicators such as current 13a, power 13c, impedance 13d, temperature 13e, energy 13f and voltage 13g. If tissue size is determined to be large, the phase stop and/or change of phase stop is set to phase <−32.0° and/or change of phase <−8.0°/s (119). An exemplary graphical representation of RF energy successfully fusing tissue with a tissue size determined to be small is shown in FIG. 14. Also, as illustrated, phase 14b is shown relative to other tissue readings or indicators such as current 14a, power 14c, impedance 14d, temperature 14e, energy 14f and voltage 14g. Additionally, although shown in FIGS. 12-14, in various embodiments, the generator is configured to not measure or calculate one or more of the indicators or readings, e.g., temperature or energy, to reduce operational and power parts, costs and consumptions of the generator. The additional information or readings are generally provided or shown for context purposes.

In accordance with various embodiments, phase is monitored in conjunction with current for open and short events while RF energy is being applied and in one embodiment after phase and/or change of phase stop or endpoints is reached to evaluate or determine if a false indication of fusion (caused by an open or short) has been reached.

In accordance with various embodiments, the generator is configured to provide additional regulation of various parameters or functions related to the output of the RF energy, voltage, current, power and/or phase and the operations engine is configured to utilize the various parameters or functions to adjust the output of RF energy. In one exemplary embodiment, the control circuitry provides additional regulation controls for direct regulation of phase in which voltage, current and/or power output would be adjusted to satisfy specified phase regulation set points provided by the operations engine.

In accordance with various embodiments, the generator utilizes the measured values of voltage, power, current and/or phase, e.g., control indicators, to recognize and act or perform operation conditions. In various embodiments, additional measurements or calculations based on the measured values related to RF output regulation circuitry are provided by the script or operations engine to recognize and act upon additional or different events related to or trigger by the additional measurements or calculations relative to other measurements or thresholds. The additional measurements in one embodiment include error signals in combination with a pulse width modulation (PWM) duty cycle used to regulate the output of voltage, current and/or power or other similar regulation parameters. Different or additional events or indicators that could be identified and triggered in various embodiments could be transitions from one regulation control to another regulation control (e.g. current regulation to power regulation).

Figure 15:
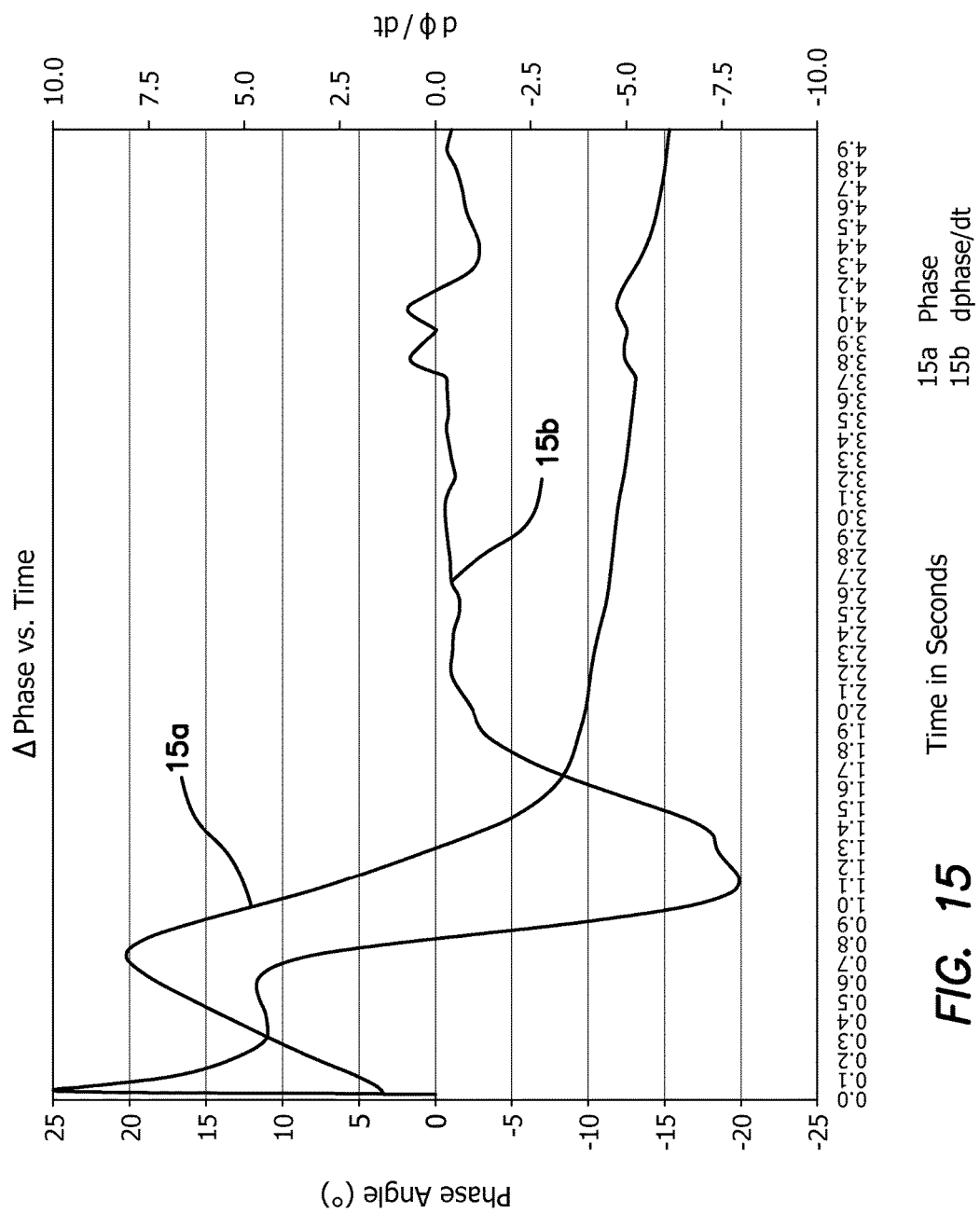

In accordance with various embodiments, the generator provides or conducts calculations to directly measure the rate of change of voltage, current, power and/or phase. For example, FIG. 15 provides exemplary graphical representation of phase 15a of the RF energy in relation to change of phase of RF energy 15b. The generator in one embodiment based on these calculations or direct measurements can recognize and act upon different events related to the RF output and electrical characteristics of the tissue during a fuse cycle.

Figure 16:
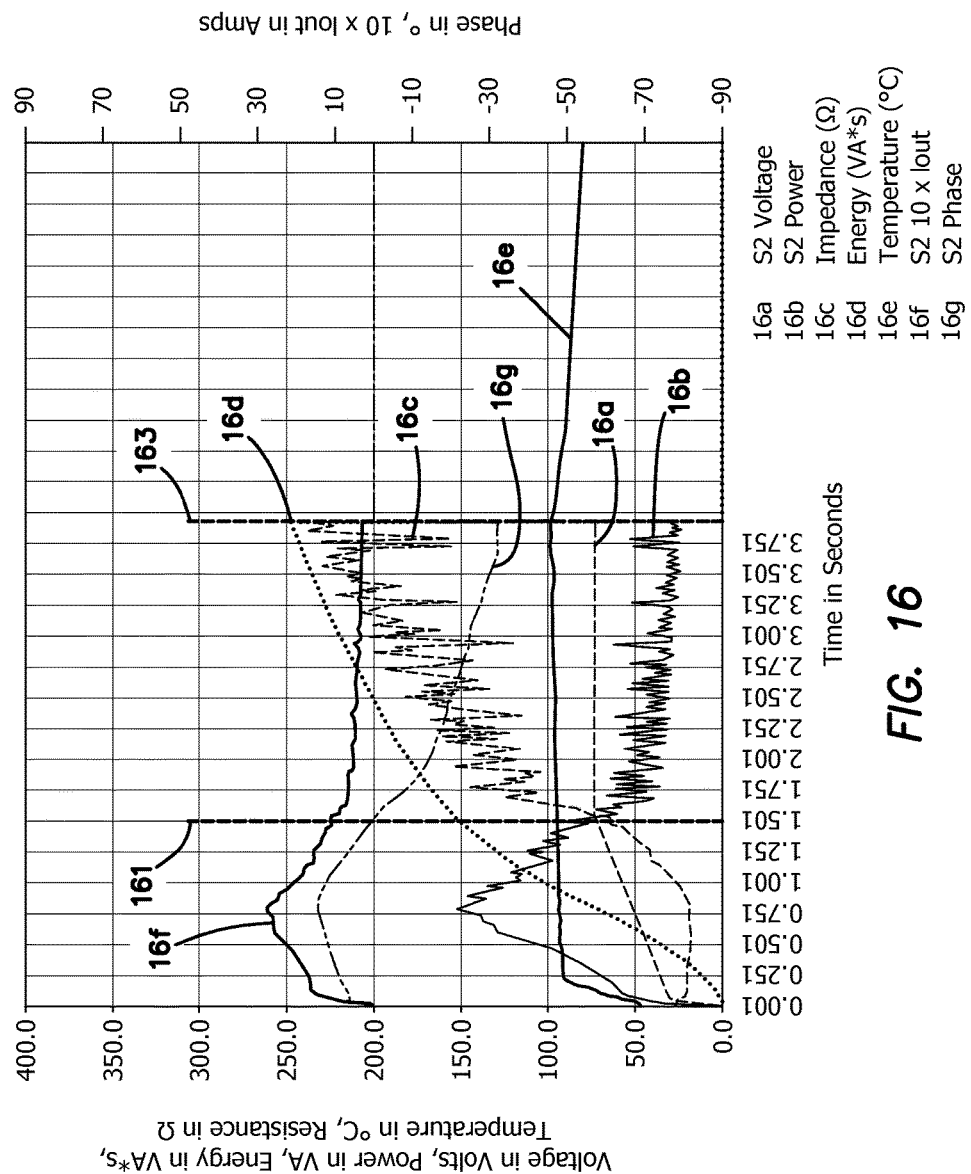

In accordance with various embodiments, the predetermined completion indicator can be varied or modified by the operations engine. In one embodiment, during a given fuse cycle, a tone (or other indicator) sounds at a phase threshold that is determined to be equivalent to a 7 psi (3× systolic pressure) seal 161 and then RF energy continues to be applied to the vessel to a phase threshold that is determined to be equivalent to a higher burst pressure (e.g. 20 psi) 163 at which point RF energy is automatically terminated. An exemplary graphical representation of RF energy fusing tissue utilizing seal pressure determinations is shown in FIG. 16. Also, as illustrated, phase 16g is shown relative to other tissue readings or indicators such as voltage 16a, power 16b, impedance 16c, energy 16d, temperature 16e and current 16f. In accordance with various embodiments, instead of or in addition to phase angle being used as a predetermined completion indicator or for other thresholds, time, voltage, current and power as well as conditional combinations thereof could be used.

In one embodiment, the user can release the activation button at any time between the initial tone and the end tone. This provides the surgeon with some degree of control with regards to the amount of RF energy is being applied to the tissue. For example, for thin, non-vascular tissue, a surgeon may release the button closer to the initial tone rather than wait for a subsequent tone. Similarly, for larger tissue, a surgeon may release the button much later than the initial tone or closer to a subsequent or end of cycle tone to thereby continue to apply RF energy longer.

In one embodiment, phase angle setting is user accessible and adjustable. By adding a phase level setting parameter, the phase trigger thresholds could be tied to percentages or a multiple (positive or negative) of the phase threshold. As such, the user could adjust a fuse cycle time, e.g., shorter and longer fuse cycles (e.g., Level 1 (171), Level 2 (172), and Level 3 (173)).

|  | Level 1 | Level 2 | Level 3 |
| --- | --- | --- | --- |
| Phase Setting | 30 | 60 | 90 |
| Phase endpoint determined by script (e.g. 33%) | 10° | 20° | 30° |

Figure 17A:
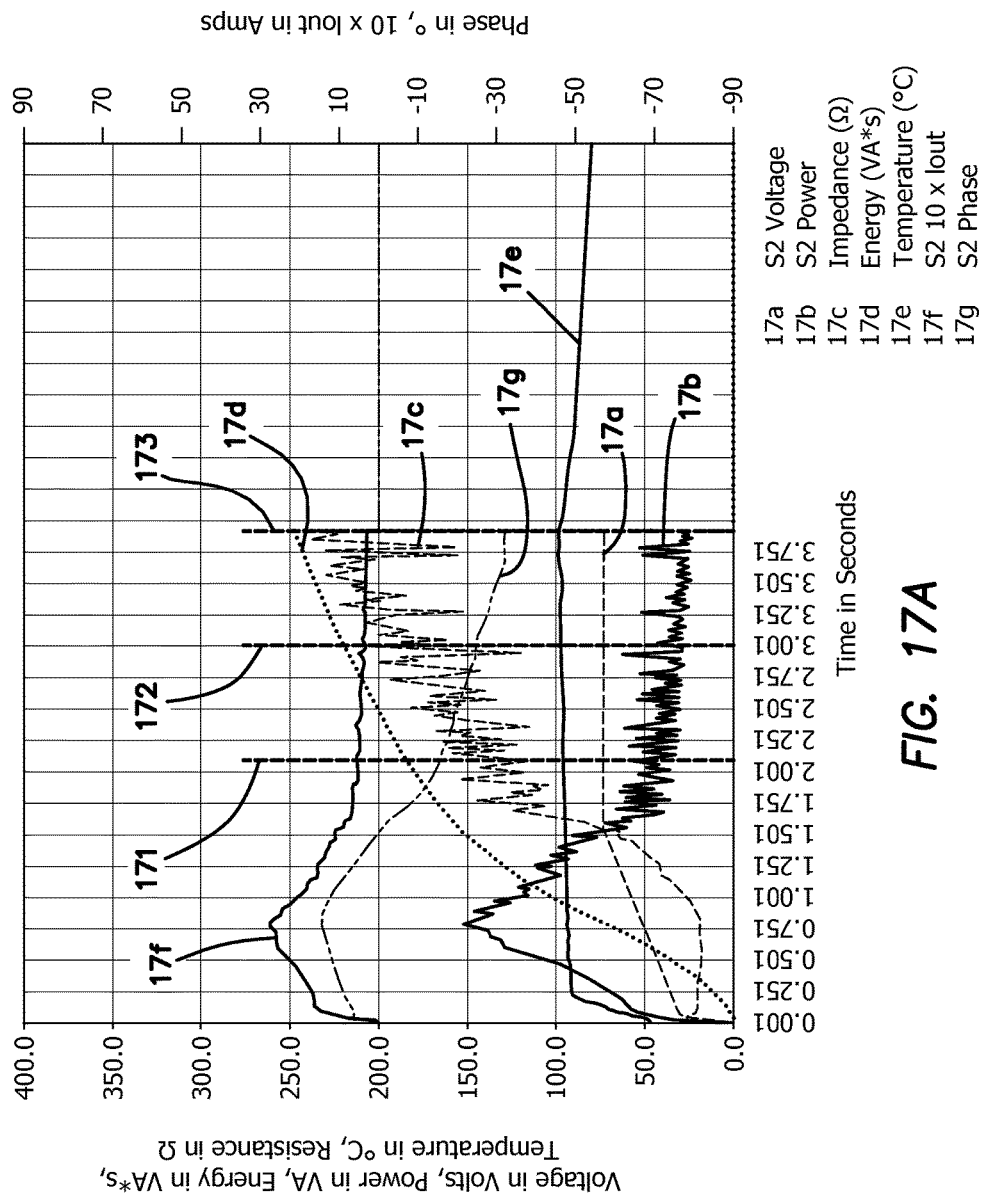

An exemplary graphical representation of RF energy fusing tissue utilizing user adjusted phase levels 171, 172, 173 is shown in FIG. 17A. Also, as illustrated, phase 17g is shown relative to other tissue readings or indicators such as voltage 17a, power 17b, impedance 17c, energy 17d, temperature 17e and current 17f.

Figure 17B:
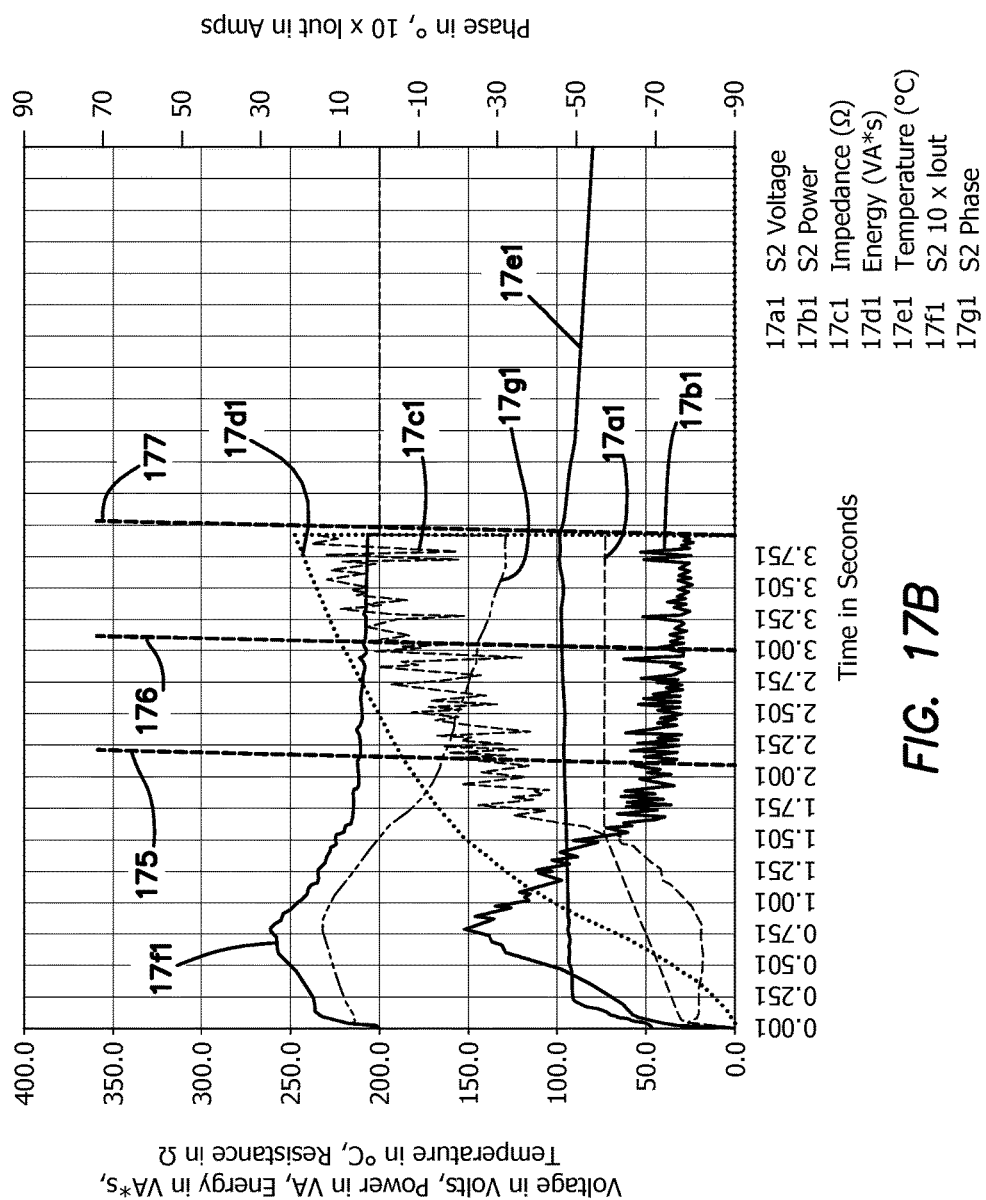

An additional way for providing alternate endpoints or alternative RF output delivery paths is to provide additional or alternative script logic paths based on the output level settings. This could also adjust a fuse cycle time, e.g., shorter or longer seal cycles that are user adjustable (e.g., Level 1 (175), Level 2 (176), and Level 3 (177)). An exemplary graphical representation of RF energy fusing tissue utilizing additional or user level adjusted script logic paths 175, 176, 177 is shown in FIG. 17B. Also, as illustrated, phase 17g1 is shown relative to other tissue readings or indicators such as voltage 17a1, power 17b1, impedance 17c1, energy 17d1, temperature 17e1 and current 17f1. Additionally, although shown in FIGS. 16-17B, in various embodiments, the generator is configured to not measure or calculate one or more of the indicators or readings, e.g., temperature or energy, to reduce operational and power parts, costs and consumptions of the generator. The additional information or readings are generally provided or shown for context purposes.

Figure 18:
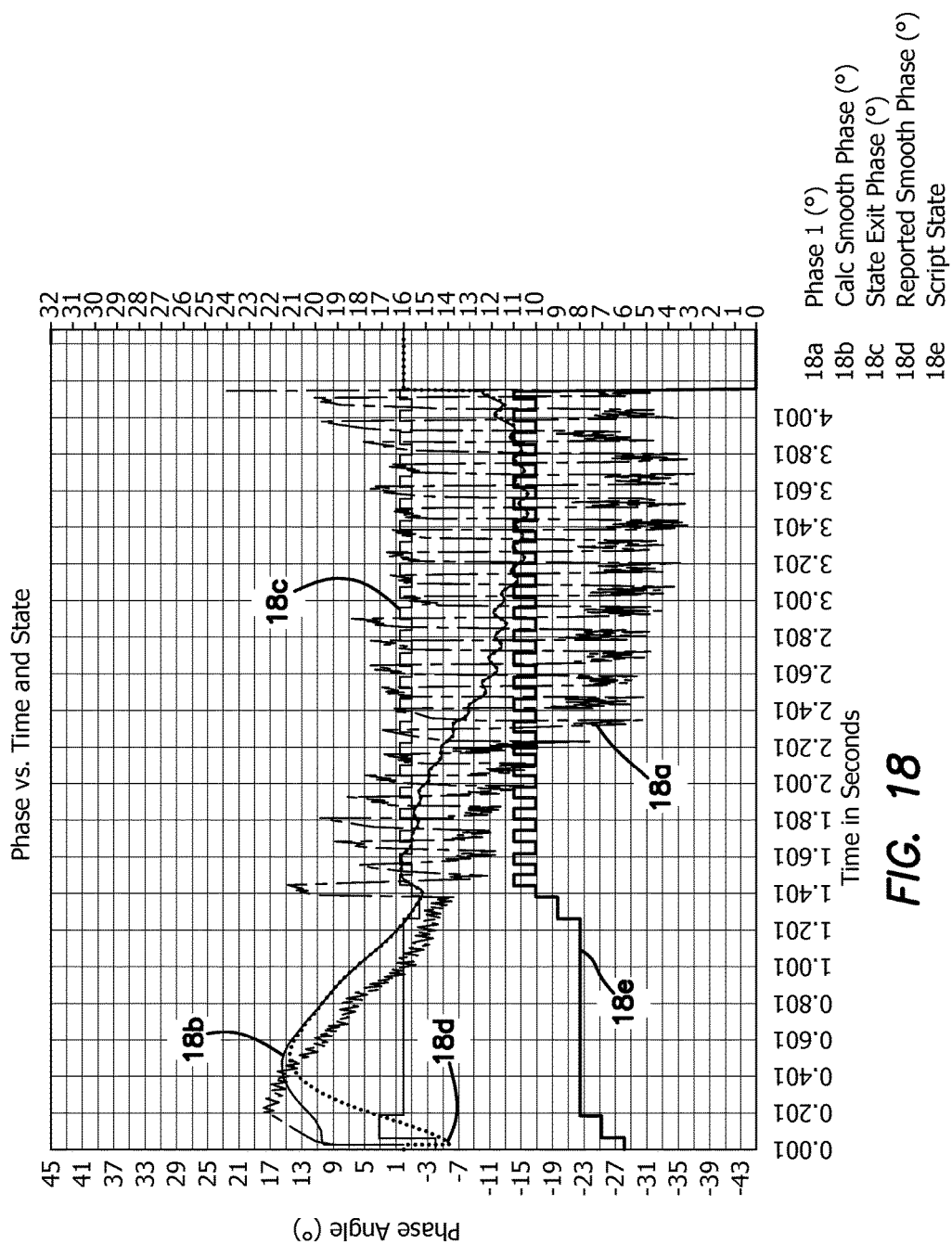

As provided in various embodiments, the operations engine provides the ability for the generator to operate between two or more states 18e. State transitions can be triggered by time, voltage, current, power or phase 18a, 18b, 18d and could also be used for an exit state 18c. In one embodiment, keeping a running state count of how many states have been cycled through would be an additional trigger for exiting a particular state. Alternative fuse cycles could also be defined using additional states or state counts that could include for example the cutting of tissue depending on RF output levels and electrosurgical instrument geometry. An exemplary graphical representation of RF energy fusing tissue utilizing script states is shown in FIG. 18.

In accordance with various embodiments, the RF Amplifier is configured to convert a 100 VDC signal from a power supply to a high power sinusoidal waveform with a frequency of 350 kHz, which will be delivered to the ABDI and eventually the connected electrosurgical tool. The amplitude of this signal in one embodiment is determined by a duty cycle of a plurality of input signals from the controller.

The RF Amplifier in one embodiment is configured with circuitry to ensure that there is dead time between PWM signals to prevent the PWM signals from the controller to be both ON at the same time. A 1:2 transformer of the RF Amplifier provides isolation between the PWM signals driving an H-bridge and a two stage low-pass filter. The output of the filter is a continuous 350 Khz sinusoidal waveform. The RF Amplifier includes a plurality of relays that are set by the controller to direct the 350 Khz signals from the output of the filter circuit to the device ports of the ABDI.

The RF Amplifier in accordance with various embodiments includes a plurality of shunt resistors, e.g., two shunt resistors for each of the device port. Voltage and current are measured across the resistors and in one embodiment are provided to two independent RF Sense. Relays on the RF Amplifier are set by the controller FPGA to direct a tissue measure signal from the controller to the device ports. In addition, a transformer is provided to isolate the tissue measure signal from the device ports. Power supply control signals pass through the RF Amplifier to the controller and in one embodiment the RF Amplifier includes an overcurrent detection circuit to determine if current supplied exceeds a specific threshold and/or a voltage monitoring circuit to determine if voltage supplied exceeds a specific threshold. PWM signals, RF energy shutdown signals, RF Sense control signals and relay control signals are supplied from the controller to the RF Amplifier. RF Sense analog signals, various RF sense fault signals, power supply control signals, passive measurement signals and standby power signals are supplied from the RF Amplifier to the controller.

In one embodiment, the RF Amplifier includes gate drive circuitry that takes at least two, 180° out of phase, 350 kHz PWM signals from the controller, to create non overlapping PWM signals that are fed into gate drivers in a power stage to generate the output RF signal or energy. Non-overlapping signals prevent damage to components in the power stage. Before the signals enter the power stage they are isolated to separate a noisy power ground from a quiet signal ground. The PWM signals at the power stage are fed into the gate drivers which take lower power PWM signals and produce high current drive input signals to the MOSFETs.

The controller provides two PWM signals with a certain pulse width depending on the desired RF output. The H-Bridge topology utilizes at least four gate drive signals to drive MOSFETs in the circuit. These four signals are attained by generating inverted counterparts for the two PWM signals. In addition, the RF Amplifier prevent a pair of signals (i.e. a first PWM signal and an inverted/second PWM signal) to be HIGH at the same time. Having both signals HIGH at the same time may potentially cause a shoot-through condition which can potentially damage components of the generator.

Two RC circuits in one embodiment of the RF Amplifier ensure that there is a dead time where both signals are off. Similarly, the other pair of signals also has two RC circuits to ensure dead time. The RC circuits have a shorter time constants to account for propagation delays.

In one embodiment, signals that can stop the propagation of PWMA and PWMB (i.e. a first PWM signal and an inverted PWM signal) to the gate drivers independently are provided. For example, one such signal is generated by the controller FPGA and the other signal is generated by the microcontroller. The PWM signals continue to propagate through isolators which separate the noisy ground from the quiet ground, where all the high power switching circuit is referenced to. These signals control the gate drivers, which converts the lower power PWM signals and produce a signal with high enough current to force the MOSFETs into saturation. Resistor and diode circuits at the output of the gate drivers are tuned to achieve the desired rise and fall times.

PWM DAC SPI lines allow the controller FPGA to communicate with the PWM DAC. The PWM DAC uses a DAC with the SPI interface to create a 4.452 Volt output. This output passes through an op-amp buffer and then is switched at 700 kHz, 50% duty cycle to create a 700 kHz square wave. As such, the PWM DAC sets a DC level initially, e.g., at power up, that is switched at 700 kHz to create a square wave output. This signal is then fed to an integrator stage which results in a 700 kHz triangle wave at the output. In particular, the integrator circuit causes a slope proportional to the input voltage. The amplifier is the other half. This changes the square wave into a triangle wave. The output is a 700 kHz wave with a duty cycle proportional to the error output. This signal goes to the FPGA Combined PWM input and the FPGA alternates these pulses to create first and second PWM outputs that operate the FETs on the input side of the RF transformer.

In particular, by combining the resulting triangle wave with the error signals from an RF control loop, the resulting signal represents a pulse width modulated signal that is used to drive the RF amplifier. Since the RF amplifier includes a full H-bridge output stage, two drive signals, each 180 degrees out of phase with the other are used. The PWM Signal Controller in the controller FPGA takes in the combined PWM signal and splits it into two signals. During the first half of the 350 KHz output cycle the FPGA routes the combined PWM signal to the first PWM output, and the second PWM output is held at 0V. During the second half the FPGA routes the combined PWM signal to the second PWM output, and the first PWM output is held at 0V.

In one embodiment, the first and second PWM outputs which drive the RF amplifier are only enabled if the microcontroller has requested the RF energy to be ON, e.g., enabled the RF amplifier output. If fault is detected while RF energy is active or being supplied, the PWM signals can be immediately disabled and the microcontroller alerted.

The microcontroller is able to control the RF amplifier output level by sending the desired voltage, current and power levels to the controller FPGA. These levels or set points are used by an analog RF control loop circuit which regulates the output power of the amplifier to meet the set points.

The Power Stage Circuit is configured to take the PWM signals produced in the gate drive circuit and generate a continuous sinusoidal signal, which is passed off to a relay circuit. The PWM signals drive MOSFETs in the H-Bridge configuration. The output of the H-Bridge is connected to a 1:2 transformer via a decoupling capacitor and a fuse. The transformer isolates the +100V power supply from the energy output to the patient. The circuit operates such that a first state follows second state continuously to produce a rectangular pulse train with a 0V offset. When the first state occurs, current passes through the transformer and exits the transformer. This produces the positive portion of the resulting waveform. When the second state occurs, current moves through the transformer in the opposite direction. This produces the negative portion of the resulting waveform. When PWMA and PWMB are either HIGH or LOW at the same time, the resulting waveform goes to 0V. After the transformer, this signal is passed off to a two-stage LC filter to produce a continuous sinusoidal waveform.

The two-stage LC filter is a low pass filter designed to provide a 0 dB gain at 350 kHz. The load resistance is the resistance across the tissue being sealed. A series capacitor in one embodiment is placed in order to minimize the possibility of neuromuscular stimulation.

In various embodiments, the controller includes a microcontroller that is generally responsible for overseeing the RF energy configuration and activation and the user interface. The controller also includes a Field Programmable Gate Array (FPGA) that is generally responsible for supporting the microcontroller by proving access to analog data and supervising the control circuits. The controller in one embodiment also includes a plurality of complex programmable logic devices (CPLDs) for health monitoring.

The microcontroller in one embodiment has an interface to the FPI to provide a user interface and indicate fault conditions/alarms, an interrupt input that indicates that a fault condition has been detected and an interrupt input that indicates that a front panel switch has changed states. The controller FPGA has parallel access to analog and control data, access to the front panel switches and an output that indicates a change in their state, and access to Device 1 and 2 inputs and outputs. In one embodiment, the controller FPGA has an active serial configuration interface for programming the FPGA and, in one embodiment, is the master for a system SPI communication bus for read and write access to the controller CPLDs and the RF Sense FPGAs.

The controller FPGA provides an interface to the ADC circuit that measures feedback voltage, current, power and phase, reads voltage and current set points and errors. The voltage, current, power and phase feedback voltages are measured redundantly by two groups of ADCs powered by different voltage references. The controller FPGA controls a DAC circuit that generates analog set points for voltage, current, and power.

The controller FPGA provides a clock, SPI DAC interface, and 700 kHz switch signal for the triangle wave generator and an input for the 700 kHz PWM circuit that generates 350 KHz+/−350 Hz outputs to a driver circuit of the RF Amplifier. The controller FPGA also detects when a device is connected. In various embodiments, the controller FPGA detects and provides outputs that indicate which device is active and PWM sync signals that are 90° out of phase (sine and cosine) to the RF Sense. The controller FPGA in various embodiments has an output to the microcontroller that indicates that a fault condition has occurred and has outputs to control the output/tissue measure relays.

The controller in one embodiment includes an analog control circuit to provide closed-loop control of the RF energy output using DAC outputs as set points and top voltage, current, and power RF Sense outputs as feedbacks. The output will be a combined PWM input to the FPGA.

The controller in one embodiment has redundant Complex Programmable Logic Device (CPLD) circuits generally responsible for detecting error conditions and shutting off the output when they occur. Each CPLD circuit is configured to have an output that operates an independent circuit that disables the RF output (Gate Power Control circuitry). Additionally, each CPLD circuit is configured to have a digital representation (ADC) of the RF sense 1 and RF sense 2 voltage, current, power, and phase outputs from the RF Sense. If any of these signals exceed minimum or maximum limits the CPLD circuit will disable the RF output.

In one embodiment, the controller CPLDs control load switches that allow the controller to independently turn off supply voltage to gate drivers and eventually the supply of RF energy.

The controller includes a plurality of CPLDs for detecting faults/error conditions. The CPLDs monitor the same signals for redundancy. The analog inputs that come from RF sense, after passing through the filter stage, get multiplexed and the outputs are fed to ADCs. From there, the outputs pass to a digital isolator which is used a voltage level shifter. Output of digital isolators feeds directly into the CPLD's bidirectional I/O.

The CPLD detect differences between RF sense 1 and RF sense 2 analog voltages or values (voltage, current, power, and phase) obtained from a plurality of RF Sense circuitry, e.g., RF sense 1 and 2. When the magnitude of the difference between RF sense 1 and RF sense 2 is greater than a maximum error value, the CPLD generates a local fault. Examples of other faults are when either voltage or current feedback signals for the RF sense 1 or 2 exceed predetermined limits, when the phase relationship between the synchronization signals is not valid for the RF sense 1 or 2.

The controller in one embodiment includes a passive measure circuit that is configured to compute absolute impedance and phase of tissue in contact with the connected electrosurgical tool. The passive measurement circuit in one embodiment includes a calibration resistor circuit and is transformer isolated from the patient.

The controller includes passive measure circuitry that includes a plurality of sub-circuits; an impedance analyzer, a voltage reference, a low pass filter, and a measurement amplifier. This circuit is electrically isolated from the patient by a transformer and can be connected to a known value resistor for calibration.

The impedance converter and network analyzer has an AC output that set to 100 kHz and this output passes through a filter circuit that removes harmonics from the 100 kHz signal and provides a current source that can drive low impedance loads. The passive measure amplifier uses the impedance of the tissue as the feedback so that the output is proportional to the impedance of the tissue.

Referring to FIG. 9, the generator 10 receives script information from the electrosurgical device or instrument 20 when the device is connected. The generator uses this script information to define a number of states and the order of execution of the states.

The script source file or script information written by the device script author 100 and not resident on the instrument or the generator 10 is text or user readable. The script information is compiled using a script compiler 105 to generate a device script database or binary file (SDB) 101. The script binary file is transferred by a device key programmer 107 to a memory module that is connectable or incorporated into the electrosurgical instrument 20 via a device key 102. As the electrosurgical instrument is connected to the electrosurgical generator, the generator authenticates the script binary file and/or the instrument (108). The generator validates the script binary file (109) and if validated the operations engine utilizes the script initiated by the actuation by the connected instrument (110). Script source file in one embodiment is a text file containing a device script that is specific for a specific electrosurgical instrument, generator and/or surgical procedure. The script source file for a device in one embodiment includes information containing parameters and a script (states, functions, events) for the electrosurgical generator and/or electrosurgical instrument. After successful validation, the script compiler assembles data into a binary format that defines a state machine for use by the electrosurgical generator. Script compiler as shown in FIG. 9 in one embodiment is separate from the electrosurgical generator and is responsible for reading in text from the script source file and validating its contents.

When the memory module is inserted into the generator, the generator downloads a binary file that is stored in a ferromagnetic random access memory (FRAM) or microcontroller disposed within the module. The binary includes logic for implementing the above-described treatment algorithm. The generator includes firmware/software responsible for processing the binary to authentic the connected instrument and to execute the binary for performing the treatment algorithm. In this manner, the generator is configured to operate only with authenticated, compatible hand tools.

In one embodiment, instrument scripts or script database represent an instrument process for a specific or given instrument. The instrument scripts are stored on memory connected to or integrated with an instrument, the controller or a combination thereof. The event handler responds to specific events, such as a switch activation/de-activation, instrument positions or exceeding measurement thresholds. The operations engine based on the detected event if appropriate for a given event provides output to the connected instrument. In one embodiment, an event is a discrete change, as in a switch is asserted or de-asserted.

Script state is a block or set of script functions or operation conditions and script events or indicators. Script functions are configurable instructions for controlling the generator and/or the instruments. Script operators are logical and comparison operations performed during a script event evaluation. Script parameters are configuration data used by all states and events of a script and in one embodiment are declared in their own dedicated section of the script file. Script events are a discrete change in an electrosurgical generator measurement. When a Script Event occurs, for example, a sequence of script functions is executed.

In one embodiment, the controller has a specific or predetermined fixed instrument script for a specific input receptacle. As such, only this instrument script is used for the instrument connected to the particular input receptacle. The event handler receives and identifies instrument events or indicators, such as a switch activation/de-activation event or a measurement event (e.g., phase threshold exceeded). The operations engine formulates requests or operations to the RF amplifier to control RF output, output selection and/or selection of outputs. Other events or indicators detected include detecting hand and foot switches, jaw switches, phase over and phase under-after-over events, shorts and opens, instrument script states. Keywords in the scripts assist the operations engine to extract operational commands and data for instrument operation based on a detected event identified by the event handler.

The script in one embodiment controls the voltage and current output settings as well as sequences of voltage and current settings. Generally, a small blood vessel will fuse very rapidly while a large vessel may take several seconds. Applying a large amount of current to a small vessel may cause excess tissue damage, while using a small amount of current will take an unacceptably long time to perform the fusion function. In one embodiment to modify instrument performance the script can initially command a small amount of RF current, and if fusion endpoint is not reached in less than one second for example a high current is commanded to speed the fusion of a large vessel. Another script usage to modify instrument performance in one embodiment is to switch from one operation (fuse) to another operation (cut) and for example to reconfigure the instrument electrodes and ESG output which simplifies a multistep process such as fuse and cut. When the clinician starts the process the script will first setup the unit for the fusion, measure the tissue phase angle that indicates the fusion endpoint. RF power is delivered until the fusion endpoint is reached. The unit will then turn off RF power and indicate that fusion is complete. The unit then switches the electrodes to a cut configuration, sets the RF output for cut, and restarts the RF output. The cut operation is stopped by the clinician when the cut is completed.

In one embodiment, upon activation of a switch coupled to the instrument, the controller detects the switch closure, and authenticates the instrument or device, checks the instrument's expiration status, and/or initializes internal data structures representing the receptacle's instrument. A subsequent activation of the instrument switch initiates an event that causes the script to direct the generator to supply RF energy. The controller logs the usage to both the instrument and the generator. When the instrument is disconnected from the receptacle of the generator, the controller resets the information associated with the receptacle. The controller in one embodiment constantly monitors the generator for proper operation. Unrecoverable errors and faults are announced and further operation of the system is prevented. All faults are stored in the controller's memory and/or the instrument's memory.

Data from a specific procedure (e.g., from power-up to power-down) is stored on each instrument. The instrument additionally holds the data from a procedure, i.e., the number of instrument uses, the power setting and faults. Each instrument in one embodiment holds the information from all other instruments as well. Instrument memory includes some or all of the following parameters, but is not limited to these parameters: serial number of generator, time stamp, tissue assessment and endpoint setting for each instrument use, cut, fuse, power setting, duration of RF and endpoint (auto stop, fault, manual stop, etc.).

In accordance with various embodiments, the Script Engine controls RF activation through a Script Database driven state machine. The Script Database can be read into the Script Engine via the tool ports when a device is plugged in or via a diagnostic port. The Script Engine waits for an event to be recognized by a Script Event Handler, and then executes functions associated with the received and recognized event. In one embodiment, initially, after executing a sequence of functions that constitute a state's setup or a state's event actions, the Script Engine instructs the Event Handler to check for events and then waits for notification from the Event Handler that an event has occurred. As such, the Event Handler checks for any event or combination of events which would cause the script engine to transition from a present state to a new state.

The Script Engine in accordance with various embodiments performs run-time checks to ensure that the executing script cannot damage the generator. In one embodiment, a Script Database is a binary data block containing a tokenized encoding of a script file. A Script Database is loaded by an external task into one of two sections of FRAM or SRAM memory (a region for each of tool ports). Script Binary Database is a binary file generated from a Script File by the Script Compiler and executed by the Operations Engine to control the operation of the electrosurgical generator and/or the electrosurgical instrument.

As previously described and described throughout the application, the electrosurgical generator ultimately supplies RF energy to a connected electrosurgical instrument. The electrosurgical generator ensures that the supplied RF energy does not exceed specified parameters and detects faults or error conditions. In various embodiments, however, an electrosurgical instrument provides the commands or logic used to appropriately apply RF energy for a surgical procedure. An electrosurgical instrument includes memory having commands and parameters that dictate the operation of the instrument in conjunction with the electrosurgical generator. For example, in a simple case, the generator can supply the RF energy but the connected instrument decides how much energy is applied. The generator however does not allow the supply of RF energy to exceed a set threshold even if directed to by the connected instrument thereby providing a check or assurance against a faulty instrument command.

As described generally above and described in further detail below, various handheld electrosurgical instruments or instruments can be used in the electrosurgical systems described herein. For example, electrosurgical graspers, scissors, tweezers, probes, needles, and other instruments incorporating one, some, or all of the aspects discussed herein can provide various advantages in an electrosurgical system. Various electrosurgical instrument embodiments are discussed below. It is contemplated that one, some, or all of the features discussed generally below can be included in any of the embodiment of instrument discussed below. For example, it can be desirable that each of the instruments described below include a memory for interaction with the generator as previously described. However, in other embodiments, the instruments described below can be configured to interact with a standard bipolar power source without interaction of an instrument memory. Furthermore, although it is contemplated that certain aspects of these embodiments can be combined with certain aspects of other electrosurgical instruments within the scope of this application.

As discussed above with respect to FIG. 1, an electrosurgical instrument can include a memory. The memory can include a configuration device module. The configuration device module can store certain types of instrument data. For example the configuration device module can store operational parameters for the instrument, including software to be transferred to an electrosurgical unit upon successful electrical connection to the electrosurgical unit. These operational parameters can include data regarding various electrosurgical procedures to be performed by the instrument and corresponding energy level ranges and durations for these operations, data regarding electrode configuration of an instrument, and data regarding switching between electrodes to perform different electrosurgical procedures with the instrument. Advantageously, changes to instrument profiles and periodic instrument updates can be rapidly made without downtime to electrosurgical generators, as the data for instrument operation can reside in electrosurgical instrument itself, rather than the generator. Accordingly, updates can be made during instrument production.

The configuration device module can further store a data log comprising, for example, a record of information of each previous instrument use. For example, in some embodiments, the data log can contain timestamp data including an electrosurgical unit identifier, a log of electrosurgical procedures perform by the instrument, and a log of durations and energies applied to the instrument. In some embodiments, it can be desirable that use of a particular instrument is limited to a maximum usage period or number of procedures, especially where electrosurgical instrument has not been configured for sterilization and reuse. Accordingly, in some embodiments, the configuration device module can be configured to prevent operation of an instrument after a predetermined usage or number of procedures. In some embodiments, an instrument can comprise a mechanical lockout in addition to or in place of the data log, such as a breakaway single-use connector to reduce the possibility of unintended reuse.

The electrosurgical instrument in one embodiment has two separate electrodes capable of carrying RF energy (375 VA, 150V, 5 A at 350 kHz+/−5 kHz). The maximum output RF voltage is 150 Vrms, +/−7.5 Vrms. The maximum output RF current is 5 Arms, +/−0.25 Arms. The maximum output RF power is 375 VA, +/−18.75 VA.

In accordance with various embodiments, an electrosurgical instrument 20 is provided. The instrument 20 includes an actuator coupled to a rotatable shaft relative to the actuator. The elongate shaft has a proximal end and a distal end defining a central longitudinal axis therebetween. At the distal end of the shaft are jaws and at the proximal end is the actuator. In one embodiment, the actuator is a pistol-grip like handle. The shaft and jaws, in one embodiment, are sized and shaped to fit through a 5 mm diameter trocar cannula or access port.

The actuator includes a movable handle and a stationary handle or housing with the movable handle coupled and movable relative to the stationary housing. In accordance with various embodiments, the movable handle is slidably and pivotally coupled to the stationary housing. In operation, the movable handle is manipulated by a user, e.g., a surgeon to actuate the jaws, for example, selectively opening and closing the jaws. In various embodiments, the instruments comprise an advanceable cutting blade that can be coupled to a blade actuator such as a blade trigger of the actuator. A blade actuation mechanism can operatively couple the blade trigger to the cutting blade.

Attached to the distal end of the elongate shaft are jaws that comprise a first jaw and a second jaw. In one embodiment, a jaw pivot pin pivotally couples the first and second jaws and allows the first jaw to be movable and pivot relative to the second jaw. In various embodiments, one jaw is fixed with respect to the elongate shaft such that the opposing jaw pivots with respect to the fixed jaw between an open and a closed position. In other embodiments, both jaws can be pivotally coupled to the elongate shaft such that both jaws can pivot with respect to each other.

Attached to the first jaw is a conductive pad. In one embodiment, the isolated wire is routed to electrically couple the conductive pad on the first jaw to the wiring harness in the actuator. The isolated wire extends from the distal end of the protective sleeve which is housed at the proximal end of the second jaw and extends into the first jaw. The first jaw can have a slot positioned to receive the isolated wire. The isolated wire then extends through a hole in the first jaw and drops into a slot in a nonconductive portion. The isolated wire then extends to the distal end of the nonconductive portion and drops through to the conductive pad.

Turning now to some of the operational aspects of the electrosurgical instruments described herein, once a vessel or tissue bundle has been identified for sealing, the first and second jaws are placed around the tissue. The movable handle is squeezed moving the movable handle proximally with respect to the stationary housing. As the movable handle moves proximally it pushes a pull block. The pull block engages with a pull tube causing the pull tube to move proximally. Proximal movement of the pull tube pivots the first jaw towards the second jaw effectively clamping the tissue. The force applied to the tissue by the first jaw is translated through the pull tube and pull block to the movable handle. Once the preloaded force has been overcome, the movable handle will begin to move a sliding pin distally. When the preload on the spring has been overcome, the movable handle pivot point shifts from the sliding pin to the rear portion of the pull block where it contacts the movable handle. The sliding pin can advance distally because the preloaded force on the trigger spring has been overcome.

The continued manipulation of the movable handle pivots the movable handle to a location where the movable handle engages with a latch mechanism that maintains the movable handle in the engaged position and prevents the handle from returning to an opened position. From the engaged position, sealing radio frequency energy is applied to the tissue by depressing the power activation button. Once the tissue has been fused, the movable handle can be reopened by continuing proximal advancement to a position that allows the latch mechanism to disengage.

The force regulation mechanism reduces the risk that an extremely large amount of force is applied to the tissue. If too much force is applied to a vessel or tissue bundle, potential damage could occur. Thus, if a very small vessel or thin tissue bundle is clamped within the jaw, the instrument applies the minimum amount of force required to obtain a good tissue fuse. The same is true with a very large vessel or tissue bundle.

Once the tissue has been fused, the user can actuate the blade trigger. When the blade trigger is moved proximally, the blade lever pivots, forcing a push bar and a cutting blade to move distally. The cutting blade advances forward and divides the fused portion of the tissue. When the user releases the blade trigger, the blade spring resets the cutting blade to its original position. When the blade trigger has been returned to its original or initial position the user can continue to squeeze the movable handle to open the upper jaw. Continued proximal movement of the movable handle will disengage the latch mechanism to a position where the movable handle can be released.

The dimensions of the sealing surface are such that it is appropriately proportioned with regards to the optimal pressure applied to the tissue between the jaws for the potential force the device mechanism can create. Its surface area is also electrically significant with regards to the surface area contacting the tissue. This proportion of the surface area and the thickness of the tissue have been optimized with respect to its relationship to the electrical relative properties of the tissue. The jaws are arranged to maintain electrically significant spacing between the jaws in relation to the thickness of tissue held between the jaws.

As discussed above with respect to the electrosurgical system, in some embodiments, the electrosurgical fusion instrument can be used in a system which monitors various operational parameters and determines a radiofrequency endpoint based on phase angle.

With reference to FIGS. 21-40, in accordance with various embodiments, an electrosurgical fusion instrument or device is provided that in accordance with various embodiments is removably connectable to an electrosurgical generator. In the illustrated embodiment, the instrument includes an actuator 224 coupled to a rotatable shaft 226 relative to the actuator. The elongate shaft 226 has a proximal end and a distal end defining a central longitudinal axis therebetween. At the distal end of the shaft 226 are jaws 222 and at the proximal end is the actuator. In one embodiment, the actuator is a pistol-grip like handle. The shaft 226 and jaws 222, in one embodiment, are sized and shaped to fit through a 5 mm diameter trocar cannula or access port.

The actuator 224 includes a movable handle 223 and a stationary handle or housing 28 with the movable handle 223 coupled and movable relative to the stationary housing. In accordance with various embodiments, the movable handle 223 is slidably and pivotally coupled to the stationary housing. In operation, the movable handle 223 is manipulated by a user, e.g., a surgeon to actuate the jaws, for example, selectively opening and closing the jaws.

In accordance with various embodiments, the actuator 224 includes a force regulation mechanism that is configured such that in a closed configuration, the jaws 222 delivers a gripping force between a predetermined minimum force and a predetermined maximum force.

As part of the force regulation mechanism, the movable handle 223 is coupled to the stationary handle at two sliding pivot locations to form the force regulation mechanism. The movable handle has a first end including a gripping surface formed thereon and a second end 258 opposite the first end. The movable handle is coupled to a pin 256 adjacent the second end. In some embodiments, the movable handle can be integrally formed with a protrusion extending therefrom defining a pin surface. In other embodiments, a pin can be press-fit into an aperture in the movable handle. The pin can be contained within slots in the stationary housing, such as a corresponding slot formed in a right and/or left handle frames of the stationary housing. In some embodiments, the slots can be configured to define a desired actuation handle path, such as a curved or angled path, as the actuation handle is moved from the first position corresponding to open jaws to a second position corresponding to closed jaws.

The force regulation mechanism includes a biasing member such as a tension spring 257 that biases the pin in a proximal direction. In operation, as a predetermined force is exerted on by movement of the movable handle 223, a biasing force exerted by the spring is overcome, and the second end of the movable handle can translate generally distally, guided by the pin in the slots.

In accordance with various embodiments, the movable handle is slidably and pivotally coupled to the stationary housing 228 at a location between the first and second ends of the actuation handle. An actuation member such as a pull block 251 is coupled to the actuation handle. When the movable handle is moved proximally, the pull block also moves proximally and longitudinally, closing the jaws 222 thereby clamping any tissue between the jaws. The pull block 251 in accordance with various embodiments is rectangular having open top and bottom faces and a closed proximal end. The movable handle extends through the top and bottom faces of the pull block. An edge of the movable handle bears on the proximal end of the pull block such that movement of the movable handle relative to the stationary housing moves the pull block longitudinally. A distal end of the pull block in one embodiment is coupled to an actuation shaft such as a pull tube, bar, or rod, which can extend longitudinally along the elongate shaft 226. Thus, in operation, movement of the movable handle from the first position to the second position translates the pull block 251 longitudinally within the stationary housing, which correspondingly translates the pull tube generally linearly along the longitudinal axis with respect to the elongate shaft 226. Movement of this pull tube can control relative movement of the jaws 222.

In accordance with various embodiments, the actuator 224 includes a latch mechanism to maintain the movable handle 223 in a second position with respect to the stationary housing 228. In the illustrated embodiment, the movable handle comprises a latch arm 265 which engages a matching latch 267 contained within stationary handle for holding the movable handle at a second or closed position.

In various embodiments, the instrument comprises an advanceable cutting blade 271 that can be coupled to a blade actuator such as a blade trigger 225 of the actuator 224. A blade actuation mechanism can operatively couple the blade trigger to the cutting blade. In one embodiment, the blade actuation mechanism comprises a pivoting blade advancement link that transfers and reverses the proximal motion of the blade trigger 225 to a blade actuation shaft assembly, such as a push bar, coupled to the cutting blade. In operation, a user can move the blade trigger 225 proximally to advance the cutting blade 271 from a retracted position to an extended position. The blade actuation mechanism can include a biasing member such as a blade return spring 263 to bias the cutting blade into the retracted position.

The cutting component can be selectively moved between a proximal location and a distal location to cut tissue compressed between the jaws of the jaw assembly. In various embodiments, the cutting blade 271 can be a sharp blade, hook, knife, or other cutting element that is sized and configured to cut tissue between the jaws. In some embodiments, the cutting blade includes a first sharpened edge and a second sharpened edge on each of a proximal edge and a distal edge of the cutting blade to allow cutting of tissue when the cutting blade is moved either proximally or distally along a slot or channel in the jaws.

The actuator also comprises a wire harness that includes insulated individual electrical wires or leads contained within a single sheath. The wire harness can exit the stationary housing at a lower surface thereof and form part of the cabled connection. The wires within the harness can provide electrical communication between the instrument and the electrosurgical generator and/or accessories thereof.

In accordance with various embodiments, the actuator includes one or more leads attached to rotational coupling clips configured to allow infinite rotation of the shaft. In various embodiments, a switch is connected to a user manipulated activation button 229 and is activated when the activation button is depressed. In one aspect, once activated, the switch completes a circuit by electrically coupling at least two leads together. As such, an electrical path is then established from an electrosurgical generator to the actuator to supply RF energy to the leads attached to the rotational coupling clips.

In one embodiment, the actuator includes a rotation shaft assembly including a rotation knob 227 which is disposed on an outer cover tube of the elongate shaft 226. The rotation knob allows a surgeon to rotate the shaft of the device while gripping the actuator 224.

In accordance with various embodiments, the elongate shaft 226 comprises an actuation tube coupling the jaws 222 with the actuator and a blade actuation shaft assembly coupling the actuator with a cutting blade 271. In various embodiments, the blade actuation shaft assembly comprises a two-piece shaft having a proximal portion and a distal portion. The proximal portion of the blade shaft assembly terminates at a proximal end at an interface node. The interface node comprises a generally spherical protrusion portion which is adapted to engage the blade advancing lever. In other embodiments, the interface node can comprise other geometries such as cubic or rectangular prismatic protrusions. The proximal portion of the blade shaft is operatively coupled to the distal portion of the blade shaft assembly. The distal portion of the blade shaft can comprise a mount at its distal end for attachment of the cutting blade. In certain embodiments, both the proximal and distal portions of the blade shaft are at least partially positioned within a generally tubular section of the actuation tube.

In various embodiments, the actuation tube is housed within an outer cover tube. While the actuation tube is illustrated as a generally tubular member that can be nested within the outer cover tube, and that can have a blade actuation shaft nested within it, in other embodiments, a non-tubular actuation member can be used, for example, a shaft, a rigid band, or a link, which, in certain embodiments can be positioned generally parallel to the blade actuation shaft within the outer cover tube.

In accordance with various embodiments, attached to the distal end of the outer cover tube is a rotational shaft assembly comprising of two mating hubs and a conductive sleeve. The hubs snap together, engaging with the outer cover tube. In other embodiments, the hubs can be of a monolithic construction and configured to interface with mating features on the outer cover tube. The conductive sleeve can be attached to the proximal portion of the assembled hubs after they are attached to the outer cover tube. When the conductive sleeve is attached to the rear of the assembled hubs, the sleeve traps the exposed end of an isolated wire. In the illustrated embodiment, the isolated wire extends from its entrapment point under the conductive sleeve through a slot in the actuation tube and then inside a protective sleeve. The protective sleeve and isolated wire extend distally inside the actuation tube, towards the jaws. In other embodiments, the isolated wire can be formed integrally with a protective sheath and no separate protective sleeve is present in the actuation tube.

Attached to the distal end of the elongate shaft are jaws 222 that include a first jaw 270 and a second jaw 280. In one embodiment, a jaw pivot pin pivotally couples the first and second jaws and allows the first jaw to be movable and pivot relative to the second jaw. In various embodiments, one jaw is fixed with respect to the elongate shaft such that the opposing jaw pivots with respect to the fixed jaw between an open and a closed position. In other embodiments, both jaws can be pivotally coupled to the elongate shaft such that both jaws can pivot with respect to each other.

Attached to the first jaw is a conductive pad 272. In one embodiment, the isolated wire 273 is routed to electrically couple the conductive pad on the first jaw to the wiring harness in the actuator. The isolated wire extends from the distal end of the protective sleeve which is housed at the proximal end of the second jaw and extends into the first jaw. The first jaw can have a slot positioned to receive the isolated wire. The isolated wire then extends through a hole in the first jaw and drops into a slot in a nonconductive portion. The isolated wire then extends to the distal end of the nonconductive portion and drops through to the conductive pad.

In some embodiments, electrode geometry on the conductive pads of the jaw assembly ensures that the sealing area completely encloses the distal portion of the blade cutting path. In embodiment, the conductive pad 272 and the second jaw 280 are curved at the edges to maintain a distinctive sealing surface in contact with tissue between the jaws, reduced unwanted concentrated current density and/or to assist in cutting of tissue between the jaws. In some embodiments, for some surgical procedures the outer shape of the jaws can be curved such that the distal ends of the jaws are offset with respect to the longitudinal axis from the proximal ends of the jaws to improve visibility for a user such as a surgeon.

In accordance with various embodiments, the dimensions of the jaw surfaces are such that it is appropriately proportioned with regards to the optimal pressure applied to the tissue between the jaws for the potential force the force mechanism can create. Its surface area is also electrically significant with regards to the surface area contacting the tissue. This proportion of the surface area and the thickness of the tissue have been optimized with respect to its relationship to the electrical relative properties of the tissue.

The jaws are arranged to maintain electrically significant spacing between the jaws in relation to the thickness of tissue held between the jaws. In one embodiment, at least one jaw includes a conductive post 281 extending in a direction traverse to the longitudinal direction of the jaw. The post in various embodiments protrudes through an inner surface of the second jaw or lower jaw assembly and towards an inner surface or a conductive pad of the first jaw.

The conductive posts in one embodiment are made from a conductive material such as stainless steel. The conductive post in one embodiment being made from a stainless steel provides high compressive and/or column strength. As such, the conductive post can endure more operational wear and tear and can be dimensionally small relative to the dimensions of the jaw with a reduced concern of breakage or dislodgement or occupying excessive space on the jaw. In one embodiment the conductive posts are made of a material that is the same material as the conductive pad on the first and/or second jaws.

In accordance with various embodiments, multiple posts provided and support an inner edge of the conductive surface of the jaw that is adjacent to a blade channel within the jaw. In accordance with various embodiments, the posts also provide additional surface texture to aid with capturing and griping the tissue that is captured within the jaws of the device. The conductive posts however do not have and edge or an otherwise atraumatic surface to pierce, puncture or otherwise protrude through tissue grasped between the jaws.

The conductive post in one embodiment supports an inner edge of a conductive surface that is adjacent to the blade channel. The posts are biased to be at the edge of the blade channel. When the jaws are closed and RF energy is supplied, the conductive post is the same electrical potential as the conductive surface. The configuration of the conductive post relative to the conductive surface and the conductive post being the same electrical potential as the upper conductive surface provide in one embodiment a tissue treating surface that is uninterrupted along the jaw. In one embodiment, the configuration and electrical potential provide the application of RF energy allows heating and sealing around the conductive post further enhancing the seal quality or tissue treatment of the tissue between the jaws.

Additionally, to improve seal quality and reduce the potential for higher current density at the edges of the upper and lower conductive surfaces, the upper and lower conductive surfaces in one embodiment have a lead-in angle 274 and/or radius 275, configuration. In addition to addressing current density the radius also presents an atraumatic radii edge to the vessel adjacent to the area affected by RF energy application to help prevent cutting at the edge of the surface of the jaws.

The conductive posts in one embodiment are disposed along the jaw and each at a differing height relative to the others such that they are not on the same plane. In one embodiment, the conductive posts as such provide that the first or distal most conductive post to contact tissue first then one or more intermediate conductive posts and finally a proximal most conductive post. In one embodiment, the distal most post is 0.005", the intermediate is 0.004" and the proximal most post is 0.003". Such a staggered arrangement ensures the jaws or inner surfaces remain relatively parallel relative to the tissue and each other by compensating for the deflection of the first and/or second jaws when the force is applied. The height difference of the posts relative to the jaw in one embodiment can lift or raise portions of the tissue near or adjacent the blade channel and thereby aids with the gripping of the tissue as it is being cut and thereby provides a smoother cut and eases the cutting operation.

In one embodiment, the first jaw or upper jaw assembly comprises a stamped sheet metal conductive pad 272 that is held at a distance from the machined upper metal jaw 285 by a high service non-conductive temperature plastic material 276. The stamped sheet metal, non-conductive plastic material and machined upper metal jaw are placed into a mold which is subsequently filled with a thermoplastic. The result of the process is an over molded upper machined or MIM (metal injection molded) jaw, stamped conductive pad and high temperature plastic that are fixed or held together by the thermoplastic over-molding to make the first or upper jaw. In one embodiment, the upper jaw includes an injection molded component in place of the high service temperature non-conductive plastic material.

In one embodiment, the second jaw or lower jaw assembly comprises a machined or MIM jaw and machined or MIM electrically conductive posts 281. In one embodiment, the posts and jaw are made of the same material. The jaw and posts are placed into a mold which is subsequently filled with a thermoplastic. The result of the process is an over-molded lower jaw and conductive posts that are fixed or held together by the thermoplastic over-molding to make the lower jaw. By the posts extending from the lower jaw assembly and through an inner surface of the jaw, the strength and/or stability of the conductive posts are enhanced relative to the jaws and/or tissue. As such, in one embodiment, the post has a height that is at least twice the thickness of the conductive pad. In one embodiment, the post has a bottom portion that extends into about half the thickness or depth of the first and/or second jaw. Upon assembly a jaw gap is set in a fixture and laser welded and in one embodiment this is facilitated by a slotted hole in the lower jaw and a dowel.

Figure 38:
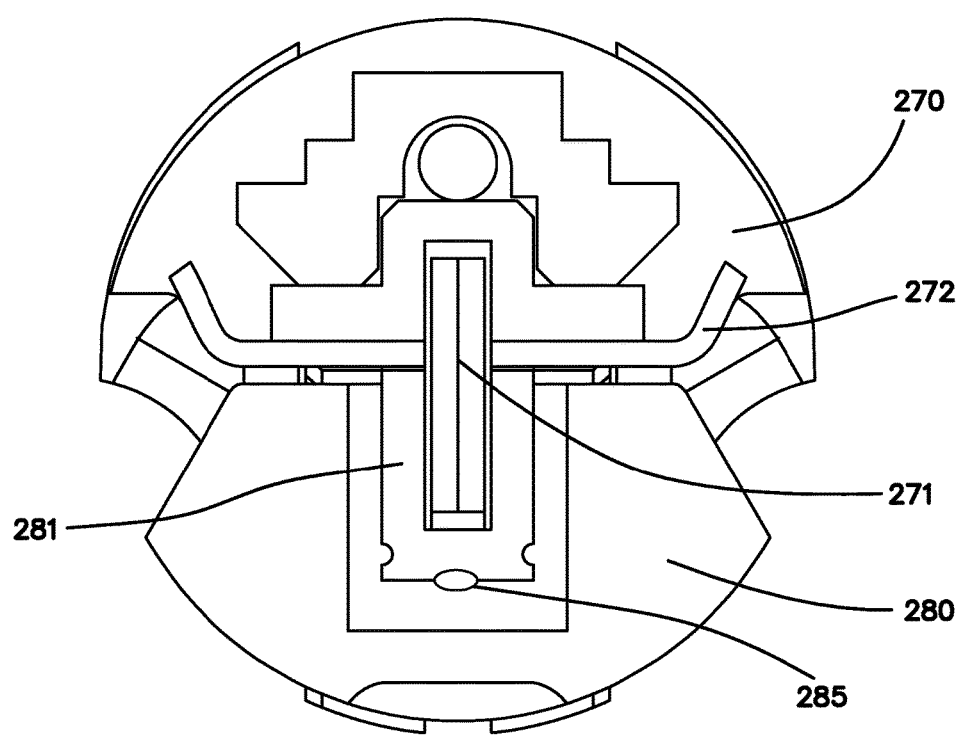
FIG. 38 is a front cross-sectional view of a distal end of an electrosurgical device in accordance with various embodiments of the present invention.
Figure 39:
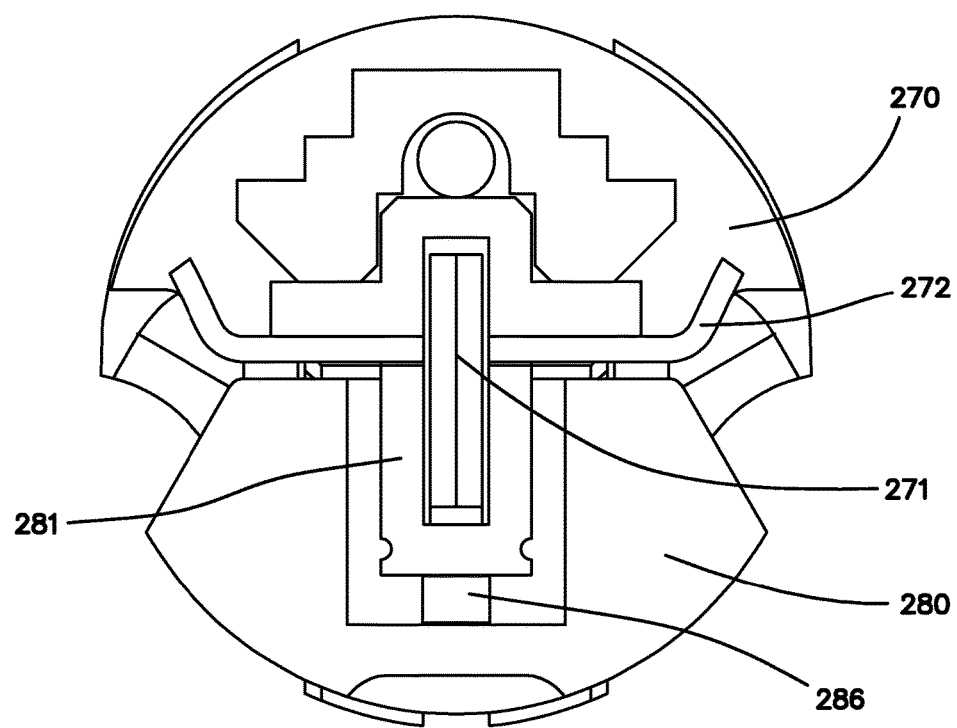
FIG. 39 is a front cross-sectional view of a distal end of an electrosurgical device in accordance with various embodiments of the present invention.
Figure 40:
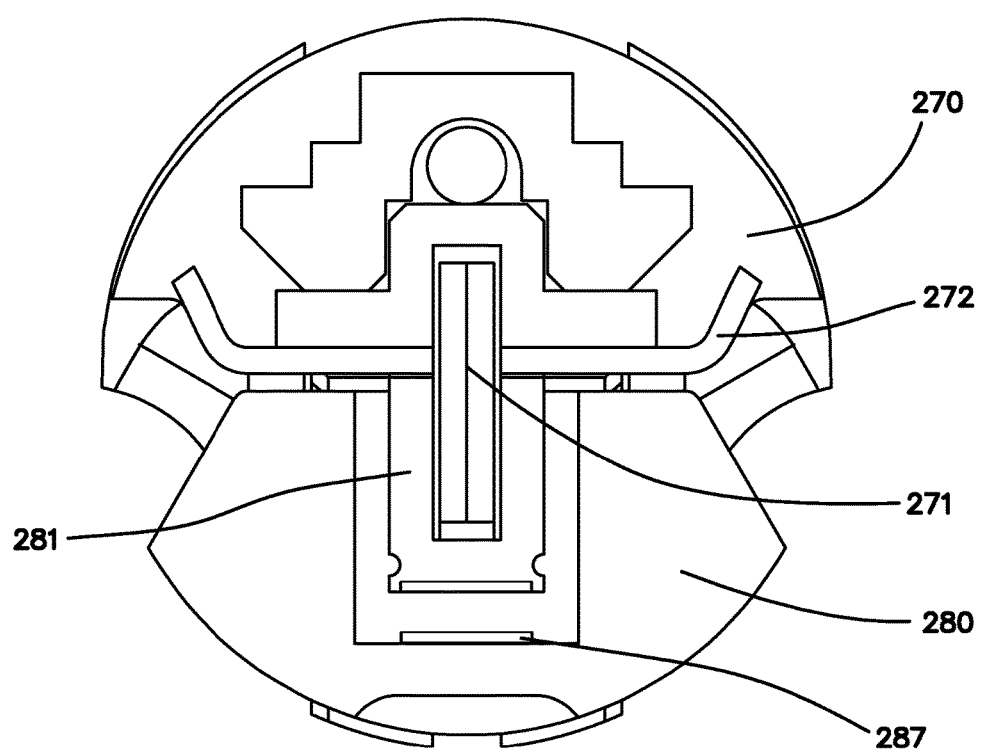
FIG. 40 is a front cross-sectional view of a distal end of an electrosurgical device in accordance with various embodiments of the present invention.

Referring to FIGS. 38-40, in one embodiment, a return path connection 285 is provided to connect the conductive posts to the generator. In such an embodiment, the conductive posts can provide additional feedback information such as applied voltage, current, power and phase, or tissue properties. In one embodiment, the return path connection provides an indicator or cutoff switch such that if the cutting blade enters the jaw a circuit is developed or a deliberate short is triggered to terminate RF energy and thereby ensure that RF energy is not being supplied while the blade is being actuated. In one embodiment, a thermistor or a temperature sensor 286 is disposed under or inline with the conductive post and connected back with a wire or return connection through the lower jaw to monitor the temperature, e.g., via the change in the thermistor caused by the temperature change. In one embodiment the electrosurgical generator can then account for the temperature of the tissue and the jaws that can effect fusing of the tissue and/or the application of the RF energy. In one embodiment, the second or lower jaw includes plates or a capacitive arrangement or sensor 287 and in one embodiment the electrosurgical generator can then measures the capacitance between a bottom surface of the conductive post and a portion of the jaw to account for instrument or tissue capacitance that can effect fusing of the tissue and/or the application of RF energy.

In accordance with various embodiments, an electrosurgical system can include an electrosurgical generator and an electrosurgical instrument. The electrosurgical instrument is used in laparoscopic procedures where the ligation and division of vessels and tissue bundles are desired. The electrosurgical instrument fuses vessels by delivering radio frequency (RF) energy to tissue captured between the jaws of the device and divides sealed tissue with a user-actuated blade. The generator can provide an electrosurgery endpoint by determining the phase end point of a tissue to be treated. The electrosurgical system can include more than one electrosurgical instrument for different electrosurgical operations and can include a variety of user interface features and audio/visual performance indicators. The electrosurgical system can also power conventional bipolar electrosurgical instruments and direct current surgical appliances.

Figures 27, 28:
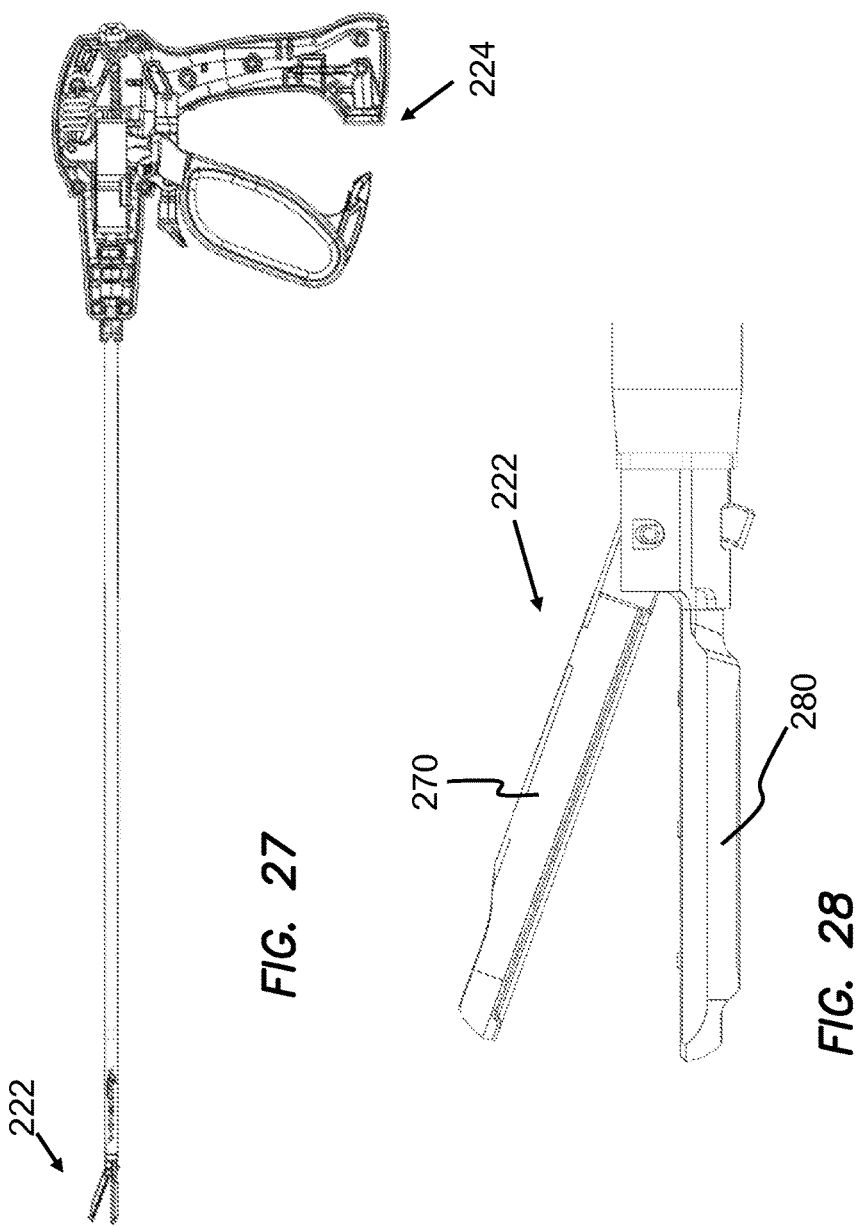
FIG. 27 is a side cross-sectional view of an electrosurgical device in accordance with various embodiments of the present invention.
FIG. 28 is a side view of a distal end of an electrosurgical device in accordance with various embodiments of the present invention.

Turning now to some of the operational aspects of the electrosurgical instrument or instrument described herein in accordance with various embodiments, once a vessel or tissue bundle has been identified for fusing, the first and second jaws are placed around the tissue. The movable handle 223 is squeezed moving the movable handle proximally with respect to the stationary housing 228. As the movable handle moves proximally it pushes the pull block. The pull block engages with the pull tube causing the pull tube to move proximally. Proximal movement of the pull tube pivots the first jaw towards the second jaw effectively clamping the tissue. In FIGS. 27-28, the actuator 224 is shown in a first or initial position in which the jaws 222 are in an open position and in one embodiment the first and second jaws opening defines about a 30 degree angle.

Figure 30:
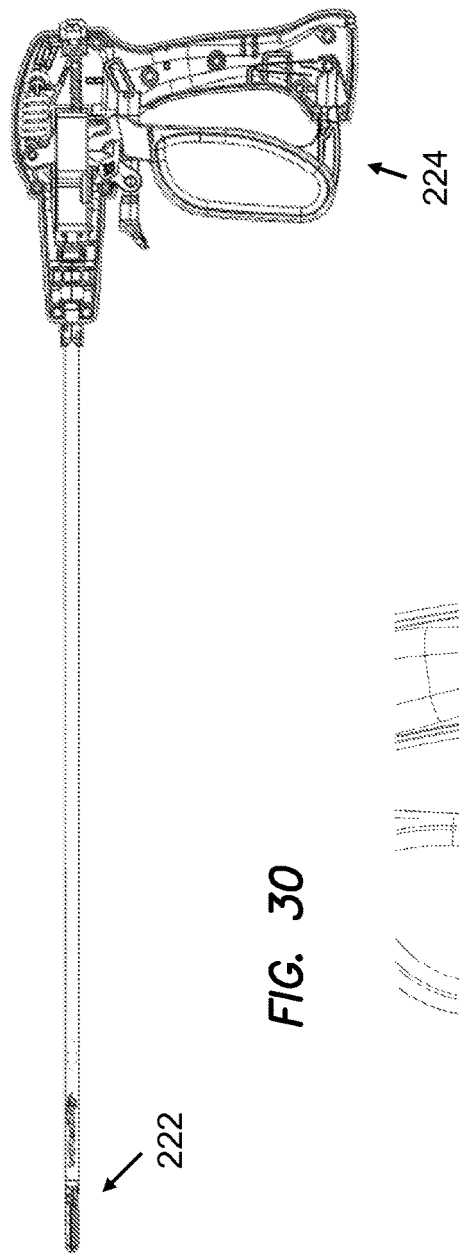
FIG. 30 is a side cross-sectional view of an electrosurgical device in accordance with various embodiments of the present invention.
Figure 31:
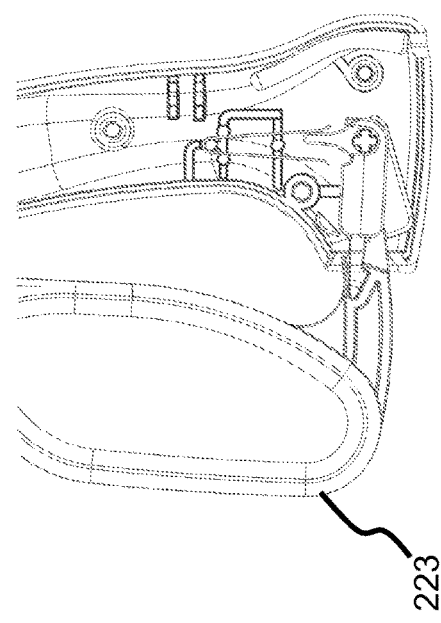
FIG. 31 is a side cross-sectional view of a portion of an actuator of an electrosurgical device in accordance with various embodiments of the present invention.
Figure 35:
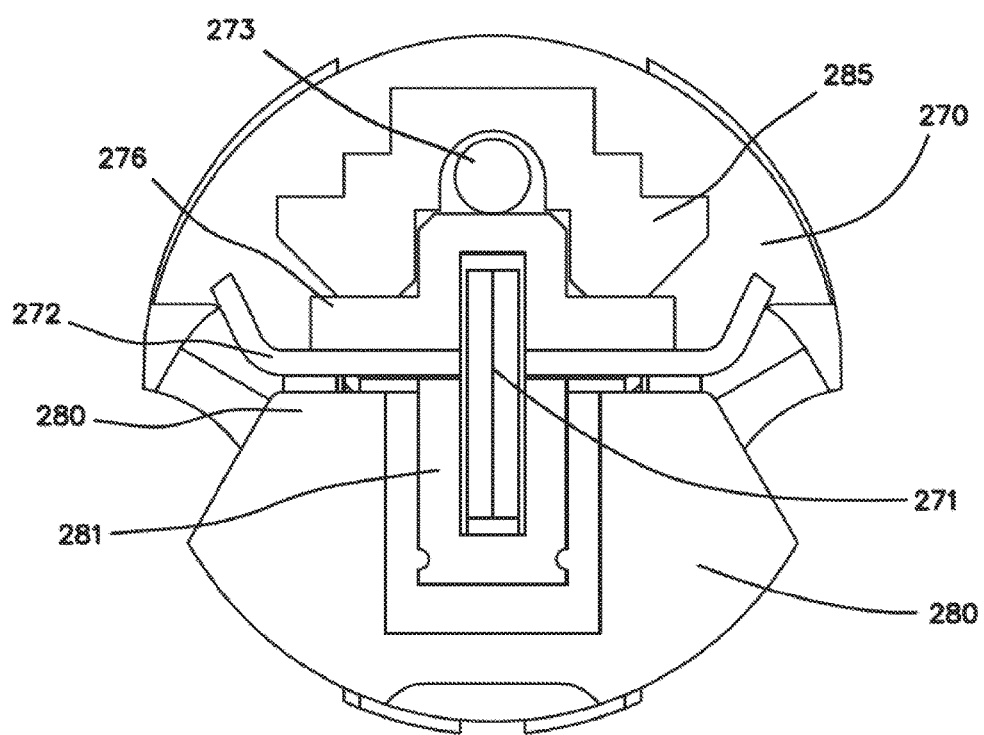
FIG. 35 is a front cross-sectional view of a distal end of an electrosurgical device in accordance with various embodiments of the present invention.

The continued manipulation of the movable handle pivots the movable handle to a location where the movable handle engages with the latch mechanism that maintains the movable handle in the engaged position and prevents the handle from returning to an opened position. From the engaged position, radio frequency energy is applied to the tissue by depressing the activation button. Once the tissue has been fused, the movable handle is reopened by continuing proximal advancement to a position that allows the latch mechanism to disengage. In FIGS. 30-31, the actuator 224 is shown in an engaged position in which the jaws 222 are closed and the movable handle is latched.

Figure 29:
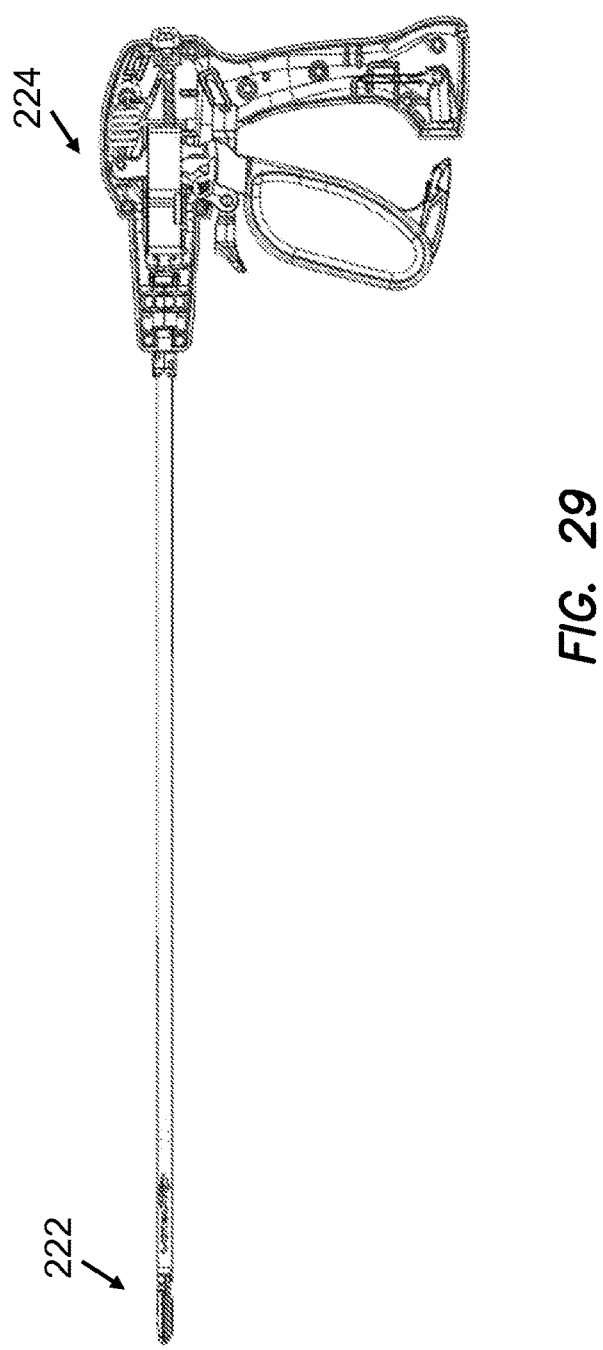
FIG. 29 is a side cross-sectional view of a distal end of an electrosurgical device in accordance with various embodiments of the present invention.

Alternatively or additionally, the user can actuate the blade trigger 225. When the blade trigger is moved proximally, the blade lever pivots, forcing the push bar and the cutting blade to move distally. The cutting blade advances forward and divides the sealed portion of the tissue. When the user releases the blade trigger, the blade spring resets the cutting blade to its original position. When the blade trigger has been returned to its original or initial position the user can continue to squeeze the movable handle to open the upper jaw. In FIGS. 32-33, the actuator 224 is shown in a cutting position in which the jaws 222 are in a closed position and the blade trigger has been depressed advancing the cutting blade to its distal most position. Continued proximal movement of the movable handle will disengage the latch mechanism to a position where the movable handle can be released. In FIG. 29, an intermediate position is shown in which the jaws are in a closed position and the movable handle is not latched. In one embodiment, the blade trigger may be activated to cut tissue between the jaws and/or the fuse button or switch may be activated to fuse tissue between the jaws.

Further examples of the electrosurgical unit, instruments and connections there between and operations and/or functionalities thereof are described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; and Ser. No. 12/416,128, filed Mar. 31, 2009, entitled "Electrosurgical System"; the entire disclosures of which are hereby incorporated by reference as if set in full herein.

The above description is provided to enable any person skilled in the art to make and use the surgical instruments and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. An electrosurgical system comprising:
   an electrosurgical instrument arranged to grasp and fuse tissue using radio frequency (RF) energy; and
   an electrosurgical generator connectable to the electrosurgical instrument and configured to supply the RF energy through the electrosurgical instrument, the generator comprising:
   an RF amplifier to supply RF energy through the electrosurgical instrument; and
   a controller arranged to monitor a phase angle of the supplied RF energy, the controller being configured to signal the RF amplifier to adjust voltage of the supplied RF energy when the monitored phase angle is equal to a predefined phase value, wherein the predefined phase value is zero degrees.

2. The electrosurgical system of claim 1 wherein an adjustment of voltage by the RF amplifier comprises the RF amplifier decreasing the voltage of the supplied RF energy.

3. The electrosurgical system of claim 1 wherein an adjustment of voltage by the RF amplifier comprises the RF amplifier setting the voltage of the supplied RF energy to a predetermined voltage.

4. The electrosurgical system of claim 3 wherein the controller is configured to determine a second predefined phase value based on and subsequent to the adjustment of voltage by the RF amplifier.

5. The electrosurgical system of claim 4 wherein the controller is configured to signal the RF amplifier to terminate the supply of RF energy when the monitored phase angle is less than the second predefined phase value.

6. An electrosurgical system comprising:
   an electrosurgical instrument arranged to grasp and fuse tissue using radio frequency (RF) energy; and
   an electrosurgical generator connectable to the electrosurgical instrument and configured to supply the RF energy through the electrosurgical instrument, the generator comprising:
   an RF amplifier to supply RF energy through the electrosurgical instrument; and
   a controller arranged to monitor a phase angle of the supplied RF energy, the controller configured to identify a first voltage of the supplied RF energy when the monitored phase angle starts decreasing.

7. The electrosurgical system of claim 6 wherein the controller is configured to determine a tissue size by comparing the identified first voltage to a predetermined voltage value.

8. The electrosurgical system of claim 7 wherein the controller is configured to determine a second predefined phase value using the determined tissue size.

9. The electrosurgical system of claim 6 wherein the controller is configured to determine a second predefined phase value using the identified first voltage.

10. The electrosurgical system of claim 9 wherein the controller is configured to signal the RF amplifier to terminate the supply of RF energy when the monitored phase angle is less than the second predefined phase value.

11. The electrosurgical system of claim 10 wherein the controller is configured to signal the RF amplifier to terminate the supply of RF energy when the monitored phase angle remains constant.

12. The electrosurgical system of claim 10 wherein the electrosurgical generator further comprises: an RF sense circuitry arranged to receive a supplied RF waveform from the supplied RF energy through the electrosurgical instrument; and a synchronous detector arranged to calculate real and imaginary voltage and current components of the supplied RF waveform.

13. The electrosurgical system of claim 10 wherein the electrosurgical instrument comprises:
   a first jaw having a first electrode;
   a second jaw coupled to the first jaw and having a second electrode facing the first electrode, the first and second electrodes arranged to conduct the supplied RF energy between the first and second electrodes and the first and second electrodes being made of the same conductive material;
   an elongate shaft having a proximal end and a distal end and a longitudinal axis extending from the proximal end to the distal end, the first and second jaws being pivotably coupled to the distal end of the elongate shaft; and
   a conductive post incorporated into the second jaw and extending from the second jaw towards the first jaw, the conductive post being stationary and made of the same conductive material as the first and second electrodes.

14. The electrosurgical system of claim 13 wherein the conductive post has an upper portion extending from an upper surface of the second jaw and a lower portion encased in an insulated material in the second jaw, the insulated material separating the conductive post from conductive material in the second jaw and the conductive post being not connectable to conductive material extending from the elongate shaft.

15. The electrosurgical system of claim 14 wherein the conductive post is in a contacting relationship with the first jaw with the first and second jaws being in a closed position and the conductive post has an outer periphery confined within an outer periphery of the second jaw.

16. The electrosurgical system of claim 15 wherein the conductive post includes a plurality of conductive posts having varying heights and the plurality of conductive posts includes a distal most conductive post having a height greater than a height of a proximal most conductive post.

17. The electrosurgical system of claim 16 wherein the conductive post is non-adjustable and rigid.

18. The electrosurgical system of claim 17 wherein the electrosurgical generator is configured to supply RF energy only to the first and second electrodes and not to the conductive post.

* * * * *